(12) United States Patent
Miller et al.

(10) Patent No.: US 9,932,286 B2
(45) Date of Patent: Apr. 3, 2018

(54) SIDE-CHAIN VARIANTS OF REDOX-ACTIVE THERAPEUTICS FOR TREATMENT OF MITOCHONDRIAL DISEASES AND OTHER CONDITIONS AND MODULATION OF ENERGY BIOMARKERS

(71) Applicant: BioElectron Technology Corporation, Mountain View, CA (US)

(72) Inventors: Guy M. Miller, Monte Sereno, CA (US); Sidney M. Hecht, Charlottesville, VA (US); Orion D. Jankowski, Burlingame, CA (US); Kieron E. Wesson, Menlo Park, CA (US); Paul Mollard, Saratoga, CA (US)

(73) Assignee: BioElectron Technology Corporation, Mountain View, CA (US)

( * ) Notice: Subject to any disclaimer, the term of this patent is extended or adjusted under 35 U.S.C. 154(b) by 0 days.

(21) Appl. No.: 14/983,330

(22) Filed: Dec. 29, 2015

(65) Prior Publication Data

US 2016/0244392 A1     Aug. 25, 2016

Related U.S. Application Data

(63) Continuation of application No. 11/710,042, filed on Feb. 22, 2007, now Pat. No. 9,278,085.

(60) Provisional application No. 60/776,028, filed on Feb. 22, 2006, provisional application No. 60/873,395, filed on Dec. 6, 2006.

(51) Int. Cl.
| | |
|---|---|
| C07C 50/38 | (2006.01) |
| C07C 50/04 | (2006.01) |
| A61K 31/05 | (2006.01) |
| A61K 31/355 | (2006.01) |
| C07C 39/08 | (2006.01) |
| C07C 39/11 | (2006.01) |
| C07C 39/19 | (2006.01) |
| C07C 39/24 | (2006.01) |
| C07C 50/02 | (2006.01) |
| C07C 50/06 | (2006.01) |
| C07C 50/24 | (2006.01) |
| C07C 50/28 | (2006.01) |
| C07C 215/56 | (2006.01) |
| C07C 403/04 | (2006.01) |
| C07C 403/08 | (2006.01) |
| C07C 403/18 | (2006.01) |
| C07C 43/225 | (2006.01) |
| C07C 43/23 | (2006.01) |
| C07C 47/277 | (2006.01) |
| C07C 69/608 | (2006.01) |
| C07C 69/618 | (2006.01) |
| C07C 233/27 | (2006.01) |
| C07C 233/32 | (2006.01) |
| C07C 255/37 | (2006.01) |

(52) U.S. Cl.
CPC .............. *C07C 50/04* (2013.01); *A61K 31/05* (2013.01); *A61K 31/355* (2013.01); *C07C 39/08* (2013.01); *C07C 39/11* (2013.01); *C07C 39/19* (2013.01); *C07C 39/245* (2013.01); *C07C 43/225* (2013.01); *C07C 43/23* (2013.01); *C07C 47/277* (2013.01); *C07C 50/02* (2013.01); *C07C 50/06* (2013.01); *C07C 50/24* (2013.01); *C07C 50/28* (2013.01); *C07C 69/608* (2013.01); *C07C 69/618* (2013.01); *C07C 215/56* (2013.01); *C07C 233/27* (2013.01); *C07C 233/32* (2013.01); *C07C 255/37* (2013.01); *C07C 403/04* (2013.01); *C07C 403/08* (2013.01); *C07C 403/18* (2013.01); *C07C 2601/16* (2017.05)

(58) Field of Classification Search
CPC ......... C07C 39/08; C07C 50/28; C07C 50/24; C07C 215/56; C07C 403/04; C07C 403/08; C07C 403/18; A61K 31/355
USPC ........................................................ 552/309
See application file for complete search history.

(56) References Cited

U.S. PATENT DOCUMENTS

| | | | |
|---|---|---|---|
| 2,398,418 | A | 4/1946 | Fieser |
| 2,856,414 | A | 10/1958 | Robeson et al. |
| 3,071,512 | A | 1/1963 | Feldmann |
| 3,406,188 | A | 10/1968 | Fletcher |
| 3,705,239 | A | 12/1972 | Gregory |

(Continued)

FOREIGN PATENT DOCUMENTS

| | | |
|---|---|---|
| CA | 2430415 | 6/2002 |
| CN | 1441793 | 9/2003 |

(Continued)

OTHER PUBLICATIONS

1957:81330 CAPLUS, "Studies in the vitamin K and E series, III, Analogs of a-tocopherol with unbranched sidechains", 1 page.

(Continued)

*Primary Examiner* — Barbara P Badio
(74) *Attorney, Agent, or Firm* — Squire Patton Boggs (US) LLP

(57) ABSTRACT

Methods of treating or suppressing mitochondrial diseases, such as Friedreich's ataxia (FRDA), Leber's Hereditary Optic Neuropathy (LHON), mitochondrial myopathy, encephalopathy, lactacidosis, stroke (MELAS), or Kearns-Sayre Syndrome (KSS) are disclosed, as well as compounds useful in the methods of the invention. Methods and compounds useful in treating other disorders are also disclosed. Energy biomarkers useful in assessing the metabolic state of a subject and the efficacy of treatment are also disclosed. Methods of modulating, normalizing, or enhancing energy biomarkers, as well as compounds useful for such methods, are also disclosed.

8 Claims, No Drawings

(56) References Cited

U.S. PATENT DOCUMENTS

| | | |
|---|---|---|
| T917,001 I4 | 12/1973 | Anderson, Jr. et al. |
| 3,849,453 A | 11/1974 | Morrimoto et al. |
| 3,896,153 A | 7/1975 | Sato et al. |
| 3,909,376 A | 9/1975 | Degner |
| 3,957,836 A | 5/1976 | Morimoto et al. |
| 4,127,608 A | 11/1978 | Olson |
| 4,153,614 A | 5/1979 | Barner et al. |
| 4,185,154 A | 1/1980 | Olson et al. |
| 4,201,726 A | 5/1980 | Olson et al. |
| 4,201,879 A | 5/1980 | Berner et al. |
| 4,234,490 A | 11/1980 | Barner et al. |
| 4,243,598 A | 1/1981 | Olson et al. |
| 4,310,465 A | 1/1982 | Olson et al. |
| 4,388,312 A | 6/1983 | Terao et al. |
| 4,393,075 A | 7/1983 | Terao et al. |
| 4,436,753 A | 3/1984 | Imada et al. |
| 4,491,594 A | 1/1985 | Ogawa et al. |
| 4,495,104 A | 1/1985 | Imada et al. |
| 4,559,177 A | 12/1985 | Okutani et al. |
| 4,559,407 A | 12/1985 | Barner et al. |
| 4,592,867 A | 6/1986 | Yu et al. |
| 4,599,232 A | 7/1986 | Bertelli |
| 4,617,317 A | 10/1986 | Bennet |
| 4,694,090 A | 9/1987 | Shiono et al. |
| 4,804,539 A | 2/1989 | Guo et al. |
| 4,814,346 A | 3/1989 | Albert et al. |
| 4,818,441 A | 4/1989 | Imada et al. |
| 4,831,265 A | 5/1989 | Watanabe et al. |
| 4,883,658 A | 11/1989 | Holly |
| 4,914,088 A | 4/1990 | Glonek et al. |
| 5,057,514 A | 10/1991 | Tatsuoka et al. |
| 5,059,627 A | 10/1991 | Goto et al. |
| 5,075,104 A | 12/1991 | Gressel et al. |
| 5,157,132 A | 10/1992 | Tan et al. |
| 5,179,092 A | 1/1993 | Tatsuoka et al. |
| 5,180,742 A | 1/1993 | Terao et al. |
| 5,190,618 A | 3/1993 | Top et al. |
| 5,210,239 A | 5/1993 | Abe et al. |
| 5,229,385 A | 7/1993 | Terao et al. |
| 5,278,151 A | 1/1994 | Korb et al. |
| 5,288,752 A | 2/1994 | Tatsuoka et al. |
| 5,292,768 A | 3/1994 | Tatsuoka et al. |
| 5,294,607 A | 3/1994 | Glonek et al. |
| 5,304,658 A | 4/1994 | Terao et al. |
| 5,318,993 A | 6/1994 | Pearce |
| 5,371,108 A | 12/1994 | Korb et al. |
| 5,547,827 A | 8/1996 | Chen et al. |
| 5,578,586 A | 11/1996 | Glonek et al. |
| 5,600,029 A | 2/1997 | Kaneko et al. |
| 5,801,159 A | 9/1998 | Miller et al. |
| 5,846,988 A | 12/1998 | Hellberg |
| 5,872,108 A | 2/1999 | Sandage, Jr. et al. |
| 5,874,461 A | 2/1999 | De Chaffoy de Courcelles et al. |
| 5,886,030 A | 3/1999 | Maniar |
| 5,969,133 A | 10/1999 | Ono et al. |
| 5,981,601 A | 11/1999 | Nagley et al. |
| 6,011,046 A | 1/2000 | Ohkawa et al. |
| 6,045,826 A | 4/2000 | Borowy-Borowski et al. |
| 6,083,982 A | 7/2000 | Wechter et al. |
| 6,133,278 A | 10/2000 | Terao et al. |
| 6,133,322 A | 10/2000 | Rustin et al. |
| 6,136,859 A | 10/2000 | Henriksen |
| 6,150,402 A | 11/2000 | Wechter et al. |
| 6,187,811 B1 | 2/2001 | Lane |
| 6,232,060 B1 | 5/2001 | Miller et al. |
| 6,239,171 B1 | 5/2001 | Lane et al. |
| 6,271,266 B1 | 8/2001 | Miyamoto et al. |
| 6,297,281 B1 | 10/2001 | Chabier de Lassauniere et al. |
| 6,300,377 B1 | 10/2001 | Chopra |
| 6,331,532 B1 | 12/2001 | Murphy et al. |
| 6,342,516 B1 | 1/2002 | Umeda et al. |
| 6,395,915 B1 | 5/2002 | Bellafiore et al. |
| 6,417,233 B1 | 7/2002 | Sears et al. |
| 6,426,362 B1 | 7/2002 | Miller et al. |
| 6,433,199 B1 | 8/2002 | Ono et al. |
| 6,472,378 B2 | 10/2002 | Von Borstel |
| 6,528,042 B1 | 3/2003 | Brown et al. |
| 6,545,184 B1 | 4/2003 | Lipshutz |
| 6,608,196 B2 | 8/2003 | Wang et al. |
| 6,653,346 B1 | 11/2003 | Wang et al. |
| 6,656,358 B2 | 12/2003 | May et al. |
| 6,740,338 B1 | 5/2004 | Chopra |
| 6,764,768 B2 | 7/2004 | Mrksich et al. |
| 6,838,104 B2 | 1/2005 | Jacobs |
| 6,852,895 B2 | 2/2005 | Lipshutz et al. |
| 6,977,270 B2 | 12/2005 | Baldenius et al. |
| 7,034,054 B2 | 4/2006 | Miller et al. |
| 7,038,067 B2 | 5/2006 | Couladouros et al. |
| 7,078,541 B2 | 7/2006 | Boddupalli et al. |
| 7,118,688 B2 | 10/2006 | Mora-Gutierrez et al. |
| 7,119,117 B2 | 10/2006 | Beinlich et al. |
| 7,393,662 B2 | 7/2008 | Heavner et al. |
| 7,432,305 B2 | 10/2008 | Miller et al. |
| 7,470,798 B2 | 12/2008 | Wang et al. |
| 7,491,312 B2 | 2/2009 | Gilat et al. |
| 7,514,461 B2 | 4/2009 | Wang et al. |
| 7,718,176 B2 | 5/2010 | Heavner et al. |
| 7,875,607 B2 | 1/2011 | Wang et al. |
| 7,968,746 B2 | 6/2011 | Jankowski et al. |
| 8,044,097 B2 | 10/2011 | Wang et al. |
| 8,106,223 B2 | 1/2012 | Wesson et al. |
| 8,182,990 B2 | 5/2012 | Mashima et al. |
| 8,314,153 B2 | 11/2012 | Miller et al. |
| 8,394,392 B2 | 3/2013 | Imahashi et al. |
| 8,519,001 B2 | 8/2013 | Jankowski et al. |
| 8,575,369 B2 | 11/2013 | Wesson et al. |
| 8,653,144 B2 | 2/2014 | Miller et al. |
| 8,716,486 B2 | 5/2014 | Hinman et al. |
| 8,716,527 B2 | 5/2014 | Hinman et al. |
| 8,791,155 B2 | 7/2014 | Wang et al. |
| 2001/0044462 A1 | 11/2001 | Hensley et al. |
| 2002/0132845 A1 | 9/2002 | Miller et al. |
| 2002/0142083 A1 | 10/2002 | Jacobs et al. |
| 2002/0182196 A1 | 12/2002 | McCleary |
| 2003/0022818 A1 | 1/2003 | Miller et al. |
| 2003/0119054 A1 | 6/2003 | Mrksich et al. |
| 2003/0144219 A1 | 7/2003 | Phinney et al. |
| 2003/0158237 A1 | 8/2003 | Saragovi et al. |
| 2004/0043013 A1 | 3/2004 | McCleary |
| 2004/0156871 A1 | 8/2004 | Borowy-Borowski et al. |
| 2005/0043553 A1 | 2/2005 | Smith et al. |
| 2005/0049227 A1 | 3/2005 | Old et al. |
| 2005/0065099 A1 | 3/2005 | Walkinshaw et al. |
| 2005/0065150 A1 | 3/2005 | Wang et al. |
| 2005/0074447 A1 | 4/2005 | Papas et al. |
| 2005/0186518 A1 | 8/2005 | Masskasky et al. |
| 2005/0203066 A1 | 9/2005 | von Borstel |
| 2005/0222218 A1 | 10/2005 | Meier et al. |
| 2005/0234248 A1 | 10/2005 | Kossler et al. |
| 2006/0002885 A1 | 1/2006 | Mielke et al. |
| 2006/0241174 A1 | 10/2006 | Mueller et al. |
| 2006/0281809 A1 | 12/2006 | Miller et al. |
| 2007/0066541 A1 | 3/2007 | Hughes et al. |
| 2007/0225261 A1 | 9/2007 | Miller et al. |
| 2007/0248590 A1 | 9/2007 | Jill et al. |
| 2008/0093985 A1 | 4/2008 | Morishita et al. |
| 2008/0221050 A1 | 9/2008 | Mashima |
| 2009/0036542 A1 | 2/2009 | Luu et al. |
| 2009/0060981 A1 | 3/2009 | Chauhan |
| 2009/0162890 A1 | 6/2009 | Gilat et al. |
| 2009/0163529 A1 | 6/2009 | Gilat et al. |
| 2009/0291092 A1 | 11/2009 | Miller et al. |
| 2010/0010100 A1 | 1/2010 | Hinman et al. |
| 2010/0029784 A1 | 2/2010 | Hinman et al. |
| 2010/0056429 A1 | 3/2010 | Miller et al. |
| 2010/0093845 A1 | 4/2010 | Wong et al. |
| 2010/0222436 A1 | 9/2010 | Miller et al. |
| 2010/0249032 A1 | 9/2010 | Heavner et al. |
| 2010/0266591 A1 | 10/2010 | Bugelski et al. |
| 2010/0273892 A1 | 10/2010 | Miller et al. |
| 2010/0273894 A1 | 10/2010 | Miller |
| 2011/0046156 A1 | 2/2011 | Miller |
| 2011/0046219 A1 | 2/2011 | Hinman et al. |
| 2011/0124679 A1 | 5/2011 | Hinman et al. |

(56) References Cited

U.S. PATENT DOCUMENTS

| | | |
|---|---|---|
| 2011/0142834 A1 | 6/2011 | Miller |
| 2011/0172312 A1 | 7/2011 | Miller et al. |
| 2011/0207828 A1 | 8/2011 | Miller et al. |
| 2011/0218208 A1 | 9/2011 | Hinman et al. |
| 2011/0263720 A1 | 10/2011 | Paisley et al. |
| 2011/0269776 A1 | 11/2011 | Miller |
| 2012/0088783 A1 | 4/2012 | Wang et al. |
| 2012/0101169 A1 | 4/2012 | Hawi |
| 2012/0122969 A1 | 5/2012 | Miller |
| 2012/0130093 A1 | 5/2012 | Wesson et al. |
| 2012/0136048 A1 | 5/2012 | Miller et al. |
| 2012/0295985 A1 | 11/2012 | Miller et al. |
| 2013/0053450 A1 | 2/2013 | Miller et al. |
| 2013/0109759 A1 | 5/2013 | Miller |
| 2013/0116336 A1 | 5/2013 | Shrader |
| 2013/0267538 A1 | 10/2013 | Walkinshaw et al. |
| 2013/0289034 A1 | 10/2013 | Jankowski et al. |
| 2013/0345312 A1 | 12/2013 | Jankowski et al. |
| 2014/0031432 A1 | 1/2014 | Jankowski et al. |
| 2014/0031433 A1 | 1/2014 | Miller et al. |
| 2014/0039065 A1 | 2/2014 | Miller |
| 2014/0206772 A1 | 7/2014 | Miller et al. |
| 2014/0221674 A1 | 8/2014 | Wesson et al. |
| 2014/0243424 A1 | 8/2014 | Mollard et al. |
| 2014/0249160 A1 | 9/2014 | Miller et al. |
| 2014/0249332 A1 | 9/2014 | Mollard et al. |
| 2014/0256830 A1 | 9/2014 | Hinman et al. |
| 2015/0057363 A1 | 2/2015 | Miller et al. |
| 2015/0216820 A1 | 8/2015 | Miller et al. |
| 2015/0218079 A1 | 8/2015 | Shrader et al. |
| 2016/0024085 A1 | 1/2016 | Hinman et al. |
| 2016/0115141 A1 | 4/2016 | Hinman et al. |

FOREIGN PATENT DOCUMENTS

| | | |
|---|---|---|
| DE | 3818696 C1 | 3/1989 |
| EP | 0025692 A1 | 3/1981 |
| EP | 0065368 A1 | 11/1982 |
| EP | 0107806 A1 | 5/1984 |
| EP | 0107806 B1 | 5/1984 |
| EP | 0134198 A1 | 3/1985 |
| EP | 0326987 | 8/1989 |
| EP | 0619313 A1 | 10/1994 |
| EP | 0629400 A1 | 12/1994 |
| EP | 0719552 A2 | 7/1996 |
| EP | 0719552 A3 | 7/1996 |
| EP | 1378753 A1 | 1/2004 |
| EP | 1378753 B1 | 1/2004 |
| EP | 1611879 A1 | 1/2006 |
| FR | 1.201.200 | 12/1959 |
| FR | 75.631 | 6/1961 |
| FR | 5.531 M | 12/1967 |
| FR | 1.536.576 | 8/1968 |
| JP | 40-9029 | 5/1965 |
| JP | 48-75564 A | 10/1973 |
| JP | 49-88862 A | 8/1974 |
| JP | 52-111576 A | 9/1977 |
| JP | 52-130922 | 11/1977 |
| JP | 56-140943 A | 11/1981 |
| JP | 57-050935 A | 3/1982 |
| JP | 58-018374 | 2/1983 |
| JP | 58-083698 A | 5/1983 |
| JP | 58-193689 A | 11/1983 |
| JP | 60-28919 A | 2/1985 |
| JP | 60-056902 A | 4/1985 |
| JP | 60-197621 | 10/1985 |
| JP | 61-040236 A | 2/1986 |
| JP | 63-063674 A | 3/1988 |
| JP | 1-093554 A | 4/1989 |
| JP | 1-209445 A | 8/1989 |
| JP | 1-233278 A | 9/1989 |
| JP | 5-11467 A | 1/1993 |
| JP | 8-92151 A | 3/1996 |
| JP | 2000-202297 | 7/2000 |
| JP | 2000-202297 A | 7/2000 |
| JP | 2003-64017 | 3/2003 |
| JP | 2003-64017 A | 3/2003 |
| JP | 2003-137716 | 5/2003 |
| JP | 2003-137716 A | 5/2003 |
| JP | 2007-529218 A | 10/2007 |
| WO | WO-93/24650 A1 | 12/1993 |
| WO | WO-98/34646 A2 | 8/1998 |
| WO | WO-1999/25336 A1 | 5/1999 |
| WO | WO-1999/38860 A1 | 8/1999 |
| WO | WO-2000/35444 A1 | 6/2000 |
| WO | WO-00/50043 A1 | 8/2000 |
| WO | WO-2000/78296 A2 | 12/2000 |
| WO | WO-2000/78296 A3 | 12/2000 |
| WO | WO-2001/52822 A1 | 7/2001 |
| WO | WO-2001/92215 A2 | 12/2001 |
| WO | WO-2001/92215 A3 | 12/2001 |
| WO | WO-2002/006261 A1 | 12/2001 |
| WO | WO-02/34259 A1 | 5/2002 |
| WO | WO-02/047680 A2 | 6/2002 |
| WO | WO-02/047680 A3 | 6/2002 |
| WO | WO-02/047680 A9 | 6/2002 |
| WO | WO-02/050054 A2 | 6/2002 |
| WO | WO-02/050054 A3 | 6/2002 |
| WO | WO-02/067864 A2 | 9/2002 |
| WO | WO-02/067864 A3 | 9/2002 |
| WO | WO-03/064403 A1 | 8/2003 |
| WO | WO-2004/003565 A2 | 1/2004 |
| WO | WO-2004/003565 A3 | 1/2004 |
| WO | WO-2004/042353 A2 | 5/2004 |
| WO | WO-2004/042353 A3 | 5/2004 |
| WO | WO-2005/000357 A2 | 1/2005 |
| WO | WO-2005/000357 A3 | 1/2005 |
| WO | WO-2005/013911 A2 | 2/2005 |
| WO | WO-2005/013911 A3 | 2/2005 |
| WO | WO-2005/019232 A1 | 3/2005 |
| WO | WO-2005/032544 A1 | 4/2005 |
| WO | WO-2005/033092 A1 | 4/2005 |
| WO | WO-2005/033093 A1 | 4/2005 |
| WO | WO-2005/090602 A2 | 9/2005 |
| WO | WO-2005/090602 A3 | 9/2005 |
| WO | WO-2005/105159 A2 | 11/2005 |
| WO | WO-2005/105159 A3 | 11/2005 |
| WO | WO-2007/095630 A2 | 8/2007 |
| WO | WO-2007/095630 A3 | 8/2007 |
| WO | WO 2008/142433 A1 | 11/2008 |
| WO | WO-2008/157747 A1 | 12/2008 |
| WO | WO-2009/023877 A2 | 2/2009 |
| WO | WO-2009/023877 A3 | 2/2009 |
| WO | WO-2011/041452 A2 | 4/2011 |
| WO | WO-2011/113018 A1 | 9/2011 |
| WO | WO-2012/019032 A1 | 2/2012 |
| WO | WO-2012/154613 A1 | 11/2012 |
| WO | WO-2012/170773 A1 | 12/2012 |
| WO | WO-2013/006736 A1 | 1/2013 |
| WO | WO-2014/039682 A1 | 3/2014 |

OTHER PUBLICATIONS 202843-61-6 Registry, Mar. 19, 1998, 2,5-Cydohexadiene-1,4-dione, 2,3,5-trimethyl-6-[(2E)-3-methyl-2-nonen-1-yl], 1 page.

82925-41-5 Registry, Nov. 16, 1984, 1,4-Benzenediol, 2,3,5-trimethyl-6-(3-methyl-2-nonadeceri-1-yl), 1 page.

Adelwohrer, C. et al. (2005, e-pub. Aug. 2, 2005). "Novel Tocopheryl Compounds XX. 1,3,8-Trioxaphenanthrenes Derived from y-Tocopherol," Tetrahedron 61:9070-9074.

Alexander, C. et al. (Oct. 2000). "OPA1, Encoding a Dynamin-Related GTPase, is Mutated in Autosomal Dominant Optic Atrophy Linked to Chromosome 3q28," Nature Genetics 26(2):211-215.

Anonymous (1976), "028 CGI Clinical Global Impressions," in Early Clinical Drug Evaluation Unit (ECDEU) Assessment Manual for Psychopharmacology, U.S. Department of Health, Education, and Welfare, pp. 217-222.

Anonymous (Feb. 2010), "List of Publications Noting Mitochondrial Involvement in Diseases," 3 pages.

Anonymous (2006), "Mitochondrial Dysfunction Contribution to Bipolar Disorder Confirmed Using Model Mice," Press Release from Riken Brain Science Institute located at http://web.archive.

(56) References Cited

OTHER PUBLICATIONS org/web/2012030316199/ htto://www.riken.ip/enon/r-world/infor/pressrelease/press/2006/060418/index.html, last visited Feb. 10, 2015, 5 pages.

Anonymous. (2011). "Mitochondrial Myopathy," located at http://www.ninds.nih.gov/disorders/mitochondrial_myopathy/mitochondrial_myopathy.html, last visited Feb. 10, 2015; 2 pages.

Armstrong, J.S. et al. (Dec. 5, 2003). "The Coenzyme Q10 Analog Decylubiquinone Inhibits the Redox-Activated Mitochondrial Permeability Transition," The Journal of Biological Chemistry 278(49):49079-49084.

Asgill, J.O. et al. (Jan. 4, 1978). "Chromenylation of 2-Napthol and Alkylhydroquinones: Short Syntheses of (2RS,4'R,8R)-a-Tocopherol (Vitamin E) and (2RS,4'R,8'R)-13-Tocopherol," The Journal of the Chemical Society Chemical Communications 1:59-60.

Asin-Cayuela, J. et al. (Jul. 30, 2004). "Fine-Tuning the Hydrophobicity of a Mitochondria-Targeted Antioxidant," FEBS Letters 571(1-3):9-16.

Babiroli, B. et al. (Jul. 1995). "Lipoic (Thioctic) Acid Increases Brain Energy Availability and Skeletal Muscle Performance as Shown by In Vivo 31P-MRS in a Patient with Mitochondrial Cytopathy," Journal of Neurology 242(7):472-477.

Beers, M.H. ed. et al. (1999). "Cerebrovascular Disease," Chapter 174 in The Merck Manual of Diagnosis and Therapy, 17th Edition, Merck Research Laboratories, Whitehouse Station, NJ, pp. 1417-1424.

Bentinger, M. et al. (2008). "Polyisoprenoid Epoxides Stimulate the Biosynthesis of Coenzyme Q and Inhibit Cholesterol Synthesis," The Journal of Biological Chemistry 283(21):14645-14653.

Bentinger, M. et al. (2008). "Stimulation of Coenzyme Q Synthesis," BioFactors 32:99-111.

Bernas T. et al. (2002). "Mitochondrial and Nonmitochondrial Reduction of MTT: Interaction of MTT With TMRE, JC-1, and NAO Mitochondrial Fluorescent Probes," Cytometry 47:236-242.

Berridge M. et al. (2005). "Tetrazolium dyes as tools in cell biology: New insights into their cellular reduction," Biotechnology Annual Review 11:127-152.

Bertamini, M. et al. (2002). "Mitochondrial Oxidative Metabolism in Motor Neuron Degeneration (mnd) Mouse Central Nervous System," European Journal of Neuroscience 16(12):2291-2296.

Bilenko, M.V. et al. (Sep. 1983). "Use of Antioxidants to Prevent Damage During Acute Ischemia and Reperfusion of the Kidneys," Byulleten'Eksperimental'noi Biologii i Meditsiny 96(9):8-11. (Abstract only).

Biousse, V. et al. (Feb. 2003). "Neuro-Ophthalmology of Mitochondrial Diseases," Current Opinion in Neurology, 16(1):35-43.

Boyer, P.D. (Feb. 19, 1951). "The Preparation of Reversible Oxidation Product of a-Tocopherol, a-Tocopheroxide and of Related Oxides," Journal of the American Chemical Society 73(2):733-740.

Bremner, F.D. (2004). "Pupil Assessment in Optic Nerve Disorders," Eye 18:1175-1181.

Bridgelius-Flohe, R. et al. (Jul. 1999). "Vitamin E: Function and Metabolism," The FASEB Journal, vol. 13, No. 10, pp. 1145-1155.

Briere, J-J.et al.(Apr. 16, 2004). "Quinone Analogues Regulate Mitochondrial Substrate Competitive Oxidation," Biochemical and Biophysical Research Communications 316(4):11381142.

Brown, M.D. et al. (Jul. 1992). "Leber's Hereditary Optic Neuropathy: A Model for Mitochondrial Neurodegenerative Diseases," The FASEB Journal 6:2791-2799.

Buranrat et al. (2012). "NQO1 Expression Correlates with Cholangiocarcinoma Prognosis," Asian Pacific J. Cancer Prev. 13:131-136.

Butterfield, D.A. et al. (2002). "Vitamin E and Neurodegenerative Disorders Associated with Oxidative Stress," Nutritional Neuroscience 5(4):229-239.

Calabresi P. and Chabner BA, "Section IX Chemotherapy of Neoplastic—Introduction," Goodman Gillman's The Pharmacological Basis of Therapeutics 10th ed., 2001, Hardman JG, Limbird LE, and Gilman AG, Eds., McGraw-Hill, New York 2001, 1381-1388 (pp. 1-3 and 1381-1388 provided).

Calviello G. et al. (2003). "γ-Tocopheryl Quinone Induces Apoptosis in Cancer Cells Via Caspase-9 Activation and Cytochrome c Release," Carcionogenesis 24(3):427-433.

Canter, J.A. et al. (May 2008). "Mitochondrial DNA Polymorphism A4917G Is Independently Associated with Age-Related Macular Degeneration," PloS One 3(5):e2091, 4 pages.

CAPLUS Accession No. 1967:18647, created May 12, 1984, 9 pages.

CAPLUS Accession No. 1969:433438, created May 12, 1984, 1 page.

CAPLUS Accession No. 1969:524242, created May 12, 1984, 3 pages.

CAPLUS Accession No. 1989:553350, created Oct. 28, 1999, 4 pages.

CAPLUS Accession No. 2003:166979, created Mar. 5, 2003, 5 pages.

CAPLUS Accession No. 2003:487787, created Jun. 27, 2003, 8 pages.

Carelli, V. (2002). "Optic Nerve Degeneration and Mitochondrial Dysfunction: Genetic and Acquired Optic Neuropathies," Neurochemistry International 40:573-584.

Carelli, V. et al. (2009, e-pub. Mar. 5, 2009). "Retinal Ganglion Cell Neurodegeneration in Mitochondrial Inherited Disorders," Biochimica et Biophysica Acta 1787:518-528.

Catlin Joseph C et al: "New Hydroquinones, Apparent Inhibitors of Coenzyme Q Enzyme Systems", Journal of the American Chemical Society, Jun. 19, 1968 (Jun. 19, 1968), pp. 3572-3574, XP55065560, Retrieved from the Internet: LIRL:httgil_pubs.acs.oratdoilpal 0.1021lia01015a054 [retrieved on Jun. 6, 2013].

Chariot, P. et al. (Apr. 1994). "Determination of the Blood Lactate: Pyruvate Ratio as a Noninvasive Test for the Diagnosis of Zidovudine Myopathy," Arthritis & Rheumatism 37(4):583-586.

Chariot, P. et al. (Jul. 1994). "Optimal Handling of Blood Samples for Routine Measurement of Lactate and Pyruvate," Archives of Pathology & Laboratory Medicine 118(7):695-697.

Choi, D.W. (Oct. 1988). "Glutamate Neurotoxicity and Diseases of the Nervous System," Neuron. 1(8):623-634.

Chow, C.K. et al. (Sep. 1967). "The Metabolism of C14-a-Tocopheryl Quinone and C14-a-Tocopheryl Hydroquinone," Lipids 2(5):390-396.

Christen, S. et al. (Apr. 1997). "γ-Tocopherol Traps Mutagenic Electrophiles Such as NOX and Complements α-Tocopherol: Physiological Implications,"Proc. Natl. Acad. Sci. USA 94(7):3217-3222.

Cichewicz, R.H. et al. (2004, e-pub. Oct. 23, 2004). "Redox Inactivation of Human 15-Liopsygenase by Marine-Derived Meroditerpenes and Synthetic Chromanes: Archetypes for a Unique Class of Selective and Recyclable Inhibitors," Journal of the American Chemical Society 126(45):14910-14920.

Cohen, N. et al. (1981). "Studies on the Total Synthesis of (2R,4'R,8'R)-a-Tocopherol (Vitamin E). Stereospecific Cyclizations Leading to Optically Active Chromans," The Journal of Organic Chemistry 46(12):2445-2450.

Cornwell, D.G. et al. (1998). "Cytotoxicity of Tocopherols and Their Quinones in Drug-Sensitive and Multidrug-Resistant Leukemia Cells," Lipids 33(3):295-301.

Cressman, H.W. et al. (Apr. 1966). "One-Step Synthesis of Polyalkyl-2-lodo-p Benzoquinones," Journal of Organic Chemistry 31(4):1279-1281.

Csaky, K.G. (Mar./Apr. 2007). "New Developments in the Transscleral Delivery of Ophthalmic Agents," Retina Today, pp. 32-35.

Dearling et al. (Mar. 2002, e-pub. Sep. 8, 2001). "Copper Bis(Thiosemicarbazone) Complexes as Hypoxia Imaging Agents: Structure-Activity Relationships," J. Biol. Inorg. Chem. 7(3):249-259.

Delettre, C. et al. (Oct. 2000). "Nuclear Gene OPA1, Encoding a Mitochondrial Dynamin-Related Protein, is Mutated in Dominant Optic Atrophy," Nature Genetics 26(2):207-210.

(56) References Cited

OTHER PUBLICATIONS

Diener, H.C. et al. (Jan. 1996). "Lubeluzole in Acute Ischemic Stroke. A Double-Blind, Placebo-Controlled Phase II Trial," Stroke 27(1):76-81.
Donato, S.D. et al. (2001). "The Complex Clinical and Genetic Classification of Inherited Ataxias. II. Autosomal Recessive Ataxias," Neurol. Sci. 22:219-228.
Dowd, P. et al. (Aug. 1995). "On the Mechanism of the Anticlotting Action of Vitamin E Quinone," Proceedings of The National Academy of Science USA 92:8171-8175.
Duong, T.Q. (Jul. 2004). "Applications of Diffusion/Perfusion Magnetic Resonance Imaging in Experimental and Clinical Aspects of Stroke," Curr. Atheroscler Rep. 6(4):267-273.
Durckheimer, W. et al. (Oct. 20, 1964). "The Chemistry of 9-Hydroxy-a-Tocopherone, a Quinone Hemiacetal," Journal of the American Chemical Society 86(20):4388-4393.
Echtay, K.S. et al. (Nov. 30, 2000). "Coenzyme Q is an Obligatory Cofactor for Uncoupling Protein Function," Nature 408:609-613.
Erhola, M. et al. (Jun. 9, 1997). "Biomarker Evidence of DNA Oxidation in Lung Cancer Patients: Association of Urinary 8-Hydroxy-2'-Deoxyguanosine Excretion with Radiotherapy, Chemotherapy, and Response to Treatment," FEBS Letters 409(2):287-291.
Eurasian Search Report with English translation of third citation, received by Foreign Associate on Jul. 18, 2008, for Eurasian Patent Application No. 200702622, filed on Jun. 1, 2006, 3 pages.
European Search Report dated Jun. 10, 2009, for EP Application No. 06784530.5, filed on Jun. 1, 2006, 7 pages.
Examination Report dated Feb. 4, 2010, for EP Patent Application No. 07751472.7, filed on Oct. 8, 2009, 4 pages.
Extended European Search Report dated Apr. 14, 2011, for EP Patent Application No. 10015055.6, filed on Feb. 22, 2007, 8 pages.
Extended European Search Report dated Jun. 17, 2013, for EP Patent Application No. 13163798.5, filed on Feb. 22, 2007, 11 pages.
Extended European Search Report dated Jun. 25, 2013, for EP Patent Application No. 13163805.8, filed on Feb. 22, 2007, 13 pages.
Extended European Search Report dated May 16, 2012, for EP Patent Application No. 12162555.2, filed on Jun. 1, 2006, 7 pages.
Extended European Search Report dated Oct. 11, 2013, for EP Patent Application No. 11775506.6, filed on Apr. 26, 2011, 7 pages.
Fabrizi, G.M. et al. (Apr. 1996). "Autosomal Dominant Limb Girdle Myopathy with Ragged-Red Fibers and Cardiomyopathy: A Pedigree Study by in Vivo 31P-MR Spectroscopy Indicating a Multisystem Mitochondrial Defect," Journal of the Neurological Sciences 137(1):20-27.
Fahey J.W. et al. (2004). "The "Prochaska" Microtiter Plate Bioassay for Inducers of NQO1," Chapter 14 in Methods in Enzymology, Quinones and Quinone Enzymes, Part B, Sies H, ed., Elsevier Academic Press, San Diego, CA, pp. 243-258.
Fieser, L.F. et al. (Sep. 1942). "Alkylation of Para Quinones with Acyl Peroxides," Journal of the American Chemical Society 64(9):2060-2065.
Final Office Action dated Dec. 29, 2010, for U.S. Appl. No. 10/941,126, filed Sep. 15, 2004, 11 pages.
Final Office Action dated Feb. 25, 2015, for U.S. Appl. No. 11/445,582, filed Jun. 1, 2006, 12 pages.
Final Office Action dated Jan. 6, 2011, for U.S. Appl. No. 11/445,582, filed Jun. 1, 2006, 7 pages.
Final Office Action dated Jul. 3, 2013, for U.S. Appl. No. 12/777,179, filed May 10, 2010, 5 pages.
Final Office Action dated Oct. 19, 2011, for U.S. Appl. No. 11/710,042, filed Feb. 22, 2007, 6 pages.
Final Office Action dated Oct. 20, 2009, for U.S. Appl. No. 10/941,126, filed Sep. 15, 2004, 12 pages.
Final Office Action dated Oct. 24, 2014, for U.S. Appl. No. 13/643,542, filed Nov. 26, 2012, 6 pages.

Flynn, C.J. et al. (1989). "Ischemia and Hypoxia," Chapter 40 in Basic Neurochemistry, 4th Edition, Siegel, G.J. ed. et al., Raven Press, New York, NY, pp. 783-795.
Fryer, M.J. (1998). "Vitamin E Status and Neurodegenerative Disease," Nutritional Neuroscience 1(5):327-351.
Fujibayashi, Y. et al. (Jul. 1997). "Copper-62-ATSM: A New Hypoxia Imaging Agent with High Membrane Permeability and Low Redox Potential," The Journal of Nuclear Medicine 38(7):1155-1160.
Fujishima, T. et al. (1996, e-pub. Sep. 23, 2006). "Synthesis of Vitamin E Analogues: Possible Active Forms of Vitamin E," Arch. Pharm. Pharma. Med. Chem. 329(1):27-34.
Fukuzawa, K. et al. (Jul. 1982). "Antioxidant Activities of Tocopherols on Fe2+-ascorbate-Induced Lipid Peroxidation in Lecithin Liposomes," Lipids 17(7):511-513.
Garn, H. et al. (1994). "An improved MTT assay using the electron-coupling agent menadione," Journal of Immunological Methods 168:253-256.
Gellerich, F.N. et al. (e-pub. Jul. 7, 2008). "Impaired Regulation of Brain Mitochondria by Extramitochondrial Ca2+ in Transgenic Huntington Disease Rats," Journal of Biological Chemistry located at http://www.jbc.org.cgi/doi/10.1074/jbc.M709555200,last visited Feb. 10, 2015, 23 pages.
Gerbitz, K-D. et al. (Feb. 1996); "Mitochondria and Diabetes: Genetic, Biochemical, and Clinical Implications of the Cellular Energy Circuit," Diabetes 45(2):113-136.
Ghate, D. et al. (May 2007). "Pharmacokinetics of Intraocular Drug Delivery by Periocular Injections Using Ocular Fluorophotometry," Investigative Ophthalmology and Visual Science 48(5):2230-2237.
Gille, L. et al. (2001); "Effects of Tocopheryl Quinone on the Heart: Model Experiments with Xanthine Oxidase, Heart Mitochondria, and Isolated Perfused Rat Hearts," Free Radical Biology and Medicine 30(8):865-876.
Gille, L. et al. (2004); "Oxidized Vitamin E and Ubiquinone: Competition for Binding Sites of the Mitochondrial Cytochrome bc, Complex?" Annals of the New York Academy of Sciences 1031:341-343.
Gille, L. et al. (2004); "Redox-Interaction of a-Tocopheryl Quinone with Isolated Mitochondrial Cytochrome bci Complex," Biochemical Pharmacology 68:373-381.
Gille, L. et al. (2010); "Tocopheryl Quinones and Mitochondria," Mol. Nutr. Food Res. 54:1-15.
Goldberg, M.P. et al. (Nov. 1990). Intracellular Free Calcium Increases in Cultured Cortical Neurons Deprived of Oxygen and Glucose, Stroke 21(11-Supp III):III-75-III-77.
Gonzalez, M.J. (1990). "Serum Concentrations and Cellular Uptake of Vitamin E," Medical Hypotheses 32:107-110.
Goodhue, C.T. et al. (May 1965); "Reactions of Vitamin E with Peroxides. II. Reaction of Benzoyl Peroxide with d-o-Tocopherol in Alcohols," Biochemistry 4(5):854-858.
Gouw, L.G. et al. (May 1995); "Retinal Degeneration Characterizes a Spinocerebellar Ataxia Mapping to Chromosome 3p," Nature Genetics 10:89-93.
Grau, A. et al. (1998); "Dissimilar Protection of Tocopherol Isomers Against Membrane Hydrolysis by Phospholipase A2," Chemistry and Physics of Lipids 91:109-118.
Green, J. et al. (1966); "Bond Stabilisation in Tocopherols. Part I. The Claisen Rearrangement of Allyl Tocopheryl Ethers," Journal of the Chemical Society C pp. 1422-1427.
Gronlund M.A. et al. (2010); "Ophthalmological Findings in Children and Young Adults with Genetically Verified Mitochondrial Disease," Br. J. Ophthalmol. 94:121-127.
Grotta, J.C. et al. (1988). "Efficacy and Mechanism of Action of a Calcium Channel Blocker After Global Cerebral Ischemia in Rats," Stroke 19:447-454.
Gu et al, "Synthesis, Oxidation-Reduction Potentials and Biological Activity of 1, 4-Benzoquinone Derivatives", Youji Huaxue,1991,11(5):481-487.
Gu et al. (1990). "Effect of Substituents of the Benzoquinone Ring on Electron-Transfer Activities of Ubiquinone Derivatives," Biochimica et Biophysica Acta 1015(3):482-492.
Gu et al. (1990). "Synthesis and Inhibitory Activity of Bromoquinone Derivatives," Tetrahedron 46(9):3199-3210.

(56) References Cited

OTHER PUBLICATIONS

Gubskii et al. (2008). "Antioxidant and Membranotropic Effects of Monochromanes and Trimethylphenol Derivatives in Vitro," Ukrains'kii Biokhimichnii Zhumal 80(6):79-85, Chemical Abstract Only, CAPLUS Abstract No. 2009:267923.

Gupta et al. (Jan. 15, 2008, e-pub. Aug. 27, 2007). "Spinocerebellar Ataxia Type 7 Mimicking Kearns-Sayre Syndrome: A Clinical Diagnosis is Desirable," Journal of Neurological Sciences 264:173-176.

Haas et al. (May 2008); "The In-Depth Evaluation of Suspected Mitochondrial Disease: The Mitochondrial Medicine Society's Committee on Diagnosis," Mol. Genet. Metab. 94(1):1637, 32 pages.

Hagio, K. et al.(Apr. 1974); "Synthesis and Reactions of 4-Dimethylsulfuranylidene-2,3,-Dioxotetrahydrofuran Derivatives," Bulletin of the Chemical Society of Japan 47(4):909-916.

Han, J. (2006); "Advances in Characterization of Pharmaceutical Hydrates," Trends in Bio/Pharmaceutical Industry 3:25-29.

Hauptmann, S. et al. (2009, e-pub. Mar. 4, 2008). "Mitochondrial Dysfunction: An Early Event in Alzheimer Pathology Accumulates With Age in AD Transgenic Mice," Neurobiology of Aging 30:1574-1586.

Hawkins, R.D. et al. (1993). "Learning to Modulate Transmitter Release: Themes and Variations in Synaptic Plasticity," Annual Review of Neuroscience 16:625-665.

Hendlin, D. et al. (Apr. 1960) "The Activity of Coenzyme Qlo and Its Analogues in the Succinoxidase System of Electron Transport Particles," Journal of Biological Chemistry, 235(4):1187-1191.

Hodgkiss, R.J. et al. (May 1989); "The Effect of a-tocopherol and a-tocopheryl Quinone on the Radiosensitivity of Thiol-Depleted Mammalian Cells," International Journal of Radition Oncology, Biology, Physics 16(5):1297-1300.

Honda, M. et al. (Jun. 2000); "Correlation of Urinary 8-Hydroxy-2'-Deoxyguanosine (8-OHdG), a Biomarker of Oxidative DNA Damage, and Clinical Features of Hematological Disorders: A Pilot Study," Leukemia Research 24(6):461-468.

Huang, C.-C. et al. (Mar. 2002); "Rapid Visual Recovery After Coenzyme Q10 Treatment of Leber Hereditary Optic Neuropathy," The Journal of Neuro-Opthalmology22(1):66-67.

Hubscher, J.V. et al. (1990); Total Synthesis of Naturally Occurring a-Tocopherol. Asymmetric Alkylation and Asymmetric Epoxidation as Means to Introduce (R)-Configuration at C(2) of the Chroman Moiety, Helvetica Chimica Acta 73(4-6):1068-1086 (English Translation of Abstract Only).

Hudson, G. et al. (Jul. 2008); "Leber Hereditary Optic Neuropathy," Expert Opinion on Medical Diagnostics 2(7):789-799.

Iizuka, T. et al. (2005); "Pathogenesis of Stroke-Like Episodes in MELAS: Analysis of Neurovascular Cellular Mechanisms," Current Neurovascular Research 2(1):29-45.

Ikawa, M. et al.(2009, e-pub. Jan. 30, 2009). "PET Imaging of Redox and Energy States in Stroke-Like Episodes of MELAS," Mitochondrion 9:144-148.

Infante, J.P. (1999; "A Function for the Vitamin E Metabolite a-Tocopherol Quinone as an Essential Enzyme Cofactor for the Mitochondria! Fatty Acid Desaturases," The FEBS Letters 446:1-5.

Inoue, S. et al. (1987); "Improved General Method of Ortho Alkylation of Phenols Using Alkyl Isopropyl Sulfide, Sulfryl Chloride, and Triethylamine. An Expedient Synthesis of Representative Oxygen Heterocycles and (2R,4'R,8'R)-o-Tocopherol," Journal of Organic Chemistry 52:5495-5497.

International Preliminary Report on Patentability dated Feb. 28, 2012, for PCT Patent Application No. PCT/US2010/046503, filed on Aug. 24, 2010, 5 pages.

International Preliminary Report on Patentability dated Nov. 1, 2011, for PCT Patent Application No. PCT/US2010/032621, filed on Apr. 27, 2010, 6 pages.

International Preliminary Report on Patentability dated Nov. 1, 2011, for PCT Patent Application No. PCT/US2010/032624, filed on Apr. 27, 2010, 7 pages.

International Preliminary Report on Patentability dated Oct. 30, 2012 for PCT Patent Application No. PCT/US2011/033983 filed on Apr. 26, 2011, 6 pages.

International Search Report dated Feb. 8, 2007, for PCT Patent Application No. PCT/US2006/036052 filed on Sep. 15, 2006, 5 pages.

International Search Report Report dated Jul. 13, 2011, for PCT Patent Application No. PCT/US11/33983, filed on Apr. 26, 2011, 2 pages.

International Search Report dated Jul. 19, 2010, for PCT Patent Application No. PCT/US2010/032621, filed on Apr. 27, 2010, 4 pages.

International Search Report dated Jul. 8, 2010, for PCT Patent Application No. PCT/US2010/032624, filed on Apr. 27, 2010, 4 pages.

International Search Report dated Mar. 14, 2007, for PCT Patent Application No. PCT/US2006/021295 filed Jan. 6, 2006, 7 pages.

International Search Report dated May 30, 2008, for PCT Patent Application No. PCT/US2007/004713, filed on Feb. 22, 2007, 4 pages.

International Search Report dated Nov. 9, 2010, for PCT Patent Application No. PCT/US2010/046503, filed on Aug. 24, 2010, 4 pages.

Ito, H. et al.(2008). "Serial Brain Imaging Analysis of Stroke-Like Episodes in MELAS," Brain & Development 30:483-488.

Jaiswal, A.K. (2000). "Characterization and Partial Purification of Microsomal NAD(P)H:Quinone Oxidoreductases," Archives of Biochemistry and Biophysics 375(1):62-68.

James, A.M. et al. (Jun. 3, 2005). "Interactions of Mitochondria-Targeted and Untargeted Ubiquinones with the Mitochondrial Respiratory Chain and Reactive Oxygen Species," The Journal of Biological Chemistry 280(22):21295-21312.

Jarrett, S.G. et al. (2008). "Mitochondrial DNA Damage and Its Potential Role in Retinal Degeneration," Progress in Retinal and Eye Research 27:596-607.

Jauslin, M.L. et al. (2002). "A Cellular Model for Friedreich Ataxia Reveals Small-Molecule Glutathione Peroxidase Mimetics as Novel Treatment Strategy," Human Molecular Genetics 11(24):3055-3063.

Jauslin, M.L. et al. (Oct. 2003, e-pub. Aug. 15, 2003). "Mitochondria-Targeted Antioxidants Protect Friedreich Ataxia Fibroblasts from Endogenous Oxidative Stress more Effectively than Untargeted Antioxidants," The FASEB Journal 17(13):1972-1974.

Jiang, Q. et al. (Oct. 10, 2000). γ-Tocopherol and its Major Metabolite, in Contrast to α-Tocopherol, Inhibit Cyclooxygenase Activity in Macrophages and Epithelial Cells, Proceedings of the National Academy of Sciences 97(21):11494-11499.

Jones, J.W. et al. (1977). "10% Soybean Oil Emulsion As a Myocardial Energy Substrate After Ischemic Arrest," Surgical Forum 28:284-285.

Jung, M E et al: "First Enantioselective Total Synthesis of the Endogenous Natriuretic Agent LLU-Alpha", Tetrahedron Letters, Elsevier, Amsterdam, NL, vol. 40, No. 25, Aug. 27, 1999 (Aug. 27, 1999), pp. 6339-6342, XP004173857, ISSN: 0040-4039, DOI: 10.1016/S00404039(99)01204-6.

Jung, M.Y. et al. (Sep. 1, 1990). "Effects of α-, γ- -, and δ-Tocopherols on Oxidative Stability of Soybean Oil," Journal of Food Science 55(5), pp. 1464-1465.

Kabbe, H.J. et al. (1978). "Eine Neue Synthese von 3,4-Dehydro-a-Tocotrienol und Vitamin-E," Synthesis 888-889. (Translation of Abstract only: Chemical Abstract CAPLUS Abstract No. 1979:168774, 2 pages).

Kajiwara, M. et al. (1980). "Studies on Tocopherols 111. Convenient Synthesis of Tocopherols," Heterocycles 14(12), pp. 1995-1998.

Kamat, J.P. et al.(1995). "Tocotrienols from Palm Oil as Potent Inhibitors of Lipid Preoxidation and Protein Oxidation in Rat Brain Mitochondria," Neurosci. Lett. 195, pp. 179-182.

Kanno, T. et al. (1996). "Inhibition of Neutrophil-Superoxide Generation by α-Tocopherol and Coenzyme Q," Free Radical Research 24(4), pp. 281-289.

(56) References Cited

OTHER PUBLICATIONS

Kapinya K. et al. (2003). "Role of NAD(P)H:quinone oxidoresuctase in the progression of neuronal cell death in vitro and following cerebral ischaemia in vivo," Journal of Neurochemistry 84, pp. 1028-1039.

Kariya, S. et al.(2005, e-pub. Mar. 10, 2005). "Humanin Detected in Skeletal Muscles of MELAS Patients: A Possible New Therapeutic Agent," Acta Neuropathol. 109, pp. 367-372.

Karry, R. et al. (2004). "Mitochondria! Complex I Subunits Expression Is Altered in Schizophrenia: A Postmortem Study," Biological Psychiatry 55(7), pp. 676-684.

Kaufmann, P. et al. (Apr. 27, 2004). "Cerebral Lactic Acidosis Correlates with Neurological Impairment in MELAS," Neurology 62(8), pp. 1297-1302.

Keeney, P.M. et al. (May 10, 2006). "Parkinson's Disease Brain Mitochondrial Complex I Has Oxidatively Damaged Subunits and Is Functionally Impaired and Misassembled," The Journal of Neuroscience 26(19), pp. 5256-5264.

Kelso, G.F. et al. (Feb. 16, 2001)"Selective Targeting of a Redox-Active Ubiquinone to Mitochondria Within Cells," The Journal of Biological Chemistry 276(7), pp. 4588-4596.

Khan, S.Z. (2006). "Mitochondrial Complex-1 in Parkinson's Disease," Neurology India located at http://www.neurologyindia.com/article.asp?issn=0028-3886;year=2006;volume=54;is . . . , last visited Feb. 10, 2015.

Khanna, S. et al.(2005, e-published Sep. 15, 2005). "Neuroprotective Properties of the Natural Vitamin E α-Tocotrienol," Stroke 36:e144-e152.

Khanna, S. et al.(2014, e-published Nov. 19, 2014). "Excessive α-tocopherol exacerbates microglial activation and brain injury caused by acute ischemic stroke," The FASB Journal vol. 29, pp. 1-9.

Kim, J.Y. et al.(May 2004). "Urinary 8-Hydroxy-2'-Deoxyguanosine as a Biomarker of Oxidative DNA Damage in Workers Exposed to Fine Particulates," Environmental Health Perspectives 112(6):666-671.

Kim, S-O. et al. (Mar. 8, 2004). "KR-31378 Protects Neurons from Ischemia-Reperfusion Brain Injury by Attenuating Lipid Peroxidation and Glutathione Loss," European Journal of Pharmacology 487(1-3):81-91.

Kinouchi, H. et al. (Dec. 1991). "Attenuation of Focal Cerebral Ischemic Injury in Transgenic Mice Overexpressing CuZn Superoxide Dismutase," Proc. Natl. Acad. Sci. USA 88, pp. 11158-11162.

Kirkman, M.A. (Jul. 2009). "Quality of Life in Patients with Leber Hereditary Optic Neuropathy," Investigative Ophthalmology & Visual Science 50(7), pp. 3112-3115.

Klivenyi et al. "Alpha-Tocopherol/lipd ratio in blood is decreased in patients with Leber's hereditary optic neuropathy and asymptomatic carriers of the 11778 mtDNA mutation"; J. Neurol Neurosurg Psychiatry Mar. 2011;70(3), pp. 359-362.

Kobayashi, M.S. et al. (2000). "Antioxidants and Herbal Extracts Protech HT-4 Neuronal Cells Against Glutamate-Induced Cytotoxicity," Free Radical Research 32(2), pp. 115-124.

Kosmorsky, G. et al. (Feb. 1991). "Neuro-Opthalmologic Manifestations of Mitochondrial DNA Disorders: Chronic Progressive External Opthalmoplegia, Kearns-Sayre Syndrome, and Leber's Hereditary Optic Neuropathy," Neurologic Clinics 9(1), pp. 147-161.

Kovalenko, V.N. et al. (1979); "Vitamin E Activity of Vitamin E Derivatives in Experimental Encephalomalacia in Chicks," Ukrainskii Biokhimicheskii Zhurnal 51(6):665-668, Chemical Abstract Only, CAPLUS Abstract No. 1980:74772, 1 page.

Kumadaki et al. (1989); Trifluoromethylation of Tocopherols, Synthetic Communications 19(1&2),173-177.

Kunitsa, N.I., et al. (Nov. 1993); "Effects of Tocopherol and its Analogs on in vivo Lipid Peroxidation and Electron Transport in Rat Liver Mitochondria," Biochemistry (Moscow) An International Journal 58(11), pp. 1256-1259.

Kunz, W.S. et al.(2004); "The Role of Mitochondria in Epilepsy: Implications for Neurodegenerative Diseases," Toxicology Mechanisms and Methods 14, pp. 19-23.

Kunz, W.S. et al.(Nov. 2000); "Mitochondrial Complex I Deficiency in the Epileptic Focus of Patients with Temporal Lobe Epilepsy," Annals of Neurology 48(5), pp. 766-773.

Kwong, J.Q. et al. (2006). "The Role of Mitochondria in Inherited Neurodegenerative Diseases," Journal of Neurochemistry 97:1659-1675.

Lamson, D.W. (2002); "Mitochondrial Factors in the Pathogenesis of Diabetes: A Hypothesis for Treatment —Mitochondial Factors/Diabetes," Alternative Medicine Review 7(2):94-111.

Larisch, B. et al. (Jul. 1996). "Reactions of Dehydroascorbic Acid with Primary Aliphatic Amines Including Na-Acetyllysine," Journal of Agricultural and Food Chemistry 44(7), pp. 16301634.

Lee, P.I. (1992). "Diffusion-Controlled Matrix Systems," Chapter 3 in Treatise on Controlled Dug Delivery, Kydonieus, A. ed., Marcel Dekker, Inc., New York, NY, pp. 155-197.

Lenaz, G. et al. (2000). "Mitochondria! Bioenergetics in Aging," Biochimica et Biophysica Acta 1459, pp. 397-404.

Lewis, J.S. et al. (Apr. 2001). "Tumor Uptake of Copper-Diacetyl-Bis(N4-Methylthiosemicarbazone): Effect of Changes in Tissue Oxygenation," The Journal of Nuclear Medicine 42(4):655-661.

Li, H. et al., "CoQ10 fails to protect brain against focal and global ischemia in rats." Brain Res. Sep. 15, 2000; 877(1), pp. 7-11.

Lipshutz, B.H. et al. (Feb. 12, 1998). "An Expeditious Route to CoQ,,, Vitamins K1 and K2, and Related Allylated para-Quinones Utilizing Ni(0) Catalysis," Tetrahedron 54(7), pp. 1241-1253.

Lodi, R. et al.(2001). "Antioxidant Treatment Improves In Vivo Cardiac and Skeletal Muscle Bioenergetics in Patients with Friedreich's Ataxia," Annals of Neurology 49, pp. 590-596.

Lowell, B. (Jan. 21, 2005). "Mitochondrial Dysfunction and Type 2 Diabetes," Science 307(5708), pp. 384-387.

Lustbader, J.W. et al. (Apr. 16, 2004). "ABAD Directly Links A(to Mitochondrial Toxicity in Alzheimer's Disease," Science 304(5669):448-452.

Lynch, D.R. et al. (Jul. 2012; e-pub. Jun. 28, 2012). "A0001 in Friedreich Ataxia: Biochemical Characterization and Effects in a Clinical Trial," Mov. Disord. 27(8):1026-1033.

Lynch, D.R. et al. (May 2002). "Near Infrared Muscle Spectroscopy in Patients with Friedreich's Ataxia," Muscle & Nerve 25(5), pp. 664-673.

Mackenzie, J.B. et al. (1950). The Biological Activity of a-Tocopherylhydroquinone and a-Tocopherylquinone, Journal of Biological Chemistry 183(2):655-662.

Macmanus, J.P. et al. (1993). "Global Ischemia Can Cause DNA Fragmentation Indicative of Apoptosis in Rat Brain," Neuroscience Letters 164:89-92.

Makovetskii, V.P. et al. (1987). "Synthesis, Properties, and Detoxication Activity of a-tocopherol Analogs and Derivatives," Khimiko-Farmatsevticheskii Zhumal21(12):1441-1446, Chemical Abstract Only, CAPLUS Abstract No. 1988:142850, 2 pages.

Maloney, D.J. et al. (2005, e-pub. Aug. 20, 2005). "A Stereocontrolled Synthesis of 5-trans-Tocotri en oloic Acid," Organic Letters 7(19), pp. 4297-4300.

Man, P.Y.W. et al. (2002). "Leber Hereditary Optic Neuropathy," J. Med. Genet. 39, pp. 162-169.

Mann, V.M. et al. (1992). "Brain, Skeletal Muscle and Platelet Homogenate Mitochondrial Function in Parkinson's Disease," *Brain* 115:333-342.

MARPAT Accession No. 138:187513, 2 pages.

Matthews, P.M. et al. (Apr. 1991). "In Vivo Magnetic Resonance Spectroscopy of Brain and Muscle in a Type of Mitochondrial Encephalomyopathy (MERRF)," Annals of Neurology 29(4):435-438.

Mayer, H. et al. (1967). "Ober die Chemie des Vitamins E. 8. Mitteilung [1]. Die Stereochemie von NatOrlichem y-Tocotrienol (Plastochromanol-3), Plastochromanol-8 und Plastochromano1-81)," Helvetica Chimica Acta 50(5):1376-1393, No. 139. (English Summary on pp. 1392-1393 and Chemical Abstract CAPLUS Abstract No. 1967:473698 is also included.).

(56) References Cited

OTHER PUBLICATIONS

Mazzini, F. et al. (2005, e-pub. Nov. 30, 2004). "Easy Route to Labeled and Unlabeled R,R,R,-7-Tocopherol by Aryl Demethylation of a-Homologues," Tetrahedron 61:813-817.

Mishima, Tanaka T. et al. (2003) "Vitamin E isoforms alpha-tocotrienol and gamma-tocopherol prevent cerebral infarction in mice" Neurosci Lett; 337 (1) 56-60 DOI: http://www.ncbi.nlm.nih.gov/pubmed/12524170.

Molinari, G.F. (1986). "Experimental Models of Ischemic Stroke," Chapter 5 in Stroke, Pathophysiology, Diagnosis, and Management, vol. 1, Barnett, H.J.M. ed. et al., Churchill Livingstone Inc., pp. 57-73.

Monte, W. T. et al. (May/Jun. 2001). "An Efficient Process for the Synthesis of y-Arylbutanals via Copper-Mediated Grignard Coupling,"Organic Process Research & Development 5(3):267-269.

Moore, A.N.J. et al. (1997). "a-Tocopheryl Quinone is Converted into Vitamin E in Man," Free Radical Biology & Medicine 22(5):931-934.

Mukai et al, "Stopped-flow kinetic study of vitamin E regeneration reaction with biological hydroquinones (reduced forms of ubiquinone, vitamin K, and tocopherolquinone) in solution", J Biol Chem, Nov. 5, 1992, vol. 267, No. 31, pp. 22277-22281.

Mukai, K. et al. (1989). "Synthesis and Kinetic Study of Antioxidant Activity of New Tocopherol (Vitamin E) Compounds," The Journal of Organic Chemistry 54(3):552-556.

Mukai, K. et al. (1989). "Synthesis and Stopped-Flow Investigation of Antioxidant Activity of Tocopherols. Finding of New Tocopherol Derivatives Having the Highest Antioxidant Activity Among Phenolic Antioxidants," The Journal of Organic Chemistry 54(3):557-560.

Mukai, K. et al. (1991). "Structure-Activity Relationship in the Quenching Reaction of Singlet Oxygen by Tocopherol (Vitamin E) Derivatives and Related Phenols. Finding of Linear Correlation Between the Rates of Quenching of Singlet Oxygen and Scavenging of Peroxyl and Phenoxyl Radicals in Solution," *The Journal of Organic Chemistry*, 56(13):4188-4192.

Munnich, A. et al. (1992). "Clinical Aspects of Mitochondria! Disorders," *Journal of Inherited Metabolic Disease*, 15(4):448-455.

Myagkov, I.V. (Sep.-Oct. 1985). "Monomolecular Films of Octadecyl-Substituted Quinone and Hydroquinone and Their Charge-Transfer Complexes," *Colloid Journal of the USSR* 47(5):833-836.

Neuzil, J. et al. (Oct. 1998). "α-Tocopherol in Atherogenesis: Do We Know Its Real Role?" Cardiovascular Drugs and Therapy 12(5):421-423.

Niaudet et al. (1996). "Renal Involvement in Mitochondrial Cytopathies," Pediatric Nephrol. 10(3):368-373.

Nishigaki, Y. et al. (2003). "A Novel Mitochondrial tRNALeu(UUR) Mutation in a Patient with Features of MERRF and Kearns-Sayre Syndrome," *Neuromuscular Disorders* 13:334-340.

Non-Final Office Action dated Aug. 6, 2014, for U.S. Appl. No. 11/445,582, filed Jun. 1, 2006, 12 pages.

Non-Final Office Action dated Aug. 20, 2008, for U.S. Appl. No. 10/941,126, filed Sep. 15, 2004, 7 pages.

Non-Final Office Action dated Aug. 9, 2011, or U.S. Appl. No. 10/941,126, filed Sep. 15, 2004, 10 pages.

Non-Final Office Action dated Feb. 7, 2014, for U.S. Appl. No. 13/643,542, filed Nov. 26, 2012, 9 pages.

Non-Final Office Action dated Jan. 21, 2011, for U.S. Appl. No. 11/710,042, filed Feb. 22, 2007, 6 pages.

Non-Final Office Action dated Jun. 23, 2010, for U.S. Appl. No. 11/445,582, filed Jun. 1, 2006, 12 pages.

Non-Final Office Action dated Jun. 30, 2010, for U.S. Appl. No. 10/941,126, filed Sep. 15, 2004, 8 pages.

Non-Final Office Action dated Mar. 17, 2010, for U.S. Appl. No. 10/941,126, filed Sep. 15, 2004, 6 pages.

Non-Final Office Action dated Mar. 31, 2009, for U.S. Appl. No. 10/941,126, filed Sep. 15, 2004, 14 pages.

Non-Final Office Action dated Oct. 26, 2012, for U.S. Appl. No. 12/777,179, filed May 10, 2010, 5 pages.

Obata, A. et al. (2001). "Retention Mechanism of Hypoxia Selective Nuclear Imaging/Radiotherapeutic Agent Cu-diacetyl-bis(N4-Methylthiosemicarbazone) (Cu-ATSM) in Tumor Cells," Annals of Nuclear Medicine 15(6):499-504.

Obón J. et al. (1999). "Enzymatic cycling assay for D-carnitine determination," Anal Biochem. 274(1):34-9.

Olichon, A. et al.(2006, e-pub. Apr. 20, 2006). "Mitochondrial Dynamics and Disease, OPA1," Biochimica et Biophysica Acta 1763:500-509.

Oliveira, J.M.A. et al. (2007). "Mitochondrial Dysfunction in Huntington's Disease: The Bioenergetics of Isolated and in situ Mitochondria from Transgenic Mice," Journal of Neurochemistry 101(1):241-249.

Omura, K. (1989). "Iodine Oxidation of a-Tocopherol and Its Model Compound in Alkaline Methanol: Unexpected Isomerization of the Product Quinone Monoketals," The Journal of Organic Chemistry 54(8):1987-1990.

Orbis. (2003). "Chronic Progressive External Opthalmoplegia," located at http://telemedicine.orbis.orgibins/volume_page.asp?cid=1-2896-5258-5381&print=true, last visited on Jun. 10, 2014, 1 page.

Packer, L. et al. (2001). "Symposium: Molecular Mechanisms of Protective Effects of Vitamin E in Atherosclerosis, Molecular Aspects of a-Tocotrienol Antioxidant Action and Cell Signalling," The Journal of Nutrition 131:369S-373S.

Pagliacci, M.C. et al. (1993). "Genistein Inhibits Tumor Cell Growth in vitro but Enhances Mitochondrial Reduction of Tetrazolium Salts: A Further Pitfall in the Use of the MTT Assay for Evaluating Cell Growth and Survival," Eur J. Cancer 29A(11):1573-1577.

Paranich, A.V. et al. (1991). "Age-Related Tocopherol Content of Normal and Ischemic Heart and Liver of Rats," Fiziologicheskii Zhurnal (Kiev, 1978-1993) 37(5):16-19. (English Abstract only).

Park, L.C.H. et al. (2000). "Metabolic Impairment Elicits Brain Cell Type-Selective Changes in Oxidative Stress and Cell Death in Culture," Journal of Neurochemistry 74(1):114-124.

Patani et al, "Bioisosterism: A Rational Approach in Drug Design," Chemical Reviews, Dec. 1996, vol. 19, No. 8, pp. 3147-3176.

Pearce, B.C. et al.(1992). "Hypocholesterolemic Activity of Synthetic and Natural Tocotrienols," Journal of Medicinal Chemistry 35(20):3595-3606.

Pelak, V.S. et al. (Sep. 2004). "Neuro-Ophthalmic Manifestations of Neurodegenerative Disease," Ophthalmology Clinics of North America 17(3):311-320.

Pelter, A. et al.(1993). "Phenolic Oxidations with Phenyliodonium Diacetate," Journal of the Chemical Society, Perkin Transactions 1 16:1891-1896.

Pelter, A. et al. (1997). "The Synthesis of 8a-Methoxy-2H,6H-Chromen-6-ones and Corresponding 2H-Chromenes by a Unique Process Utilising Phenolic Oxidation," Tetrahedron 53(11):3879-3916.

Pileni, M.P. et al. (1980). "Zinc Porphyrin Sensitized Reduction of Simple and Functional Quinones in Micellar Systems," Journal of Physical Chemistry 84(14):1822-1825.

Pileni, M-P. et al. (Apr. 15, 1980). "Zinc-Porphyrin Sensitized Reduction of Simple and Functional Quinones in Vesicle Systems," Chemical Physics Letters 71(2):317-321.

Pilger, A. et al. (Sep. 2001). "Longitudinal Study of Urinary 8-Hydroxy-2'-Deoxyguanosine Excretion in Healthy Adults," Free Radical Research 35(3):273-280.

Pima, I.L. et al. (Mar. 4, 2003). "Exercise and Heart Failure: A Statement From the American Heart Association Committee on Exercise, Rehabilitation, and Prevention," Circulation 107(8):1210-1225.

Prochaska H.J. et al. (1988). "Direct measurement of NAD(P)H:quinone reductase from cells cultured in microtiter wells: a screening assay for anticarcinogenic enzyme inducers," Anal. Biochem. 169:328-36.

Pulsinelli, W.A. (2000). "Ischemic Cerebrovascular Disease," Chapter 470 and "Hemorrhagic Cerebrovascular Disease," Chapter

(56) References Cited

OTHER PUBLICATIONS 471 in Cecil Textbook of Medicine, 21ST Edition, Goldman, L. ed. et al., W.B. Saunders Company: Philadelphia, PA, pp. 2099-2115.
Qureshi, A.A. et al. (2001). "Novel Tocotrienols of Rice Bran Inhibit Atherosclerotic Lesions in C57BL/6 ApoE-Deficient Mice," Journal of Nutrition 131:2606-2618.
Raghava et al. (2004) "Periocular Routes for Retinal Drug Delivery," *Expert Opin. Drug Deliv.* 1(1):99-114.
Ricciarelli, R. et al. (1998). "α-Tocopherol Specifically Inactivates Cellular Protein Kinase C α by Changing Its Phosphorylation State," Biochem. J. 334:243-249.
Richards, R.M.E. (2004). "Ophthalmic Products," Chapter 26 in *Pharmaceutical Practice*, Third Edition, Winfield, A.J. et al. eds., Churchill Livingstone, pp. 264-279.
Riss T. et al (2013). "Cell viability Assays," Assays Guidance Manual, 28 pages.
Rolfe, P. (2000), "In Vivo Near-Infrared Spectroscopy," *Annual Review of Biomedical Engineering* 2:715-754.
Russo, R. et al. (2008). "Rational Basis for the Development of Coenzyme Q10 as a Neurotherapeutic Agent for Retinal Protection," Progress in Brain Research 173:575-582.
Sakamoto et al. "Role of the Isoprenyl Tail of Ubiquinone in Reaction with Respiratory Enzymes: Studies with Bovine Heart Mitochondrial Complex I and *Escherichia coli* bo-Type Ubiquinol Oxidase", *Biochemistry*, 1998, vol. 37, pp. 15106-15113.
Saldeen, T. et al. (Oct. 1999). "Differential Effects of α- and γ-Tocopherol on Low-Density Lipoprotein Oxidation, Superoxide Activity, Platelet Aggregation and Arterial Thrombogenesis," Journal of the American College of Cardiology 34(4):1208-1215.
Schudel, P. et al. (1963). Uber die Chemie des Vitamins E. 5. Mitteilung. Die Synthese von rac. all-trans-0- and-E-Tocopherol, Helvetica Chimica Acta 46(7):2517-2526. (English summary on p. 2526.).
Scott, J.W. et al. (1976). "Syntheses of (2R,4'R,8'R)-a-Tocopherol and (2R,3'E,7'E)-a-Tocotrienol," *Helvetica Chimica Acta* 59:290-306, Nr. 34.
Sen, C.K. et al. (2007). "Tocotrienols in Health and Disease: The Other Half of the Natural Vitamin E Family," Mol. Aspects Med. 28(5-6):692-728.
Sen, C.K. et al. (Apr. 28, 2000); "Molecular Basis of Vitamin E Action. Tocotrienol Potently Inhibits Glutamate-Induced pp60c-Src Kinase Activation and Death of HT4 Neuronal Cells," The Journal of Biological Chemistry 275(17):13049-13055.
Shi et al. (1996). "Hydrophobic Acceleration of Electron Transfer Processes," *Journal of Organic Chemistry* 61(14):4698-4702.
Shiraishi, M. et al. (Sep. 1989); "Quinones. 4. Novel Eicosanoid Antagonists: Synthesis and Pharmacological Evaluation," Journal of Medicinal Chemistry 32(9):2214-2221.
Siegel et al. (1997); The Reduction of a-Tocopherolquinone by Human NAD(P)H: Quinone Oxidoreductase: The Role of a-Tocopherolhydroquinone as a Cellular Antioxidant, Molecular Pharmacology 53:300-305.
Silbert et al. (1996); "The "S" in MELAS," Journal of Stroke and Cerebrovascular Diseases 6(2):67-71.
Silbert et al. (Jun. 2, 1959); "Peroxides. VI. Preparation of t-Butyl Peresters and Diacyl Peroxides of Aliphatic Monobasic Acids," Journal of the American Chemical Society 81(10): 2364-2367.
Soll, H-J. et al. (Aug. 1-6, 1983). "Inhibitor Binding and Displacement in Plastoquinone Depleted Chloroplasts," Advances in Photosynthesis Research, Proceedings of the International Congress of Photosynthesis, Brussels, Belgium 4:5-8.
Spoyalov, A.P. et al. (1992). "ENDOR and ESEEM Studies of Ion Radicals of Artificial Dimethoxy- or Halogen-1,4-benzoquinones with an Alkyl Side Chain of Differing Length," Journal of the Chemical Society, Perkin Transactions 2, pp. 1519-1524.
Staniek, K. et al. (Nov. 1, 2005). "The Protection of Bioenergetic Functions in Mitochondria by New Synthetic Chromanols," Biochemical Pharmacology 70(9):1361-1370.
Stella, V.J. et al. (2007). "Prodrugs: Challenges and Rewards, Part I," Biotechnology: Pharmaceutical Aspects 1(1):24.

STN Accession No. 1985:621368, last visited Jan. 23, 2007,1 page.
STN Accession No. 1992:58878, last visited Jan. 23, 2007, 1 page.
STN Accession No. 1993:21870, last visited Jan. 23, 2007, 2 pages.
Strangman, G. et al. (Oct. 1, 2002). "Non-Invasive Neuroimaging Using Near-Infrared Light," Biological Psychiatry 52(7):679-693.
Strohschein, S. et al., (Jan. 1, 1998). "Shape Selectivity of C30 Phases for RP-HPLC Separation of Tocopherol Isomers and Correlation with MAS NMR Data from Suspended Stationary Phases," Analytical Chemistry 70(1):13-18.
Tabrizi, S.J. et al.(Jul. 1998). "Primary and Secondary Deficiencies of the Mitochondrial Respiratory Chain," The Neurologist 4(4):169-179.
Taivassalo, T. et al. (Feb. 2003). "The Spectrum of Exercise Tolerance in Mitochondrial Myopathies: A Study of 40 Patients," Brain 126(Pt2):413-423.
Taivassalo, T. et al. (Jan. 2002, e-pub. Nov. 15, 2001). "Venous Oxygen Levels During Aerobic Forearm Exercise: An Index of Impaired Oxidative Metabolism in Mitochondria! Myopathy," Annals of Neurology. 51(1):38-44.
Tanito, M. et al.(May 2004). "Distribution of Tocopherols and Tocotrienols to Rat Ocular Tissues After Topical Ophthalmic Administration," Lipids 39(5):469-474.
Testai, F.D. et al. (2010). "Inherited Metabolic Disorders and Stroke Part 1," Arch. Neurol. 67(1):19-24.
Theriault, A. et al. (Jul. 1999). "Tocotrienol: A Review of Its Therapeutic Potential," Clinical Biochemistry 32(5):309-319.
Thom S.M. et al.(1993). "Factors affecting the selection and use of tetrazolium salts as cytochemical indicators of microbial viability and activity," J. Appl. Bacteriol 74(4):433-43.
Thomas, A.D. et al. (Aug. 8, 1986). "Repetitive Diels-Alder Reactions for the Growth of Linear Polyacenequinoid Derivatives," Journal of Organic Chemistry 51(22):4160-4169.
Tietjen, G.E. (1996). "Stroke in MELAS," Journal of Stroke and Cerebrovascular Diseases 6(2):59-60.
Timochko, M.F. et al. (1998). "Metabolic Aspects of Oxygen Homeostasis Formation Under Extreme Conditions," with English translation of paragraph 5 on p. 7, L'vov, located at <http://posrednik.ru/tren/tim_sv.htm>, last visited on Sep. 29, 2008, 52 pages.
Trumpower, B.L. (Jul. 15, 1990). "The Protonmotive Q Cycle. Energy Transduction by Coupling of Proton Translocation to Electron Transfer by Cytochrome bci Complex," The Journal of Biological Chemistry 265(20):11409-11412.
Tsuchiya, K. et al. (1999). "MELAS with Prominent White Matter Gliosis and Atrophy of the Cerebellar Granular Layer: A Clinical, Genetic, and Pathological Study," Acta Neuropathol. 97:520-524.
Ueda, K. et al. (Feb. 1997). "Evaluation of Changes in Hepatic Energy Metabolism during Exercise by Ketone Body Ration in Humans," Journal of Cardiology 29(2):95-102 (English Translation of Abstract Only).
Urano, S. et al. (1983). "Synthesis of dl-a-Tocopherol and dl-a-Tocotrienol," Chem. Pharm. Bull. 31(12):4341-4345.
Van Beekvelt, M.C.P. et al. (Oct. 1999). "Quantivative Near-Infared Spectroscopy Discriminates Between Mitochondrial Myopathies and Normal Muscle," Annals of Neurology 46(4):667-670.
Van Haaften, R.I.M. et al. (Mar. 15, 2001). "No Reduction of a-Tocopherol Quinone by Glutathione in Rat Liver Microsomes," Biochemical Pharmacology 61(6):715-719.
Vatassery, G. et al. (Apr. 5, 2004). "Iron Uncouples Oxidative Phosphorylation in Brain Mitochondria Isolated From Vitamin E-Deficient Rats," Biochimica et Biophysica Acta 1688(3):265-273.
Vippagunta, S.R. et al. (2001). "Crystalline Solids," Advanced Drug Delivery Reviews 48:3-26.
Wakakura, M. et al. (2009). "Initial Temporal Field Defect in Leber Hereditary Optic Neuropathy," Jpn. J. Ophthalmol. 53:603-607.
Walter, L. et al. (Sep. 22, 2000). "Three Classes of Ubiquinone Analogs Regulate the Mitochondrial Permeability Transition Pore Through a Common Site," The Journal of Biological Chemistry 275(38):29521-29527.
Wang, J-F.(Dec. 2007). "Defects of Mitochondrial Electron Transport Chain in Bipolar Disorder: Implications for Mood-Stabilizxing Treatment," *The Canadian Journal of Psychiatry* 52(12):753-762.

(56) References Cited

OTHER PUBLICATIONS

Warner, S.A. et al. (May 1, 1983). "Synthesis and Metabolism of a-Tocopherol Quinone in Normal and Diabetic Mouse Liver," Federation Proceedings, American Society of Biological Chemists, 74th Annual Meeting, San Francisco, CA, Jun. 5-9, 1983, 42(7):1919, Abstract No. 944.
Watson, B.D. et al. (1989). "Ischemic Injury in the Brain. Role of Oxygen Radical-Mediated Processes," Annals. New York Academy of Sciences 559:269-281.
Wechter, W.J. et al. (Jun. 1996). "A New Endogenous Natriuretic Factor: LLU-α," Proc. Natl. Acad. Sci. USA 93:6002-6007.
Weichet J. et al. "New Substituted Benzohydroquinones", Chemical Abstracts Service, Columbus, Ohio, US; Database CA, XP002698443, retrieved from STN Database accession No. 1968:95542.
Weichet, J. et al. (1996). "Vitamin K and Vitamin E Series. XVIII. Synthesis of New Analogs of Vitamin E and Their Derivatives," *Collection of Czeckoslov. Chem. Commun.* 31:4598-4609.
Witting P K et al.: "A Rapid and Simple Screeing Test for Potential Inhibitors of Tocopherol-Mediated Peroxidation of LDL Lipids", Journal of Lipid Research, American Society for Biochemistry and Molecular Biology, Inc, US, vol. 27, No. 4, Jan. 1, 1996, pp. 853-857, XP001095707, ISSN: 0022-2275.
Written Opinion dated Feb. 8, 2007, for PCT Patent Application No. PCT/US2006/036052 filed on Sep. 15, 2006, 10 pages.
Written Opinion dated Jul. 13, 2011, for PCT Patent Application No. PCT/US11/33983, filed on Apr. 26, 2011, five pages.
Written Opinion dated Jul. 19, 2010, for PCT Patent Application No. PCT/US2010/032621, filed on Apr. 27, 2010, five pages.
Written Opinion dated Jul. 8, 2010, for PCT Patent Application No. PCT/US2010/032624, filed on Apr. 27, 2010, six pages.
Written Opinion dated Mar. 14, 2007, for PCT Patent Application No. PCT/US2006/021295 filed on Jan. 6, 2006, 9 pages.
Written Opinion dated May 30, 2008, for PCT Patent Application No. PCT/US2007/004713, filed on Feb. 22, 2007, 10 pages.
Written Opinion dated Nov. 9, 2010, for PCT Patent Application No. PCT/US2010/046503, filed on Aug. 24, 2010, 4 pages.
Wrobel, S. (Apr. 7, 2008). "Mitochondria Play Role in Pathogenesis of Alzheimer's Disease and Estrogen-Induced Neuroprotection," Experimental Biology located at http://www.medicalnewstoday.com/releases/102971.php, last visited Feb. 10, 2015, two pages.
Yamauchi, R. et al.(1990). "Reaction of 5-Tocopherol with an Alkylperoxyl Radical," Agricultural and Biological Chemistry 54(11):2993-2999.
Yamauchi, R. et al. (1990). "Reaction Products of y-Tochopherol with an Alkylperoxyl Radical in Benzene," Agricultural and Biological Chemistry 54(10):2703-2709.
Yamauchi, R. et al. (1996). "Oxidation of a-Tocopherol during the Peroxidation of Dilinoleoylphosphatidylcholine in Liposomes," Bioscience, Biotechnology, and Biochemistry 60(4):616-620.
Yang, S.-G. et al. (Dec. 2010, e-pub. Oct. 7, 2010). "Alpha-Tocopherol Quinone Inhibits Beta-Amyloid Aggregation and Cytotoxicity, Disaggregates Preformed Fibrils and Decreases the Production of Reactive Oxygen Species, NO and Inflammatory Cytokines," Neurochemistry International 57(8):914-922.
Yen, M-Y.et al.(2006); "Leber's Hereditary Optic Neuropathy: A Multifactorial Disease," *Progress in Retinal and Eye Research* 25:381-396.
Yim, S. et al. (2005); "A Continuous Spectrophotometric Assay for NADPH-cytochrome P450 Reductase Activity Using 3-(4,5-Dimethylthiazol-2-yl)-2,5-diphenyltetrazolium Bromide," Journal of Biochemistry and Molecular Biology 38(3):366-369.
Yu-Wai-Man, P. et al. (2009, e-pub. Nov. 17, 2008). "Inherited Mitochondrial Optic Neuropathies", *J. Med. Genet.* 46:145-158.
Zanna, C. et al. (2008); "OPA1 Mutations Associated with Dominant Optic Atrophy Impair Oxidative Phosphorylation and Mitochondrial Fusion," Brain 131(2):352-367.
Zheng, A. et al. (1999); "A Redox-Sensitive Resin Linker for the Solid Phase Synthesis of C-Terminal Modified Peptides," Journal of Organic Chemistry 64:156-161.
Zwaiyed, F.R. et al. (2003); "Antihypoxic Effect of Vitamin E and a Derivative Thereof in a Rat Model of Hypoxic States of Different Origins," Ukrainskii Biokhimicheskii Zhumal 75(2):6771. (English translation).
Zwaiyed, F.R. et al. (2003); Vitamin E and its Derivative Antihypoxic Effectivity in Rats Under Modeling of Hypoxic Conditions of Different Origin, *Ukrainskii Biokhimicheskii Zhumal* 75(2):67-71.
Anderson et al. "No evidence for altered muscle mitochondrial function in Parkinson's disease," *Journal of Neurology, Neurosurgery, and Psychiatry*, 1993, vol. 56, pp. 477-480.
Anonymous, "Leigh Syndrome", NORD, located at http://rarediseases.org/rare-diseases/leigh-syndrome, the site was last visited on May 12, 2016, 14 pages.
Anonymous, ICD-10 Version: 2015, "Other specified degenerative diseases of nervous system" located at http://apps.who.int/classifications/icd10/browse/2015/en#/G31.8, the site was last visited on May 12, 2016, 1 page.
Anonymous, Leigh syndrome—Genetics Home Reference, "Other Names for This Condition" located at https://ghr.nlm.nih.gov/condition/leigh-syndrome, the site was last visited on May 12, 2016, 8 pages.
Ansell et al. "The Pharmacology and Management of the Vitamin K Antagonists," Chest, 126(3), Supplement pp. 204S-233S, 2004.
Bertalan et al. (2000). "Recovery of fatty oil from the Transylvanian black current by means of supercritical and conventional extraction, "*Olaf, szappn Kozmetika* 49(Kulonszam), pp. 40-45.
Finsterer, "Leigh and Leigh-Like Syndrome in Children and Adults", *Pediatric Neurology*, 2008, vol. 39, No. 4, pp. 223-235.
Hodgkiss et al., (May 1989). "The Effect of α-tocopherol and α-tocopheryl quinone on the Radiosensitivity of Thiol-Depleted Mammalian Cells," International Journal of Radiation Oncology, Biology, Physics 16(5);1297-1300.
Korizis et al., (2001). "Determination of Malondialdehyde by Capillary Electrophoresis, Application to Human Plasma and Relation of its Levels with Prematurity," Biomedical Chromatography 15:287-291.
Munnich et al. (1992). "Clinical Aspects of Mitochondrial Disorders," Journal of Inherited Metabolic Disease 15(4):448-455.
Myagkov, "Monomolecular Films of Octadecyl-Substituted Quinone and Hydroquinone and their Charge Transfer Complexes," *Colloid Journal of the USSR, Russian Original*, 1985, vol. 47, No. 5, pp. 833-836.
Ogawa et al. (Jul. 2008). Free Radical Research, vol. 42(7), pp. 674-687.
Pearce et al., (1994). "Inhibitors of Cholesterol Biosynthesis. 2. Hypocholesterolemic and Antioxidant Activities of Benzopyran and Tetrahydronaphthalene Analogues of the Tocotrienols," Journal of Medicinal Chemistry 37(4):526-541.
Siesjö, (1981). "Cell Damage in the Brain: A Speculative Synthesis," Journal of Cerebral Blood Flow and Metabolism 1(2):155-185.
Sue et al. "Mitochondria Respirtory Chain Diseases and Mutations in Nuclear DNA: A promising Start?" *Brain Pathalogy*, 2000, vol. 10, pp. 442-450.
Wakakura et al. (2009). "Initial Temporal Field Defect in Leber Hereditary Optic Neuropathy," *Jpn. J. Ophthalmol.* 53:603-607.

SIDE-CHAIN VARIANTS OF REDOX-ACTIVE THERAPEUTICS FOR TREATMENT OF MITOCHONDRIAL DISEASES AND OTHER CONDITIONS AND MODULATION OF ENERGY BIOMARKERS

CROSS REFERENCE TO RELATED APPLICATIONS

This application is a continuation of U. S. Nonprovisional Application Ser. No. 11/710,042 filed on Feb. 22, 2007, now U.S. Pat. No. 9,278,085, which claims the benefit of U.S. Provisional Application No. 60/873,395 filed Dec. 6, 2006 and U.S. Provisional Application No. 60/776,028 filed on Feb. 22, 2006; the contents of which are incorporated herein by reference in their entireties.

TECHNICAL FIELD

The application discloses compositions and methods useful for treatment or suppression of diseases due to mitochondrial disorders, such as Friedreich's ataxia, Leber's Hereditary Optic Neuropathy, Kearns-Sayre Syndrome, and mitochondrial myopathy, encephalopathy, lactacidosis, stroke, and for modulating energy biomarkers in a subject.

BACKGROUND

Mitochondria are organelles in eukaryotic cells, popularly referred to as the "powerhouse" of the cell. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Kreb's cycle), which generates reduced nicotinamide adenine dinucleotide (NADH+H$^+$) from oxidized nicotinamide adenine dinucleotide (NAD$^+$), and oxidative phosphorylation, during which NADH+H$^+$ is oxidized back to NAD$^+$. (The citric acid cycle also reduces flavin adenine dinucleotide, or FAD, to FADH$_2$; FADH$_2$ also participates in oxidative phosphorylation.)

The electrons released by oxidation of NADH+H$^+$ are shuttled down a series of protein complexes (Complex I, Complex II, Complex III, and Complex IV) known as the respiratory chain. These complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

The citric acid cycle and oxidative phosphorylation are preceded by glycolysis, in which a molecule of glucose is broken down into two molecules of pyruvate, with net generation of two molecules of ATP per molecule of glucose. The pyruvate molecules then enter the mitochondria, where they are completely oxidized to $CO_2$ and $H_2O$ via oxidative phosphorylation (the overall process is known as aerobic respiration). The complete oxidation of the two pyruvate molecules to carbon dioxide and water yields about at least 28-29 molecules of ATP, in addition to the 2 molecules of ATP generated by transforming glucose into two pyruvate molecules. If oxygen is not available, the pyruvate molecule does not enter the mitochondria, but rather is converted to lactate, in the process of anaerobic respiration.

The overall net yield per molecule of glucose is thus approximately at least 30-31 ATP molecules. ATP is used to power, directly or indirectly, almost every other biochemical reaction in the cell. Thus, the extra (approximately) at least 28 or 29 molecules of ATP contributed by oxidative phosphorylation during aerobic respiration are critical to the proper functioning of the cell. Lack of oxygen prevents aerobic respiration and will result in eventual death of almost all aerobic organisms; a few organisms, such as yeast, are able to survive using either aerobic or anaerobic respiration.

When cells in an organism are temporarily deprived of oxygen, anaerobic respiration is utilized until oxygen again becomes available or the cell dies. The pyruvate generated during glycolysis is converted to lactate during anaerobic respiration. The buildup of lactic acid is believed to be responsible for muscle fatigue during intense periods of activity, when oxygen cannot be supplied to the muscle cells. When oxygen again becomes available, the lactate is converted back into pyruvate for use in oxidative phosphorylation.

Genetic defects in the proteins making up the respiratory chain lead to severe disease states. One such disease is Friedreich's ataxia (FRDA or FA). Friedreich's ataxia is an autosomal recessive neurodegenerative and cardiodegenerative disorder caused by decreased levels of the protein frataxin. Frataxin is important for the assembly of iron-sulfur clusters in mitochondrial respiratory-chain complexes. Estimates of the prevalence of FRDA in the United States range from 1 in every 22,000-29,000 people to 1 in 50,000 people. The disease causes the progressive loss of voluntary motor coordination (ataxia) and cardiac complications. Symptoms typically begin in childhood, and the disease progressively worsens as the patient grows older; patients eventually become wheelchair-bound due to motor disabilities.

Another disease linked to mitochondrial dysfunction is Leber's Hereditary Optic Neuropathy (LHON). The disease is characterized by blindness which occurs on average between 27 and 34 years of age; blindness can develop in both eyes simultaneously, or sequentially (one eye will develop blindness, followed by the other eye two months later on average). Other symptoms may also occur, such as cardiac abnormalities and neurological complications.

Yet another devastating syndrome resulting from mitochondrial defects is mitochondrial myopathy, encephalopathy, lactacidosis, and stroke (MELAS). The disease can manifest itself in infants, children, or young adults. Strokes, accompanied by vomiting and seizures, are one of the most serious symptoms; it is postulated that the metabolic impairment of mitochondria in certain areas of the brain is responsible for cell death and neurological lesions, rather than the impairment of blood flow as occurs in ischemic stroke. Other severe complications, including neurological symptoms, are often present, and elevated levels of lactic acid in the blood occur.

Another mitochondrial disease is Kearns-Sayre Syndrome (KSS). KSS is characterized by a triad of features including: (1) typical onset in persons younger than age 20 years; (2) chronic, progressive, external ophthalmoplegia; and (3) pigmentary degeneration of the retina. In addition, KSS may include cardiac conduction defects, cerebellar ataxia, and raised cerebrospinal fluid (CSF) protein levels (e.g., >100 mg/dL). Additional features associated with KSS may include myopathy, dystonia, endocrine abnormalities (e.g., diabetes, growth retardation or short stature, and hypoparathyroidism), bilateral sensorineural deafness, dementia, cataracts, and proximal renal tubular acidosis. Thus, KSS may affect many organ systems.

The four diseases above appear to be caused by defects in complex I of the respiratory chain. Electron transfer from complex I to the remainder of the respiratory chain is mediated by the compound coenzyme Q (also known as ubiquinone). Oxidized coenzyme Q ($CoQ^{ox}$ or ubiquinone) is reduced by complex I to reduced coenzyme Q ($CoQ^{red}$ or ubiquinol). The reduced coenzyme Q then transfers its electrons to complex III of the respiratory chain (skipping over complex II), where it is re-oxidized to $CoQ^{ox}$ (ubiquinone). $CoQ^{ox}$ can then participate in further iterations of electron transfer.

Very few treatments are available for patients suffering from these diseases. Recently, the compound idebenone has been proposed for treatment of Friedreich's ataxia. While the clinical effects of idebenone have been relatively modest, the complications of mitochondrial diseases can be so severe that even marginally useful therapies are preferable to the untreated course of the disease. Another compound, MitoQ, has been proposed for treating mitochondrial disorders (see U.S. Patent Application Publication No. 2005/0043553); clinical results for MitoQ have not yet been reported. For KSS, administration of coenzyme Q10 (CoQ10) and vitamin supplements have shown only transient beneficial effects in individual cases.

Accordingly, there is a serious and unmet need for effective treatments of mitochondrial disorders, such as Friedreich's ataxia, Leber's hereditary optic neuropathy, MELAS, and Kearns-Sayre Syndrome.

The ability to adjust biological production of energy has applications beyond the diseases described above. Various other disorders can result in suboptimal levels of energy biomarkers (sometimes also referred to as indicators of energetic function), such as ATP levels. Treatments for these disorders are also needed, in order to modulate one or more energy biomarkers to improve the health of the patient. In other applications, it can be desirable to modulate certain energy biomarkers away from their normal values in an individual that is not suffering from disease. For example, if an individual is undergoing an extremely strenuous undertaking, it can be desirable to raise the level of ATP in that individual.

DISCLOSURE OF THE INVENTION

The invention embraces methods of treating a mitochondrial disorder, modulating one or more energy biomarkers, normalizing one or more energy biomarkers, or enhancing one or more energy biomarkers, comprising administering to a subject a therapeutically effective amount or effective amount of one or more compounds as described herein. The invention also embraces compounds as described herein, which are useful for treating a mitochondrial disorder, modulating one or more energy biomarkers, normalizing one or more energy biomarkers, or enhancing one or more energy biomarkers.

In one embodiment, the invention embraces a method of treating a mitochondrial disorder, modulating one or more energy biomarkers, normalizing one or more energy biomarkers, or enhancing one or more energy biomarkers, comprising administering to a subject a therapeutically effective amount or effective amount of one or more compounds of the formula:

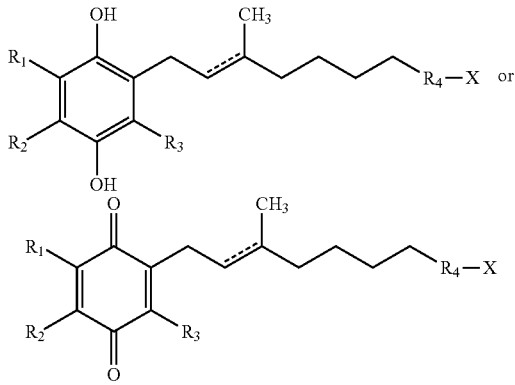

wherein the bond indicated with a dashed line can be single or double;

where $R_1$, $R_2$, and $R_3$ are independently selected from the group consisting of —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl, —O—$R_5$, —S—$R_5$, —CN, —F, —Cl, —Br, —I, —$N_3$, and —$NR_5R_6$; where $R_5$ and $R_6$ are independently selected from the group consisting of —H, —$C_1$-$C_5$ alkyl, —$C_3$-$C_6$ cycloalkyl, —$C_1$-$C_5$ haloalkyl, aryl, heteroaryl, —(C=O)—$C_0$-$C_8$ alkyl, and —(C=O)—$C_0$-$C_8$ alkyl-$C_6$-$C_{10}$ aryl-$C_0$-$C_8$ alkyl, or where $R_5$ and $R_6$ selected from these groups are combined to form a ring;

where $R_4$ represents a linear or branched group containing 1 to 32 carbon atoms and any number of single, double, or triple bonds in any chemically possible combination;

where X is selected from the group consisting of —H, —F, —Cl, —Br, —I, —CN, —$N_3$, —$NR_7R_8$, and —$OR_9$;

where $R_7$ and $R_8$ are independently selected from —H, —$C_1$-$C_8$ alkyl or —$C_1$-$C_8$ haloalkyl, —(C=O)—$C_1$-$C_8$ alkyl, or where either one of $R_7$ and $R_8$ are independently selected from the group consisting of —(C=O)—$C_1$-$C_8$ haloalkyl, —(C=O)—$NH_2$, —(C=O)—$NHC_1$-$C_8$ alkyl, —(C=O)—$NHC_1$-$C_8$ haloalkyl, —(C=O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_{20}$ and $R_{21}$ and the nitrogen atom to which they are attached, —(C=O)—$OC_1$-$C_8$ alkyl, —(C=O)—$OC_1$-$C_8$ haloalkyl, —$S(O)_2C_1$-$C_8$ alkyl, —$S(O)_2$ aryl, and —$S(O)_2$ aralkyl, and where the other of $R_7$ or $R_8$ is —H, —$C_1$-$C_8$ alkyl or —$C_1$-$C_8$ haloalkyl or where $R_7$ and $R_8$ selected from these groups are combined to form a ring, or where $R_7$ is —$(CH_2)_p$—, $R_8$ is —$(CH_2)_q$—, p and q are independently integers between 0 and 7 inclusive, p+q is between 2 and 7 inclusive, $R_7$ and $R_8$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_7$ and $R_8$ and the nitrogen atom to which they are attached;

where $R_9$ is independently selected from —H, —$C_1$-$C_8$ alkyl or —$C_1$-$C_8$ haloalkyl, —(C=O)—$C_1$-$C_8$ alkyl, —(C=O)—$C_1$-$C_8$ haloalkyl, —(C=O)—$NH_2$, —(C=O)—NH$C_1$-$C_8$ alkyl, —(C=O)—NH$C_1$-$C_8$ haloalkyl, —(C=O)—$NR_{20}R_{21}$ where $R_{20}$ is —(CH2)$_p$—, $R_{21}$ is —(CH2)$_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_{20}$ and $R_{21}$ and the nitrogen atom to which they are attached, —(C=O)—O$C_1$-$C_8$ alkyl, —(C=O)—O$C_1$-$C_8$ haloalkyl, —S(O)$_2$$C_1$-$C_8$ alkyl, —S(O)$_2$ aryl, and —S(O)$_2$;

with the proviso that when both of $R_1$ and $R_2$ are —OMe and $R_3$ is -Me, then X is not —H or —OH;

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, $R_1$, $R_2$, and $R_3$ are independently selected from the group consisting of —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl, —S—$R_5$, —CN, —F, —Cl, —Br, —I, —$N_3$, and —$NR_5R_6$. In another embodiment, $R_1$, $R_2$, and $R_3$ are independently selected from —H —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl. In another embodiment, at least one of $R_1$, $R_2$, and $R_3$ is independently selected from —$C_2$-$C_5$ alkyl, —$C_2$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl. In another embodiment, at least one of $R_1$, $R_2$, and $R_3$ is independently selected from —$C_2$-$C_5$ alkyl, —$C_2$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl, with the proviso that X is not —H. In another embodiment, at least two of $R_1$, $R_2$, and $R_3$ are independently selected from —$C_2$-$C_5$ alkyl, —$C_2$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl. In another embodiment, $R_1$, $R_2$, and $R_3$ are independently selected from —$C_2$-$C_5$ alkyl, —$C_2$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl. In another embodiment, $R_1$ and $R_2$ are —$CH_3$, $R_4$ is —$CH_2CH_2$—, and X is —H. In another embodiment, the one or more compounds are selected from compounds of the formula:

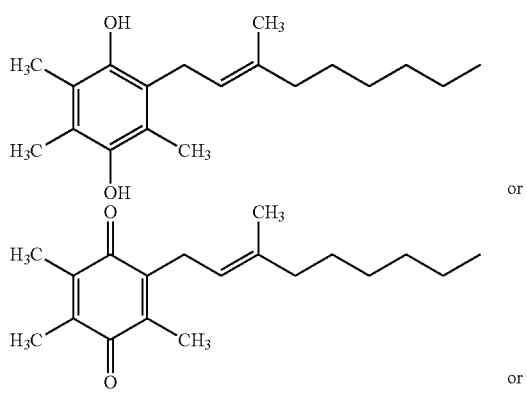

or

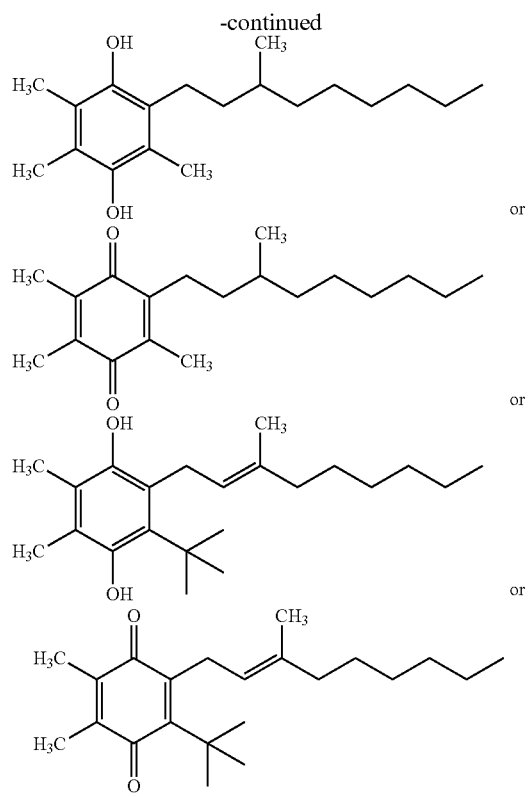

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, $R_1$ and $R_2$ are —$CH_3$, $R_4$ is a bond, and X is —OH.

In another embodiment, the one or more compounds are selected from compounds of the formula:

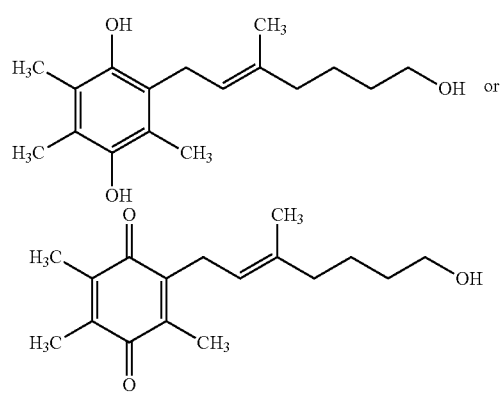

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, $R_4$ is —(CH$_2$)$_n$C(CH$_3$)$_2$—, where n is an integer from 0 to 15 inclusive; in another embodiment, X is —H or —OH.

In another embodiment, $R_4$ is a bond, where n is an integer from 0 to 15 inclusive; in another embodiment, X is —H or —OH.

In another embodiment, $R_5$ is selected from the group consisting of —H, —$C_2$-$C_5$ alkyl, —$C_3$-$C_6$ cycloalkyl, —$C_1$-$C_5$ haloalkyl, aryl, and heteroaryl. In another embodiment, $R_5$ is —$C_2$-$C_5$ alkyl. In another embodiment, at least one of $R_1$, $R_2$, and $R_3$ is independently selected from —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl. In another embodiment, at least two of $R_1$, $R_2$, and $R_3$ are independently selected from —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl. In another embodiment, $R_1$, $R_2$, and $R_3$ are independently selected from —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl. In another embodiment, $R_5$ is selected from the group consisting of —H, —$C_2$-$C_5$ alkyl, —$C_3$-$C_6$ cycloalkyl, —$C_1$-$C_5$ haloalkyl, aryl, and heteroaryl, such as —$C_2$-$C_5$ alkyl; one, two, or three of $R_1$, $R_2$, and $R_3$ are independently selected from —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl; and $R_4$ is —$(CH_2)_nC(CH_3)_2$—, where n is an integer from 0 to 15 inclusive. In another embodiment, X is —H or —OH.

In another embodiment, the invention embraces a method of treating a mitochondrial disorder, modulating one or more energy biomarkers, normalizing one or more energy biomarkers, or enhancing one or more energy biomarkers, comprising administering to a subject a therapeutically effective amount or effective amount of one or more compounds of the formula:

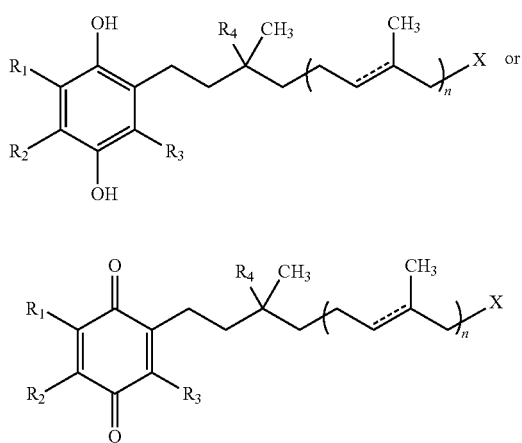

where n is an integer from 0 to 9 inclusive, and each unit can be the same or different;

wherein the bonds indicated with dashed lines can be single or double;

where $R_1$, $R_2$, and $R_3$ are independently selected from the group consisting of —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl, —O—$R_5$, —S—$R_5$, —CN, —F, —Cl, —Br, —I, —$N_3$, and —$NR_5R_6$; where $R_5$ and $R_6$ are independently selected from the group consisting of —H, —$C_1$-$C_5$ alkyl, —$C_3$-$C_6$ cycloalkyl, —$C_1$-$C_5$ haloalkyl, aryl, heteroaryl, —(C=O)—$C_0$-$C_8$ alkyl, and —(C=O)—$C_0$-$C_8$ alkyl-$C_6$-$C_{10}$ aryl-$C_0$-$C_8$ alkyl, or where $R_5$ and $R_6$ selected from these groups are combined to form a ring;

where $R_4$ is selected from the group consisting of —H, —O—$R_5$, —S—$R_5$, —F, —Cl, —Br, —I, and —$NR_5R_6$;

where X is selected from the group consisting of —H, —$NR_7R_8$, —$OR_9$ and —$(CH_2)_2C(CH_3)_2OH$;

where $R_7$ and $R_8$ are independently selected from —H, —$C_1$-$C_8$ alkyl or —$C_1$-$C_8$ haloalkyl, —(C=O)—$C_1$-$C_8$ alkyl, or where either one of $R_7$ and $R_8$ are independently selected from the group consisting of —(C=O)—$C_1$-$C_8$ haloalkyl, —(C=O)—$NH_2$, —(C=O)—$NHC_1$-$C_8$ alkyl, —(C=O)—$NHC_1$-$C_8$ haloalkyl, —(C=O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —$N(C_1$-$C_4$ alkyl)-, —O—, or —S— can be optionally incorporated in the ring formed by $R_{20}$ and $R_{21}$ and the nitrogen atom to which they are attached, —(C=O)—$OC_1$-$C_8$ alkyl, —(C=O)—$OC_1$-$C_8$ haloalkyl, —$S(O)_2C_1$-$C_8$ alkyl, —$S(O)_2$ aryl, and —$S(O)_2$ aralkyl, and where the other of $R_7$ or $R_8$ is —H, —$C_1$-$C_8$ alkyl or —$C_1$-$C_8$ haloalkyl or where $R_7$ and $R_8$ selected from these groups are combined to form a ring, or where $R_7$ is —$(CH_2)_p$—, $R_8$ is —$(CH_2)_q$—, p and q are independently integers between 0 and 7 inclusive, p+q is between 2 and 7 inclusive, $R_7$ and $R_8$ together with the nitrogen atom to which they are attached combine to form a 3- to 8-membered ring, and where another group selected from —NH—, —$N(C_1$-$C_4$ alkyl)-, —O—, or —S— can be optionally incorporated in the ring formed by $R_7$ and $R_8$ and the nitrogen atom to which they are attached;

where $R_9$ is independently selected from —H, —$C_1$-$C_8$ alkyl or —$C_1$-$C_8$ haloalkyl, —(C=O)—$C_1$-$C_8$ alkyl, —(C=O)—$C_1$-$C_8$ haloalkyl, —(C=O)—$NH_2$, —(C=O)—$NHC_1$-$C_8$ alkyl, —(C=O)—$NHC_1$-$C_8$ haloalkyl, —(C=O)—$NR_{20}R_{21}$ where $R_{20}$ is $(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —$N(C_1$-$C_4$ alkyl)-, —O—, or —S— can be optionally incorporated in the ring formed by $R_{20}$ and $R_{21}$ and the nitrogen atom to which they are attached, —(C=O)—$OC_1$-$C_8$ alkyl, —(C=O)—$OC_1$-$C_8$ haloalkyl, —$S(O)_2C_1$-$C_8$ alkyl, —$S(O)_2$ aryl, and —$S(O)_2$;

with the provisos that when n=3 and if $R_4$ is —H or —OH, then X is not —H, and that when $R_1$ and $R_2$ are —OMe and $R_3$ is -Me, then either $R_4$ is neither —H nor —OH, or X is neither —H nor —OH nor —$(CH_2)_2C(CH_3)_2OH$;

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, $R_1$, $R_2$, and $R_3$ are independently selected from the group consisting of —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl, —S—$R_5$, —CN, —F, —Cl, —Br, —I, —$N_3$, and —$NR_5R_6$. In another embodiment, $R_1$, $R_2$ and $R_3$ are independently selected from the group consisting of —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl, —S—$R_5$, —CN, —F, —Cl, —Br, —I, —$N_3$ and —$NR_5R_6$; with the proviso that when $R_1$ is —$C_1$-$C_5$ alkyl and $R_2$ is —H, then $R_3$ is not —H. In another embodiment, $R_1$, $R_2$, and $R_3$ are independently selected from —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl. In another embodiment, $R_1$, $R_2$ and $R_3$ are independently selected from —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl; with the proviso that when $R_1$ is —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, or —$C_2$-$C_5$ haloalkynyl and $R_2$ is —H, then $R_3$ is not —H. In another embodiment, at least one of $R_1$, $R_2$, and $R_3$ is independently selected from —$C_2$-$C_5$ alkyl, —$C_2$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl. In another embodiment, n=0. In another embodiment, $R_4$ is —H or —OH. In another embodiment, the one or more compounds are selected from compounds of the formula:

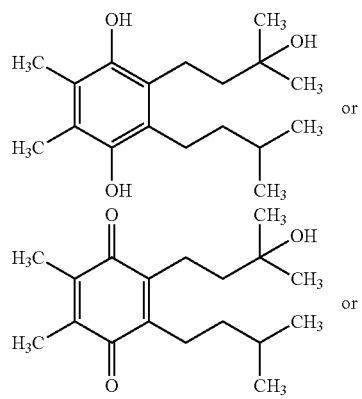

or

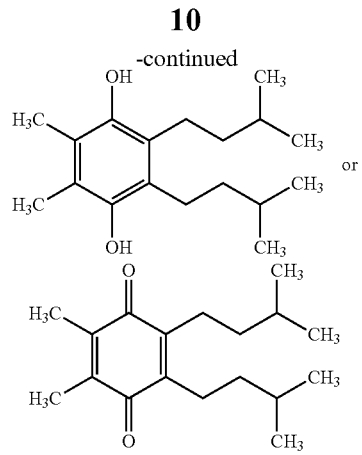

or or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, at least two of $R_1$, $R_2$, and $R_3$ are independently selected from —$C_2$-$C_5$ alkyl, —$C_2$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl. In another embodiment, $R_1$, $R_2$, and $R_3$ are independently selected from —$C_2$-$C_5$ alkyl, —$C_2$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl. In another embodiment, X is —OH or —$NH_2$.

In another embodiment, the one or more compounds are selected from compounds of the formula:

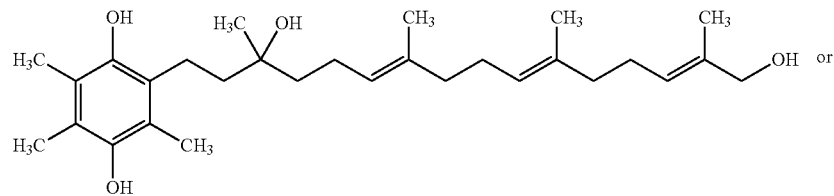

or

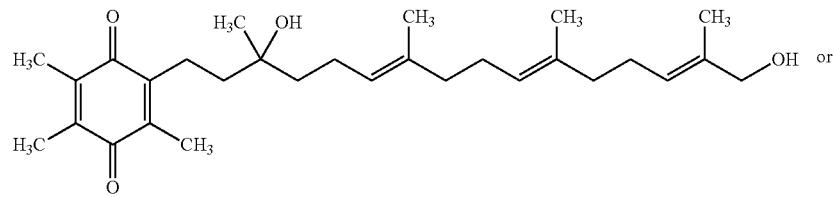

or

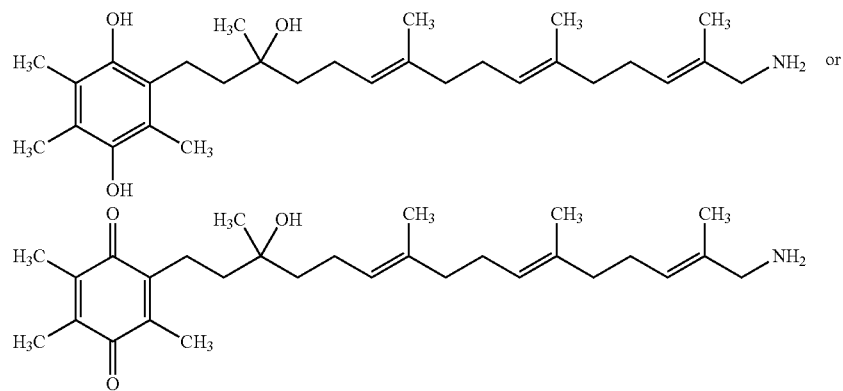

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, X is —(CH$_2$)$_2$C(CH$_3$)$_2$OH. In another embodiment, the one or more compounds are selected from compounds of the formula:

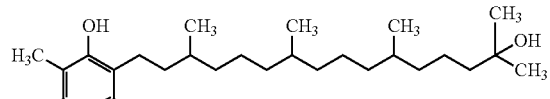

or

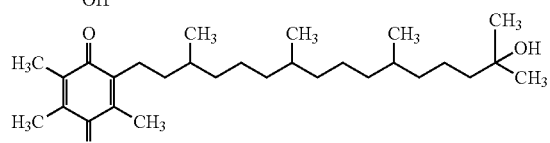

or

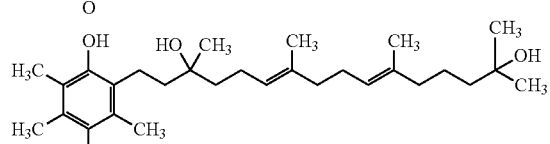

or

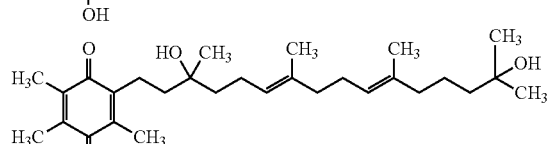

or

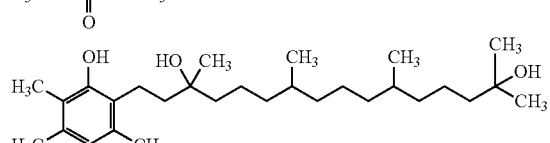

or

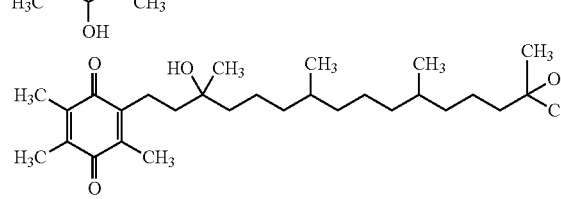

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, R$_4$ is —H, —F, —Cl, —Br, —I, or —OH. In another embodiment, R$_4$ is —F, —Cl, or —I. In another embodiment, the one or more compounds are selected from compounds of the formula:

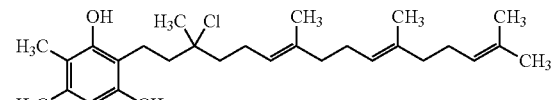

or

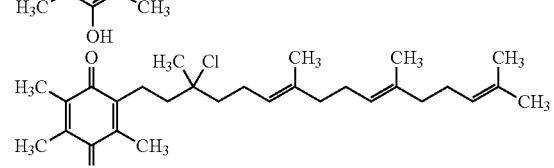

or

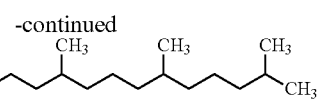

or

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, R$_4$ is —H, or —OH. In another embodiment, the one or more compounds are selected from compounds of the formula:

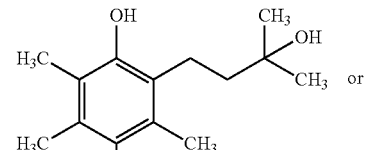

or

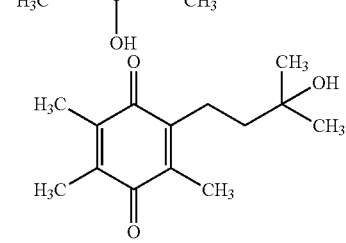

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In one embodiment, the invention embraces a method of treating a mitochondrial disorder, modulating one or more energy biomarkers, normalizing one or more energy biomarkers, or enhancing one or more energy biomarkers, comprising administering to a subject a therapeutically effective amount or effective amount of one or more compounds of the formula:

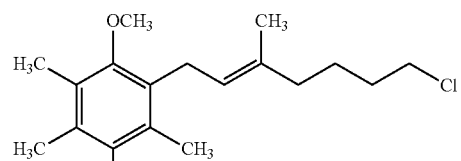

or

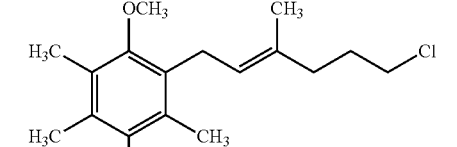

or

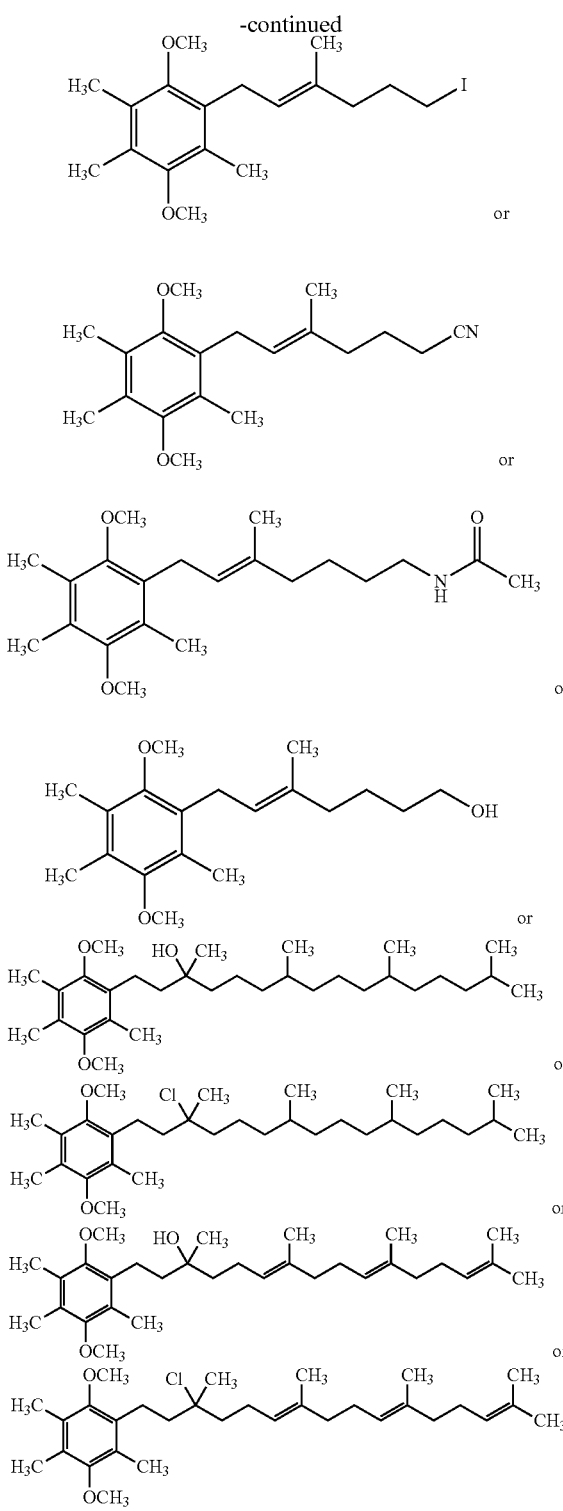

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In any of the methods above, the compound or compounds to be administered can be combined with a pharmaceutically acceptable excipient.

In any of the methods above, the mitochondrial disorder can be selected from the group consisting of inherited mitochondrial diseases; Myoclonic Epilepsy with Ragged Red Fibers (MERRF); Mitochondrial Myopathy, Encephalopathy, Lactacidosis, Stroke (MELAS); Leber's Hereditary Optic Neuropathy (LHON); Leigh Disease; Kearns-Sayre Syndrome (KSS); Friedreich's Ataxia (FA); other myopathies; cardiomyopathy; encephalomyopathy; renal tubular acidosis; neurodegenerative diseases; Parkinson's disease; Alzheimer's disease; amyotrophic lateral sclerosis (ALS); motor neuron diseases; other neurological diseases; epilepsy; genetic diseases; Huntington's Disease; mood disorders; schizophrenia; bipolar disorder; age-associated diseases; macular degeneration; diabetes; and cancer. In another embodiment, the mitochondrial disorder can be selected from the group consisting of inherited mitochondrial diseases; Myoclonic Epilepsy with Ragged Red Fibers (MERRF); Mitochondrial Myopathy, Encephalopathy, Lactacidosis, Stroke (MELAS); Leber's Hereditary Optic Neuropathy (LHON); Leigh Disease; Kearns-Sayre Syndrome (KSS); and Friedreich's Ataxia (FA).

In any of the methods above for modulating one or more energy biomarkers, normalizing one or more energy biomarkers, or enhancing one or more energy biomarkers, the energy biomarker can be selected from the group consisting of: lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH (NADH+H$^+$) levels; NADPH (NADPH+H$^+$) levels; NAD levels; NADP levels; ATP levels; reduced coenzyme Q (CoQ$^{red}$) levels; oxidized coenzyme Q (CoQ$^{ox}$) levels; total coenzyme Q (CoQ$^{tot}$) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'-deoxyguanosine (8-OHdG) levels; levels of reactive oxygen species; levels of oxygen consumption (VO2); levels of carbon dioxide output (VCO2); respiratory quotient (VCO2/VO2); exercise tolerance; and anaerobic threshold.

In any of the above methods, the subject can be selected from the group consisting of: a subject with a mitochondrial disease; a subject undergoing strenuous or prolonged physical activity; a subject with chronic energy problems; a subject with chronic respiratory problems; a pregnant female; a pregnant female in labor; a neonate; a premature neonate; a subject exposed to an extreme environment; a subject exposed to a hot environment; a subject exposed to a cold environment; a subject exposed to an environment with lower-than-average oxygen content; a subject exposed to an environment with higher-than-average carbon dioxide content; a subject exposed to an environment with higher-than-average levels of air pollution; a subject with lung disease; a subject with lower-than-average lung capacity; a tubercular patient; a lung cancer patient; an emphysema patient; a cystic fibrosis patient; a subject recovering from surgery; a subject recovering from illness; a subject undergoing acute trauma; a subject in shock; a subject requiring acute oxygen administration; a subject requiring chronic oxygen administration; an elderly subject; an elderly subject experiencing decreased energy; and a subject suffering from chronic fatigue.

In another embodiment, the invention embraces compounds of the formula:

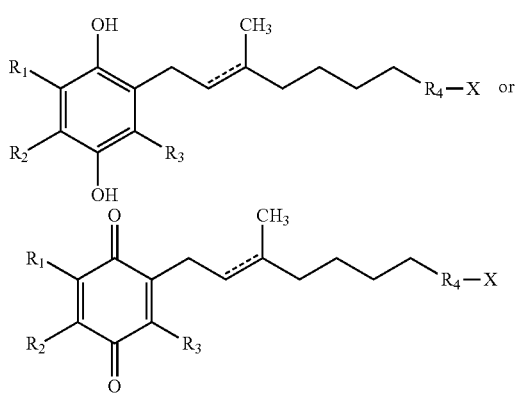

wherein the bond indicated with a dashed line can be single or double;

where $R_1$, $R_2$, and $R_3$ are independently selected from the group consisting of —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl, —S—$R_5$, —CN, —F, —Cl, —Br, —I, —$N_3$, and —$NR_5R_6$, where at least one of $R_1$, $R_2$, and $R_3$ is independently selected from —$C_2$-$C_5$ alkyl;

where $R_5$ and $R_6$ are independently selected from the group consisting of —H, —$C_1$-$C_5$ alkyl, —$C_3$-$C_6$ cycloalkyl, —$C_1$-$C_5$ haloalkyl, aryl, heteroaryl, —(C=O)—$C_0$-$C_8$ alkyl, —(C=O)—$C_0$-$C_8$ alkyl-$C_6$-$C_{10}$ aryl-$C_0$-$C_8$ alkyl, or where $R_5$ and $R_6$ selected from these groups are combined to form a ring;

where $R_4$ represents a linear or branched group containing 1 to 32 carbon atoms and any number of single, double, or triple bonds in any chemically possible combination;

where X is selected from the group consisting of —H, —F, —Br, —I, —CN, —$N_3$, —$NR_7R_8$, and —$OR_9$;

where $R_7$ and $R_8$ are independently selected from —H, —$C_1$-$C_8$ alkyl or —$C_1$-$C_8$ haloalkyl, —(C=O)—$C_1$-$C_8$ alkyl, or where either one of $R_7$ and $R_8$ are independently selected from the group consisting of —(C=O)—$C_1$-$C_8$ haloalkyl, —(C=O)—$NH_2$, —(C=O)—$NHC_1$-$C_8$ alkyl, —(C=O)—$NHC_1$-$C_8$ haloalkyl, —(C=O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_{20}$ and $R_{21}$ and the nitrogen atom to which they are attached, —(C=O)—$OC_1$-$C_8$ alkyl, —(C=O)—$OC_1$-$C_8$ haloalkyl, —$S(O)_2C_1$-$C_8$ alkyl, —$S(O)_2$ aryl, and —$S(O)_2$ aralkyl, and where the other of $R_7$ or $R_8$ is —H, —$C_1$-$C_8$ alkyl or —$C_1$-$C_8$ haloalkyl or where $R_7$ and $R_8$ selected from these groups are combined to form a ring, or where $R_7$ is —$(CH_2)_p$—, $R_8$ is —$(CH_2)_q$—, p and q are independently integers between 0 and 7 inclusive, p+q is between 2 and 7 inclusive, $R_7$ and $R_8$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_7$ and $R_8$ and the nitrogen atom to which they are attached;

where $R_9$ is independently selected from —H, —$C_1$-$C_8$ alkyl or —$C_1$-$C_8$ haloalkyl, —(C=O)—$C_1$-$C_8$ alkyl, —(C=O)—$C_1$-$C_8$ haloalkyl, —(C=O)—$NH_2$, —(C=O)—$NHC_1$-$C_8$ alkyl, —(C=O)—$NHC_1$-$C_8$ haloalkyl, —(C=O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_{20}$ and $R_{21}$ and the nitrogen atom to which they are attached, —(C=O)—$OC_1$-$C_8$ alkyl, —(C=O)—$OC_1$-$C_8$ haloalkyl, —$S(O)_2C_1$-$C_8$ alkyl, —$S(O)_2$ aryl, and —$S(O)_2$;

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, $R_1$, $R_2$, and $R_3$ are independently selected from —H —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl, and where at least one of $R_1$, $R_2$, and $R_3$ is independently selected from —$C_2$-$C_5$ alkyl, —$C_2$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl. In another embodiment, at least one of $R_1$, $R_2$, and $R_3$ is independently selected from —$C_2$-$C_5$ alkyl, —$C_2$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl; with the proviso that X is not —H. In another embodiment, at least two of $R_1$, $R_2$, and $R_3$ are independently selected from —$C_2$-$C_5$ alkyl, —$C_2$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl. In another embodiment, $R_1$, $R_2$, and $R_3$ are independently selected from —$C_2$-$C_5$ alkyl, —$C_2$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl.

In another embodiment, the invention embraces compounds of the formula:

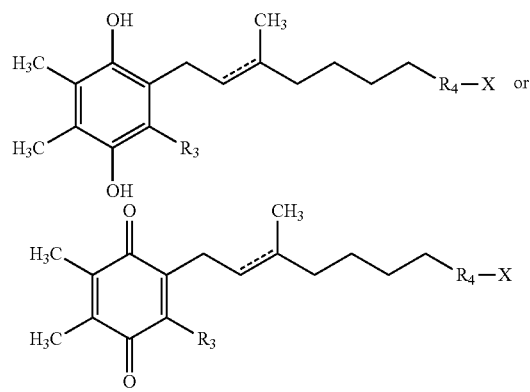

wherein the bond indicated with a dashed line can be single or double;

where $R_3$ is selected from the group consisting of —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl, —S—$R_5$, —CN, —F, —Cl, —Br, —I, —$N_3$, and —$NR_5R_6$;

where $R_5$ and $R_6$ are independently selected from the group consisting of —H, —$C_1$-$C_5$ alkyl, —$C_3$-$C_6$ cycloalkyl, —$C_1$-$C_5$ haloalkyl, aryl, heteroaryl, —(C=O)—$C_0$-$C_8$ alkyl, —(C=O)—$C_0$-$C_8$ alkyl-$C_6$-$C_{10}$ aryl-$C_0$-$C_8$ alkyl, or where $R_5$ and $R_6$ selected from these groups are combined to form a ring;

where $R_4$ represents a linear or branched group containing 1 to 32 carbon atoms and any number of single, double, or triple bonds in any chemically possible combination;

where X is selected from the group consisting of —F, —Cl, —Br, —I, —CN, —$N_3$, —$NR_7R_8$, and —$OR_9$;

where $R_7$ and $R_8$ are independently selected from —H, —$C_1$-$C_8$ alkyl or —$C_1$-$C_8$ haloalkyl, —(C=O)—$C_1$-$C_8$ alkyl, or where either one of $R_7$ and $R_8$ are independently selected from the group consisting of —(C=O)—$C_1$-$C_8$ haloalkyl, —(C=O)—$NH_2$, —(C=O)—NH$C_1$-$C_8$ alkyl, —(C=O)—NH$C_1$-$C_8$ haloalkyl, —(C=O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_{20}$ and $R_{21}$ and the nitrogen atom to which they are attached, —(C=O)—O$C_1$-$C_8$ alkyl, —(C=O)—O$C_1$-$C_8$ haloalkyl, —$S(O)_2C_1$-$C_8$ alkyl, —$S(O)_2$ aryl, and —$S(O)_2$ aralkyl, and where the other of $R_7$ or $R_8$ is —H, —$C_1$-$C_8$ alkyl or —$C_1$-$C_8$ haloalkyl or where $R_7$ and $R_8$ selected from these groups are combined to form a ring, or where $R_7$ is —$(CH_2)_p$—, $R_8$ is —$(CH_2)_q$—, p and q are independently integers between 0 and 7 inclusive, p+q is between 2 and 7 inclusive, $R_7$ and $R_8$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_7$ and $R_8$ and the nitrogen atom to which they are attached;

where $R_9$ is independently selected from —H, —$C_1$-$C_8$ alkyl or —$C_1$-$C_8$ haloalkyl, —(C=O)—$C_1$-$C_8$ alkyl, —(C=O)—$C_1$-$C_8$ haloalkyl, —(C=O)—$NH_2$, —(C=O)—NH$C_1$-$C_8$ alkyl, —(C=O)—NH$C_1$-$C_8$ haloalkyl, —(C=O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_{20}$ and $R_{21}$ and the nitrogen atom to which they are attached, —(C=O)—O$C_1$-$C_8$ alkyl, —(C=O)—O$C_1$-$C_8$ haloalkyl, —$S(O)_2C_1$-$C_8$ alkyl, —$S(O)_2$ aryl, and —$S(O)_2$;

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, the one or more compounds are selected from compounds of the formula:

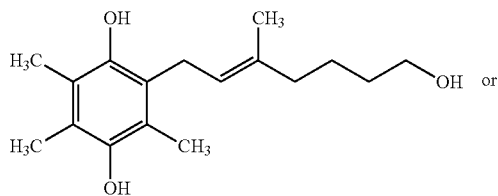

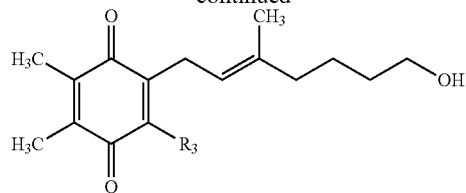

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, the invention embraces compounds of the formula:

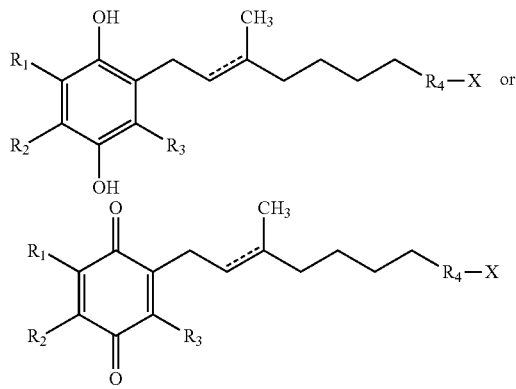

wherein the bond indicated with a dashed line can be single or double;

where $R_1$, $R_2$, and $R_3$ are independently selected from the group consisting of —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl, —S—$R_5$, —CN, —F, —Cl, —Br, —I, —$N_3$, and —$NR_5R_6$; where $R_5$ and $R_6$ are independently selected from the group consisting of —H, —$C_1$-$C_5$ alkyl, —$C_3$-$C_6$ cycloalkyl, —$C_1$-$C_5$ haloalkyl, aryl, heteroaryl, —(C=O)—$C_0$-$C_8$ alkyl, and —(C=O)—$C_0$-$C_8$ alkyl-$C_6$-$C_{10}$ aryl-$C_0$-$C_8$ alkyl, or where $R_5$ and $R_6$ selected from these groups are combined to form a ring;

where $R_4$ is —$(CH_2)_nC(CH_3)_2$—, where n is an integer from 0 to 15 inclusive;

where X is selected from the group consisting of —H, —F, —Cl, —Br, —I, —CN, —$N_3$, —$NR_7R_8$, and —$OR_9$;

where $R_7$ and $R_8$ are independently selected from —H, —$C_1$-$C_8$ alkyl or —$C_1$-$C_8$ haloalkyl, —(C=O)—$C_1$-$C_8$ alkyl, or where either one of $R_7$ and $R_8$ are independently selected from the group consisting of —(C=O)—$C_1$-$C_8$ haloalkyl, —(C=O)—$NH_2$, —(C=O)—NH$C_1$-$C_8$ alkyl, —(C=O)—NH$C_1$-$C_8$ haloalkyl, —(C=O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_{20}$ and $R_{21}$ and the nitrogen atom to which they are attached, —(C=O)—O$C_1$-$C_8$ alkyl, —(C=O)—O$C_1$-$C_8$ haloalkyl, —S(O)$_2$C$_1$-C$_8$ alkyl, —S(O)$_2$ aryl, and —S(O)$_2$ aralkyl, and where the other of R$_7$ or R$_8$ is —H, —C$_1$-C$_8$ alkyl or —C$_1$-C$_8$ haloalkyl or where R$_7$ and R$_8$ selected from these groups are combined to form a ring, or where R$_7$ is —(CH$_2$)$_p$—, R$_8$ is —(CH$_2$)$_q$—, p and q are independently integers between 0 and 7 inclusive, p+q is between 2 and 7 inclusive, R$_7$ and R$_8$ together with the nitrogen atom to which they are attached combine to form a 3- to 8-membered ring, and where another group selected from —NH—, —N(C$_1$-C$_4$ alkyl)-, —O—, or —S— can be optionally incorporated in the ring formed by R$_7$ and R$_8$ and the nitrogen atom to which they are attached;

where R$_9$ is independently selected from —H, —C$_1$-C$_8$ alkyl or —C$_1$-C$_8$ haloalkyl, —(C═O)—C$_1$-C$_8$ alkyl, —(C═O)—C$_1$-C$_8$ haloalkyl, —(C═O)—NH$_2$, —(C═O)—NHC$_1$-C$_8$ alkyl, —(C═O)—NHC$_1$-C$_8$ haloalkyl, —(C═O)—NR$_{20}$R$_{21}$ where R$_{20}$ is —(CH$_2$)$_p$—, R$_{21}$ is —(CH$_2$)$_q$—, p and q are independently integers between 0 and 7 inclusive, p+q is between 2 and 7 inclusive, R$_{20}$ and R$_{21}$ together with the nitrogen atom to which they are attached combine to form a 3- to 8-membered ring, and where another group selected from —NH—, —N(C$_1$-C$_4$ alkyl)-, —O—, or —S— can be optionally incorporated in the ring formed by R$_{20}$ and R$_{21}$ and the nitrogen atom to which they are attached, —(C═O)—OC$_1$-C$_8$ alkyl, —(C═O)—OC$_1$-C$_8$ haloalkyl, —S(O)$_2$C$_1$-C$_8$ alkyl, —S(O)$_2$ aryl, and —S(O)$_2$;

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, X is —H or —OH.

In another embodiment, the invention embraces compounds of the formula:

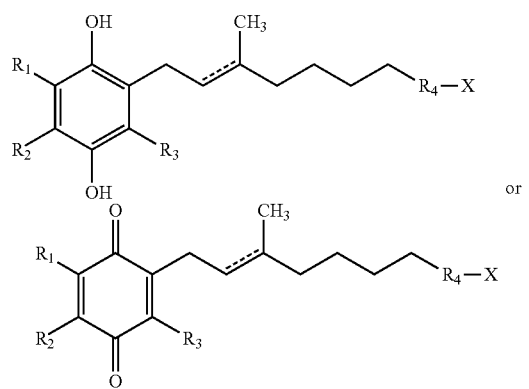

wherein the bond indicated with a dashed line can be single or double;

where R$_1$, R$_2$, and R$_3$ are independently selected from the group consisting of —H, —C$_1$-C$_5$ alkyl, —C$_1$-C$_5$ haloalkyl, —C$_2$-C$_5$ alkenyl, —C$_2$-C$_5$ haloalkenyl, —C$_2$-C$_5$ alkynyl, —C$_2$-C$_5$ haloalkynyl, —O—R$_5$, —S—R$_5$, —CN, —F, —Cl, —Br, —I, —N$_3$, and —NR$_5$R$_6$; where R$_5$ is independently selected from group consisting of —C$_2$-C$_5$ alkyl, —C$_3$-C$_6$ cycloalkyl, —C$_1$-C$_5$ haloalkyl, aryl, and heteroaryl, and R$_6$ is independently selected from the group consisting of —H, —C$_1$-C$_5$ alkyl, —C$_3$-C$_6$ cycloalkyl, —C$_1$-C$_5$ haloalkyl, aryl, heteroaryl, —(C═O)—C$_0$-C$_8$ alkyl, and —(C═O)—C$_0$-C$_8$ alkyl-C$_6$-C$_{10}$ aryl-C$_0$-C$_8$ alkyl, or where R$_5$ and R$_6$ selected from these groups are combined to form a ring; with the proviso that at least one of R$_1$, R$_2$, and R$_3$ is —OR$_5$;

where R$_4$ represents a linear or branched group containing 1 to 32 carbon atoms and any number of single, double, or triple bonds in any chemically possible combination;

where X is selected from the group consisting of —H, —F, —Cl, —Br, —I, —CN, —N$_3$, —NR$_7$R$_8$, and —OR$_9$;

where R$_7$ and R$_8$ are independently selected from —H, —C$_1$-C$_8$ alkyl or —C$_1$-C$_8$ haloalkyl, —(C═O)—C$_1$-C$_8$ alkyl, or where either one of R$_7$ and R$_8$ are independently selected from the group consisting of —(C═O)—C$_1$-C$_8$ haloalkyl, —(C═O)—NH$_2$, —(C═O)—NHC$_1$-C$_8$ alkyl, —(C═O)—NHC$_1$-C$_8$ haloalkyl, —(C═O)—NR$_{20}$R$_{21}$ where R$_{20}$ is —(CH$_2$)$_p$—, R$_{21}$ is —(CH$_2$)$_q$—, p and q are independently integers between 0 and 7 inclusive, p+q is between 2 and 7 inclusive, R$_{20}$ and R$_{21}$ together with the nitrogen atom to which they are attached combine to form a 3- to 8-membered ring, and where another group selected from —NH—, —N(C$_1$-C$_4$ alkyl)-, —O—, or —S— can be optionally incorporated in the ring formed by R$_{20}$ and R$_{21}$ and the nitrogen atom to which they are attached, —(C═O)—OC$_1$-C$_8$ alkyl, —(C═O)—OC$_1$-C$_8$ haloalkyl, —S(O)$_2$C$_1$-C$_8$ alkyl, —S(O)$_2$ aryl, and —S(O)$_2$ aralkyl, and where the other of R$_7$ or R$_8$ is —H, —C$_1$-C$_8$ alkyl or —C$_1$-C$_8$ haloalkyl or where R$_7$ and R$_8$ selected from these groups are combined to form a ring, or where R$_7$ is —(CH$_2$)$_p$—, R$_8$ is —(CH$_2$)$_q$—, p and q are independently integers between 0 and 7 inclusive, p+q is between 2 and 7 inclusive, R$_7$ and R$_8$ together with the nitrogen atom to which they are attached combine to form a 3- to 8-membered ring, and where another group selected from —NH—, —N(C$_1$-C$_4$ alkyl)-, —O—, or —S— can be optionally incorporated in the ring formed by R$_7$ and R$_8$ and the nitrogen atom to which they are attached;

where R$_9$ is independently selected from —H, —C$_1$-C$_8$ alkyl or —C$_1$-C$_8$ haloalkyl, —(C═O)—C$_1$-C$_8$ alkyl, —(C═O)—C$_1$-C$_8$ haloalkyl, —(C═O)—NH$_2$, —(C═O)—NHC$_1$-C$_8$ alkyl, —(C═O)—NHC$_1$-C$_8$ haloalkyl, —(C═O)—NR$_{20}$R$_{21}$ where R$_{20}$ is —(CH$_2$)$_p$—, R$_{21}$ is —(CH$_2$)$_q$—, p and q are independently integers between 0 and 7 inclusive, p+q is between 2 and 7 inclusive, R$_{20}$ and R$_{21}$ together with the nitrogen atom to which they are attached combine to form a 3- to 8-membered ring, and where another group selected from —NH—, —N(C$_1$-C$_4$ alkyl)-, —O—, or —S— can be optionally incorporated in the ring formed by R$_{20}$ and R$_{21}$ and the nitrogen atom to which they are attached, —(C═O)—OC$_1$-C$_8$ alkyl, —(C═O)—OC$_1$-C$_8$ haloalkyl, —S(O)$_2$C$_1$-C$_8$ alkyl, —S(O)$_2$ aryl, and —S(O)$_2$;

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, at least two of R$_1$, R$_2$, and R$_3$ are independently selected from —C$_1$-C$_5$ alkyl, —C$_1$-C$_5$ haloalkyl, —C$_2$-C$_5$ alkenyl, —C$_2$-C$_5$ haloalkenyl, —C$_2$-C$_5$ alkynyl, and —C$_2$-C$_5$ haloalkynyl. In another embodiment, R$_1$, R$_2$, and R$_3$ are independently selected from —C$_1$-C$_5$ alkyl, —C$_1$-C$_5$ haloalkyl, —C$_2$-C$_5$ alkenyl, —C$_2$-C$_5$ haloalkenyl, —C$_2$-C$_5$ alkynyl, and —C$_2$-C$_5$ haloalkynyl.

In another embodiment, the invention embraces compounds of the formula:

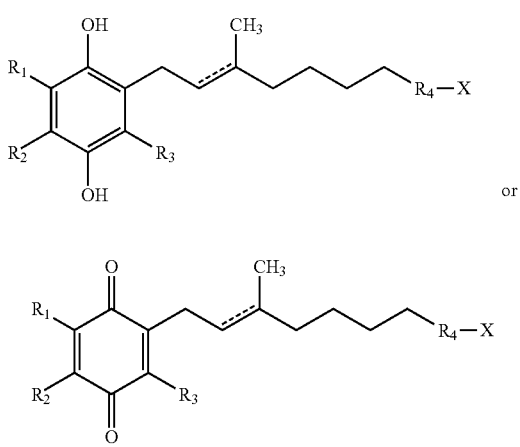

wherein the bond indicated with a dashed line can be single or double;

where $R_1$, $R_2$, and $R_3$ are independently selected from the group consisting of —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl, —O—$R_5$, —S—$R_5$, —CN, —F, —Cl, —Br, —I, —$N_3$, and —$NR_5R_6$;

where $R_5$ is independently selected from group consisting of —H, —$C_2$-$C_5$ alkyl, —$C_3$-$C_6$ cycloalkyl, —$C_1$-$C_5$ haloalkyl, aryl, and heteroaryl, and $R_6$ is independently selected from the group consisting of —H, —$C_1$-$C_5$ alkyl, —$C_3$-$C_6$ cycloalkyl, —$C_1$-$C_5$ haloalkyl, aryl, heteroaryl, —(C═O)—$C_0$-$C_8$ alkyl, and —(C═O)—$C_0$-$C_8$ alkyl-$C_6$-$C_{10}$ aryl-$C_0$-$C_8$ alkyl, or where $R_5$ and $R_6$ selected from these groups are combined to form a ring;

where $R_4$—$(CH_2)_nC(CH_3)_2$— where n is an integer from 0 to 15 inclusive;

where X is selected from the group consisting of —H, —F, —Cl, —Br, —I, —CN, —$N_3$, —$NR_7R_8$, and —$OR_9$;

where $R_7$ and $R_8$ are independently selected from —H, —$C_1$-$C_8$ alkyl or —$C_1$-$C_8$ haloalkyl, —(C═O)—$C_1$-$C_8$ alkyl, or where either one of $R_7$ and $R_8$ are independently selected from the group consisting of —(C═O)—$C_1$-$C_8$ haloalkyl, —(C═O)—$NH_2$, —(C═O)—$NHC_1$-$C_8$ alkyl, —(C═O)—$NHC_1$-$C_8$ haloalkyl, —(C═O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_{20}$ and $R_{21}$ and the nitrogen atom to which they are attached, —(C═O)—$OC_1$-$C_8$ alkyl, —(C═O)—$OC_1$-$C_8$ haloalkyl, —$S(O)_2C_1$-$C_8$ alkyl, —$S(O)_2$ aryl, and —$S(O)_2$ aralkyl, and where the other of $R_7$ or $R_8$ is —H, —$C_1$-$C_8$ alkyl or —$C_1$-$C_8$ haloalkyl or where $R_7$ and $R_8$ selected from these groups are combined to form a ring, or where $R_7$ is —$(CH_2)_p$—, $R_8$ is —$(CH_2)_q$—, p and q are independently integers between 0 and 7 inclusive, p+q is between 2 and 7 inclusive, $R_7$ and $R_8$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_7$ and $R_8$ and the nitrogen atom to which they are attached;

where $R_9$ is independently selected from —H, —$C_1$-$C_8$ alkyl or —$C_1$-$C_8$ haloalkyl, —(C═O)—$C_1$-$C_8$ alkyl, —(C═O)—$C_1$-$C_8$ haloalkyl, —(C═O)—$NH_2$, —(C═O)—$NHC_1$-$C_8$ alkyl, —(C═O)—$NHC_1$-$C_8$ haloalkyl, —(C═O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_{20}$ and $R_{21}$ and the nitrogen atom to which they are attached, —(C═O)—$OC_1$-$C_8$ alkyl, —(C═O)—$OC_1$-$C_8$ haloalkyl, —$S(O)_2C_1$-$C_8$ alkyl, —$S(O)_2$ aryl, and —$S(O)_2$;

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, X is —H or —OH.

In another embodiment, the invention embraces compounds of the formula:

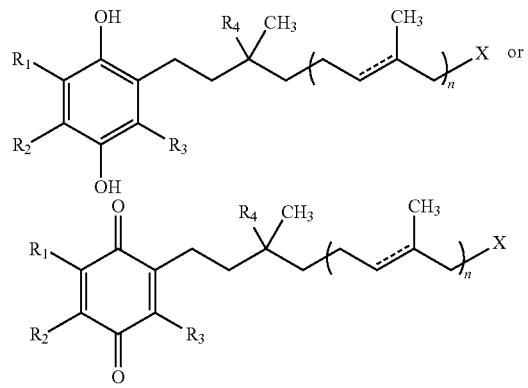

where n is an integer from 0 to 9 inclusive, and each unit can be the same or different;

wherein the bonds indicated with dashed lines can be single or double;

wherein $R_1$, $R_2$ and $R_3$ are independently selected from —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl, and wherein at least one of $R_1$, $R_2$, and $R_3$ is independently selected from —$C_2$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl, with the proviso that when $R_2$ is —$C_1$-$C_5$ alkyl and $R_1$ is —H, then $R_3$ is not —H;

where $R_4$ is selected from the group consisting of —H, —O—$R_5$, —S—$R_5$, —F, —Cl, —Br, —I, and —$NR_5R_6$;

where X is selected from the group consisting of —H, —$NR_7R_8$, —$OR_9$ and —$(CH_2)_2C(CH_3)_2OH$; where $R_5$ and $R_6$ are independently selected from the group consisting of —H, —$C_1$-$C_5$ alkyl, —$C_3$-$C_6$ cycloalkyl, —$C_1$-$C_5$ haloalkyl, aryl, heteroaryl, —(C═O)—$C_0$-$C_8$ alkyl, and —(C═O)—$C_0$-$C_8$ alkyl-$C_6$-$C_{10}$ aryl-$C_0$-$C_8$ alkyl, or where $R_5$ and $R_6$ selected from these groups are combined to form a ring;

where $R_7$ and $R_8$ are independently selected from —H, —$C_1$-$C_8$ alkyl or —$C_1$-$C_8$ haloalkyl, —(C═O)—$C_1$-$C_8$ alkyl, or where either one of $R_7$ and $R_8$ are independently selected from the group consisting of —(C═O)—$C_1$-$C_8$ haloalkyl, —(C═O)—$NH_2$, —(C═O)—$NHC_1$-$C_8$ alkyl, —(C=O)—NHC$_1$-C$_8$ haloalkyl, —(C=O)—NR$_{20}$R$_{21}$ where R$_{20}$ is —(CH$_2$)$_p$—, R$_{21}$ is —(CH$_2$)$_q$—, p and q are independently integers between 0 and 7 inclusive, p+q is between 2 and 7 inclusive, R$_{20}$ and R$_{21}$ together with the nitrogen atom to which they are attached combine to form a 3- to 8-membered ring, and where another group selected from —NH—, —N(C$_1$-C$_4$ alkyl)-, —O—, or —S— can be optionally incorporated in the ring formed by R$_{20}$ and R$_{21}$ and the nitrogen atom to which they are attached, —(C=O)—OC$_1$-C$_8$ alkyl, —(C=O)—OC$_1$-C$_8$ haloalkyl, —S(O)$_2$C$_1$-C$_8$ alkyl, —S(O)$_2$ aryl, and —S(O)$_2$ aralkyl, and where the other of R$_7$ or R$_8$ is —H, —C$_1$-C$_8$ alkyl or —C$_1$-C$_8$ haloalkyl or where R$_7$ and R$_8$ selected from these groups are combined to form a ring, or where R$_7$ is —(CH$_2$)$_p$—, R$_8$ is —(CH$_2$)$_q$—, p and q are independently integers between 0 and 7 inclusive, p+q is between 2 and 7 inclusive, R$_7$ and R$_8$ together with the nitrogen atom to which they are attached combine to form a 3- to 8-membered ring, and where another group selected from —NH—, —N(C$_1$-C$_4$ alkyl)-, —O—, or —S— can be optionally incorporated in the ring formed by R$_7$ and R$_8$ and the nitrogen atom to which they are attached;

where R$_9$ is independently selected from —H, —C$_1$-C$_8$ alkyl or —C$_1$-C$_8$ haloalkyl, —(C=O)—C$_1$-C$_8$ alkyl, —(C=O)—C$_1$-C$_8$ haloalkyl, —(C=O)—NH$_2$, —(C=O)—NHC$_1$-C$_8$ alkyl, —(C=O)—NHC$_1$-C$_8$ haloalkyl, —(C=O)—NR$_{20}$R$_{21}$ where R$_{20}$ is —(CH$_2$)$_p$—, R$_{21}$ is —(CH$_2$)$_q$—, p and q are independently integers between 0 and 7 inclusive, p+q is between 2 and 7 inclusive, R$_{20}$ and R$_{21}$ together with the nitrogen atom to which they are attached combine to form a 3- to 8-membered ring, and where another group selected from —NH—, —N(C$_1$-C$_4$ alkyl)-, —O—, or —S— can be optionally incorporated in the ring formed by R$_{20}$ and R$_{21}$ and the nitrogen atom to which they are attached, —(C=O)—OC$_1$-C$_8$ alkyl, —(C=O)—OC$_1$-C$_8$ haloalkyl, —S(O)$_2$C$_1$-C$_8$ alkyl, —S(O)$_2$ aryl, and —S(O)$_2$;

with the provisos that when n=3 and R$_4$ is —H or —OH, then X is not —H, or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, n=0. In another embodiment, R$_4$ is —H or —OH. In another embodiment, the compound is of the formula:

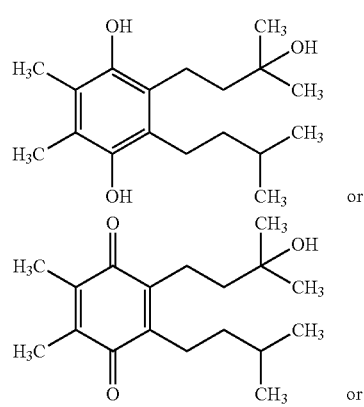

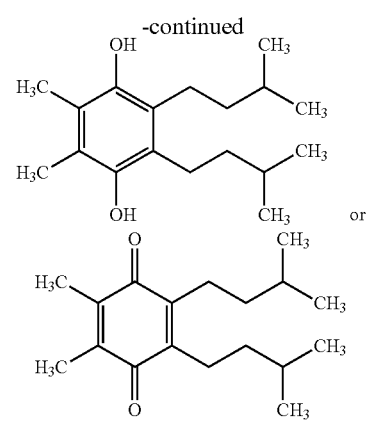

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, at least two of R$_1$, R$_2$, and R$_3$ are independently selected from —C$_2$-C$_5$ alkyl, —C$_2$-C$_5$ haloalkyl, —C$_2$-C$_5$ alkenyl, —C$_2$-C$_5$ haloalkenyl, —C$_2$-C$_5$ alkynyl, —C$_2$-C$_5$ haloalkynyl. In another embodiment, R$_1$, R$_2$, and R$_3$ are independently selected from —C$_2$-C$_5$ alkyl, —C$_2$-C$_5$ haloalkyl, —C$_2$-C$_5$ alkenyl, —C$_2$-C$_5$ haloalkenyl, —C$_2$-C$_5$ alkynyl, —C$_2$-C$_5$ haloalkynyl.

In another embodiment, the invention embraces compounds of the formula:

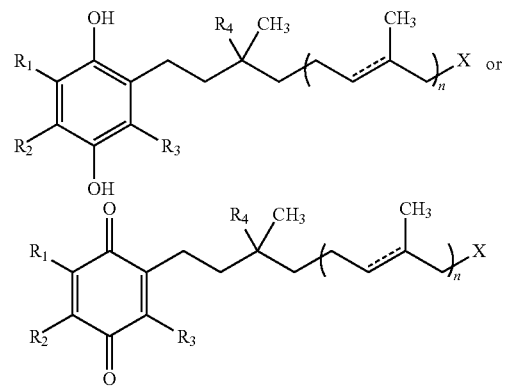

where n is an integer from 0 to 9 inclusive, and each unit can be the same or different;

wherein the bonds indicated with dashed lines can be single or double;

wherein R$_1$, R$_2$ and R$_3$ are independently selected from —H, —C$_1$-C$_5$ alkyl, —C$_1$-C$_5$ haloalkyl, —C$_2$-C$_5$ alkenyl, —C$_2$-C$_5$ haloalkenyl, —C$_2$-C$_5$ alkynyl, —C$_2$-C$_5$ haloalkynyl with the proviso that when R$_2$ is —C$_1$-C$_5$ alkyl and R$_1$ is —H, then R$_3$ is not —H; where R$_4$ is selected from the group consisting of —H, —O—R$_5$, —S—R$_5$, —F, —Cl, —Br, —I, and —NR$_5$R$_6$; where X is selected from the group consisting of —NR$_7$R$_8$, —OR$_9$ and —(CH$_2$)$_2$C(CH$_3$)$_2$OH;

where R$_5$ and R$_6$ are independently selected from the group consisting of —H, —C$_1$-C$_5$ alkyl, —C$_3$-C$_6$ cycloalkyl, —C$_1$-C$_5$ haloalkyl, aryl, heteroaryl, —(C=O)—C$_0$-C$_8$ alkyl, and —(C=O)—C$_0$-C$_8$ alkyl-C$_6$-C$_{10}$ aryl-C$_0$-C$_8$ alkyl, or where R$_5$ and R$_6$ selected from these groups are combined to form a ring;

where $R_7$ and $R_8$ are independently selected from —H, —$C_1$-$C_8$ alkyl or —$C_1$-$C_8$ haloalkyl, —(C=O)—$C_1$-$C_8$ alkyl, or where either one of $R_7$ and $R_8$ are independently selected from the group consisting of —(C=O)—$C_1$-$C_8$ haloalkyl, —(C=O)—$NH_2$, —(C=O)—$NHC_1$-$C_8$ alkyl, —(C=O)—$NHC_1$-$C_8$ haloalkyl, —(C=O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_{20}$ and $R_{21}$ and the nitrogen atom to which they are attached, —(C=O)—$OC_1$-$C_8$ alkyl, —(C=O)—$OC_1$-$C_8$ haloalkyl, —$S(O)_2C_1$-$C_8$ alkyl, —$S(O)_2$ aryl, and —$S(O)_2$ aralkyl, and where the other of $R_7$ or $R_8$ is —H, —$C_1$-$C_8$ alkyl or —$C_1$-$C_8$ haloalkyl or where $R_7$ and $R_8$ selected from these groups are combined to form a ring, or where $R_7$ is —$(CH_2)_p$—, $R_8$ is —$(CH_2)_q$—, p and q are independently integers between 0 and 7 inclusive, p+q is between 2 and 7 inclusive, $R_7$ and $R_8$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_7$ and $R_8$ and the nitrogen atom to which they are attached;

where $R_9$ is independently selected from —H, —$C_1$-$C_8$ alkyl or —$C_1$-$C_8$ haloalkyl, —(C=O)—$C_1$-$C_8$ alkyl, —(C=O)—$C_1$-$C_8$ haloalkyl, —(C=O)—$NH_2$, —(C=O)—$NHC_1$-$C_8$ alkyl, —(C=O)—$NHC_1$-$C_8$ haloalkyl, —(C=O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_{20}$ and $R_{21}$ and the nitrogen atom to which they are attached, —(C=O)—$OC_1$-$C_8$ alkyl, —(C=O)—$OC_1$-$C_8$ haloalkyl, —$S(O)_2C_1$-$C_8$ alkyl, —$S(O)_2$ aryl, and —$S(O)_2$;

with the provisos that when $R_1$ and $R_2$ are —OMe and $R_3$ is -Me, then either $R_4$ is neither —H nor —OH, or X is neither —OH nor —$(CH_2)_2C(CH_3)_2OH$;

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, X is —OH or

In another embodiment, the one or more compounds are selected from compounds of the formula:

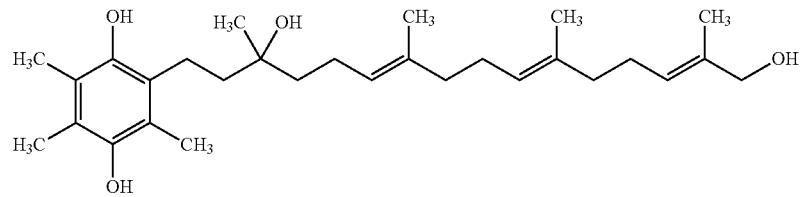

or

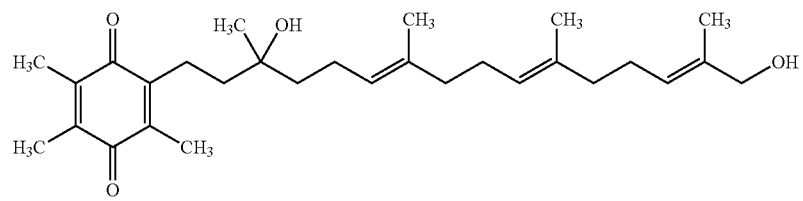

or

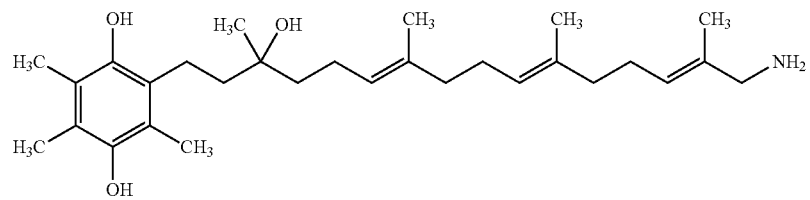

or

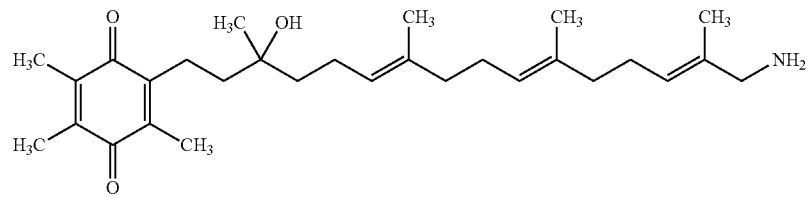

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, X is —$(CH_2)_2C(CH_3)_2OH$. In another embodiment, the compound is selected from

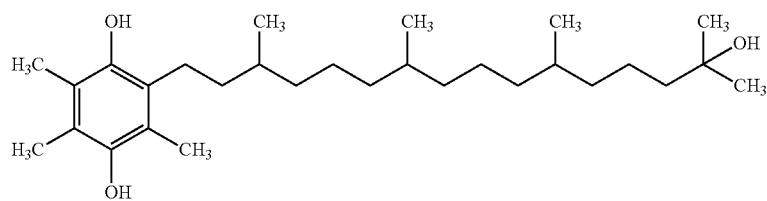

or

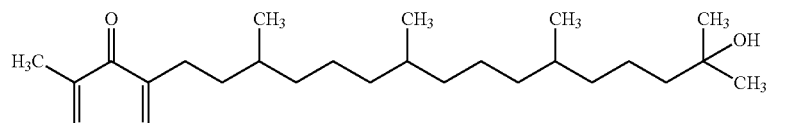

or

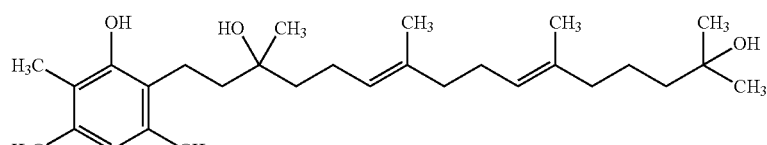

or

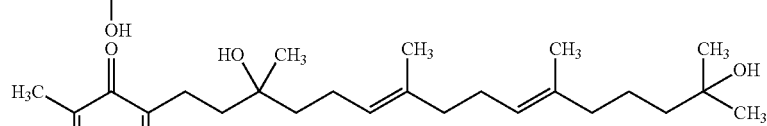

or

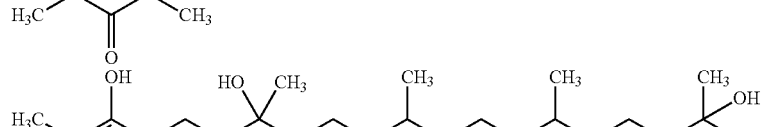

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, the invention embraces compounds of the formula:

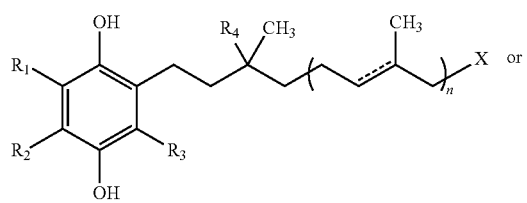

or

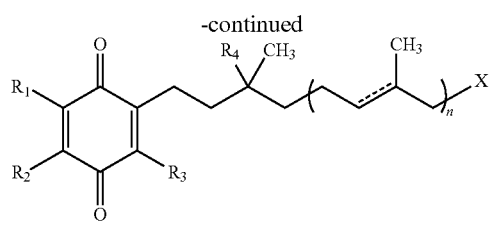

where n is an integer from 0 to 9 inclusive, and each unit can be the same or different;

wherein the bonds indicated with dashed lines can be single or double;

wherein $R_1$, $R_2$ and $R_3$ are independently selected from —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl, with the proviso that when $R_2$ is —$C_1$-$C_5$ alkyl and $R_1$ is —H, then $R_3$ is not —H;

where $R_4$ is selected from the group consisting of F, Cl, and I; where X is selected from the group consisting of —H, —$NR_7R_8$, —$OR_9$, and —$(CH_2)_2C(CH_3)_2OH$; where $R_5$ and $R_6$ are independently selected from the group consisting of —H, —$C_1$-$C_5$ alkyl, —$C_3$-$C_6$ cycloalkyl, —$C_1$-$C_5$ haloalkyl, aryl, heteroaryl, —(C=O)—$C_0$-$C_8$ alkyl, and —(C=O)—$C_0$-$C_8$ alkyl-$C_6$-$C_{10}$ aryl-$C_0$-$C_8$ alkyl, or where $R_5$ and $R_6$ selected from these groups are combined to form a ring;

where $R_7$ and $R_8$ are independently selected from —H, —$C_1$-$C_8$ alkyl or —$C_1$-$C_8$ haloalkyl, —(C=O)—$C_1$-$C_8$ alkyl, or where either one of $R_7$ and $R_8$ are independently selected from the group consisting of —(C=O)—$C_1$-$C_8$ haloalkyl, —(C=O)—$NH_2$, —(C=O)—$NHC_1$-$C_8$ alkyl, —(C=O)—$NHC_1$-$C_8$ haloalkyl, —(C=O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_{20}$ and $R_{21}$ and the nitrogen atom to which they are attached, —(C=O)—$OC_1$-$C_8$ alkyl, —(C=O)—$OC_1$-$C_8$ haloalkyl, —$S(O)_2C_1$-$C_8$ alkyl, —$S(O)_2$ aryl, and —$S(O)_2$ aralkyl, and where the other of $R_7$ or $R_8$ is —H, —$C_1$-$C_8$ alkyl or —$C_1$-$C_8$ haloalkyl or where $R_7$ and $R_8$ selected from these groups are combined to form a ring, or where $R_7$ is —$(CH_2)_p$—, $R_8$ is —$(CH_2)_q$—, p and q are independently integers between 0 and 7 inclusive, p+q is between 2 and 7 inclusive, $R_7$ and $R_8$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_7$ and $R_8$ and the nitrogen atom to which they are attached;

where $R_9$ is independently selected from —H, —$C_1$-$C_8$ alkyl or —$C_1$-$C_8$ haloalkyl, —(C=O)—$C_1$-$C_8$ alkyl, —(C=O)—$C_1$-$C_8$ haloalkyl, —(C=O)—$NH_2$, —(C=O)—$NHC_1$-$C_8$ alkyl, —(C=O)—$NHC_1$-$C_8$ haloalkyl, —(C=O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from —NH—, —N($C_1$-$C_4$ alkyl)-, —O—, or —S— can be optionally incorporated in the ring formed by $R_{20}$ and $R_{21}$ and the nitrogen atom to which they are attached, —(C=O)—$OC_1$-$C_8$ alkyl, —(C=O)—$OC_1$-$C_8$ haloalkyl, —$S(O)_2C_1$-$C_8$ alkyl, —$S(O)_2$ aryl, and —$S(O)_2$;

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, the compound is selected from

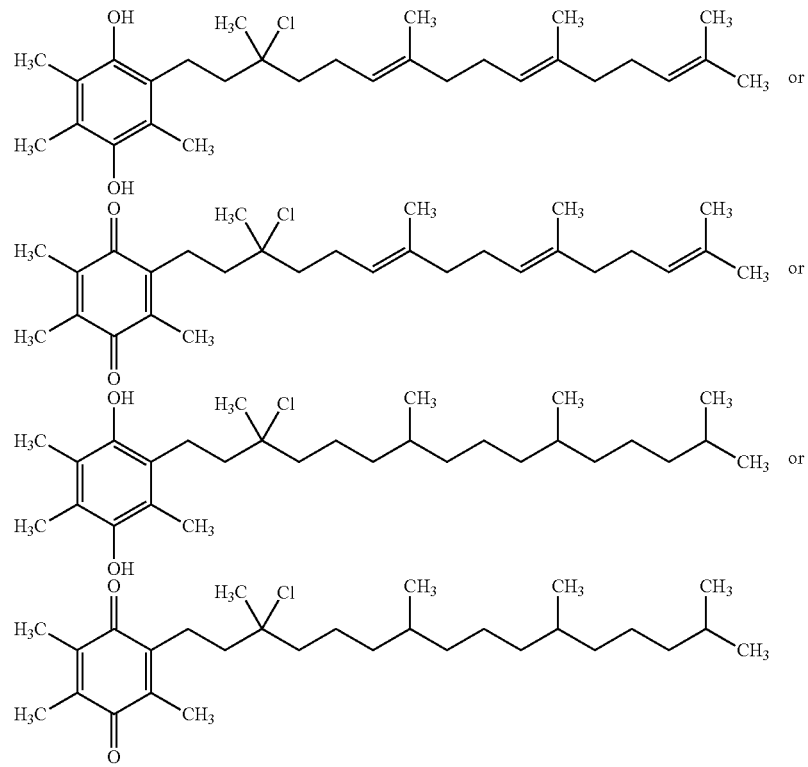

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

In another embodiment, the invention embraces compounds of the formula:

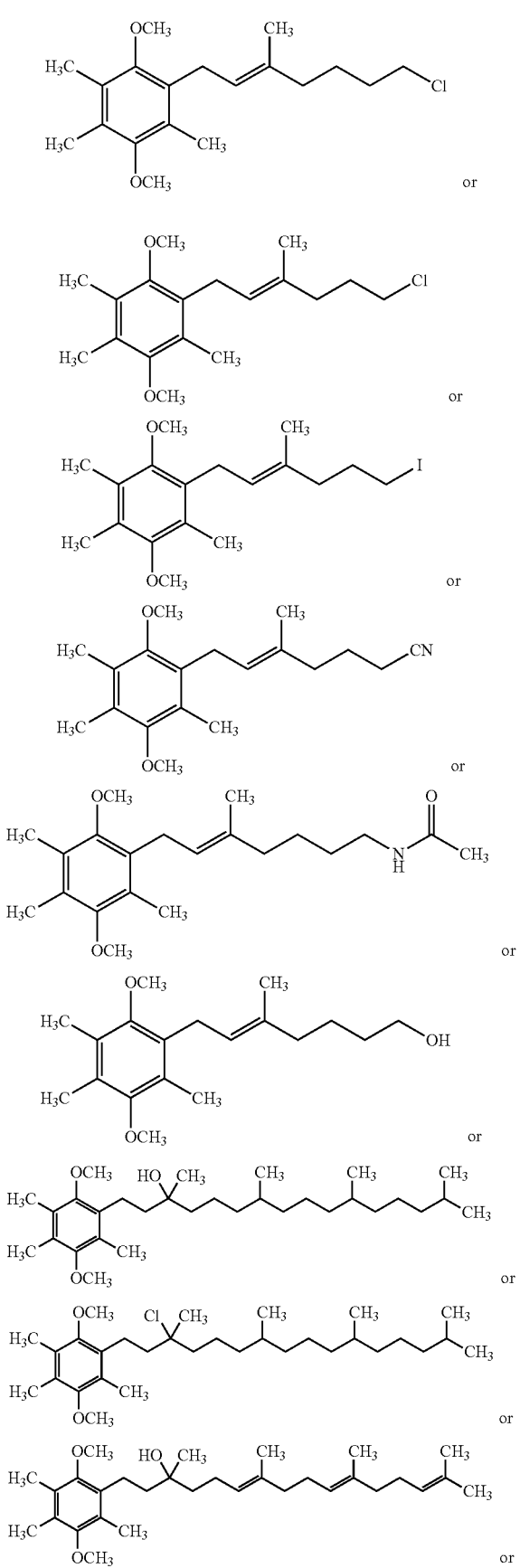

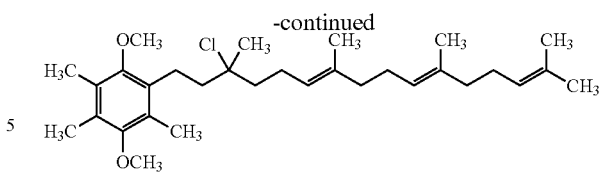

or any stereoisomer, mixture of stereoisomers, prodrug, metabolite, salt, phosphate-substituted form, sulfate-substituted form, phosphate/sulfate substituted form, crystalline form, non-crystalline form, hydrate, or solvate thereof.

For any of the compounds described above, the compound can be combined with a pharmaceutically acceptable excipient.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more compounds as described above.

In another embodiment, the invention embraces a method of treating or suppressing a mitochondrial disorder, modulating one or more energy biomarkers, normalizing one or more energy biomarkers, or enhancing one or more energy biomarkers, by administering a therapeutically effective amount or effective amount of one or more of the compounds described above.

In other embodiments, including any of the foregoing embodiments, the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, Stroke (MELAS); Leber's Hereditary Optic Neuropathy (LHON); Leigh Disease; Kearns-Sayre Syndrome (KSS); Friedreich's Ataxia (FA); other myopathies; cardiomyopathy; encephalomyopathy; renal tubular acidosis; neurodegenerative diseases; Parkinson's disease; Alzheimer's disease; amyotrophic lateral sclerosis (ALS); motor neuron diseases; other neurological diseases; epilepsy; genetic diseases; Huntington's Disease; mood disorders; schizophrenia; bipolar disorder; age-associated diseases; macular degeneration; diabetes; and cancer.

In another embodiment, including any of the foregoing embodiments, the mitochondrial disorder is selected from the group consisting of inherited mitochondrial diseases; Myoclonic Epilepsy with Ragged Red Fibers (MERRF); Mitochondrial Myopathy, Encephalopathy, Lactacidosis, Stroke (MELAS); Leber's Hereditary Optic Neuropathy (LHON); Leigh Disease; Kearns-Sayre Syndrome (KSS); and Friedreich's Ataxia (FA).

In another embodiment of the invention, including any of the foregoing embodiments, the mitochondrial disorder is Friedreich's ataxia (FRDA). In another embodiment of the invention, the mitochondrial disorder is Leber's Hereditary Optic Neuropathy (LHON). In another embodiment of the invention, the mitochondrial disorder is mitochondrial myopathy, encephalopathy, lactacidosis, stroke (MELAS). In another embodiment of the invention, the mitochondrial disorder is Kearns-Sayre Syndrome (KSS). In another embodiment of the invention, the mitochondrial disorder is Myoclonic Epilepsy with Ragged Red Fibers (MERRF). In another embodiment of the invention, the mitochondrial disorder is Parkinson's disease.

In another embodiment of the invention, including any of the foregoing embodiments, the compounds described herein are administered to subjects suffering from a mitochondrial disorder to modulate one or more of various energy biomarkers, including, but not limited to, lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH (NADH+H$^+$) or NADPH (NADPH+H$^+$) levels; NAD or NADP levels; ATP levels; reduced coenzyme Q (CoQ$^{red}$) levels; oxidized coenzyme Q (CoQ$^{ox}$) levels; total coenzyme Q (CoQ$^{tot}$) levels; oxidized cytochrome C levels; reduced cytochrome C levels; oxidized cytochrome C/reduced cytochrome C ratio; acetoacetate levels; beta-hydroxy butyrate levels; acetoacetate/beta-hydroxy butyrate ratio; 8-hydroxy-2'-deoxyguanosine (8-OHdG) levels; levels of reactive oxygen species; oxygen consumption (VO2), carbon dioxide output (VCO2), respiratory quotient (VCO2/VO2), and to modulate exercise intolerance (or conversely, modulate exercise tolerance) and to modulate anaerobic threshold. Energy biomarkers can be measured in whole blood, plasma, cerebrospinal fluid, cerebroventricular fluid, arterial blood, venous blood, or any other body fluid, body gas, or other biological sample useful for such measurement. In one embodiment, the levels are modulated to a value within about 2 standard deviations of the value in a healthy subject. In another embodiment, the levels are modulated to a value within about 1 standard deviation of the value in a healthy subject. In another embodiment, the levels in a subject are changed by at least about 10% above or below the level in the subject prior to modulation. In another embodiment, the levels are changed by at least about 20% above or below the level in the subject prior to modulation. In another embodiment, the levels are changed by at least about 30% above or below the level in the subject prior to modulation. In another embodiment, the levels are changed by at least about 40% above or below the level in the subject prior to modulation. In another embodiment, the levels are changed by at least about 50% above or below the level in the subject prior to modulation. In another embodiment, the levels are changed by at least about 75% above or below the level in the subject prior to modulation. In another embodiment, the levels are changed by at least about 100% above or at least about 90% below the level in the subject prior to modulation.

In another embodiment, including any of the foregoing embodiments, the subject or subjects in which a method of treating or suppressing a mitochondrial disorder, modulating one or more energy biomarkers, normalizing one or more energy biomarkers, or enhancing one or more energy biomarkers is performed is/are selected from the group consisting of subjects undergoing strenuous or prolonged physical activity; subjects with chronic energy problems; subjects with chronic respiratory problems; pregnant females; pregnant females in labor; neonates; premature neonates; subjects exposed to extreme environments; subjects exposed to hot environments; subjects exposed to cold environments; subjects exposed to environments with lower-than-average oxygen content; subjects exposed to environments with higher-than-average carbon dioxide content; subjects exposed to environments with higher-than-average levels of air pollution; airline travelers; flight attendants; subjects at elevated altitudes; subjects living in cities with lower-than-average air quality; subjects working in enclosed environments where air quality is degraded; subjects with lung diseases; subjects with lower-than-average lung capacity; tubercular patients; lung cancer patients; emphysema patients; cystic fibrosis patients; subjects recovering from surgery; subjects recovering from illness; elderly subjects; elderly subjects experiencing decreased energy; subjects suffering from chronic fatigue; subjects suffering from chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

In another embodiment, the invention embraces one or more compounds described herein in combination with a pharmaceutically acceptable excipient, carrier, or vehicle.

In another embodiment, the invention embraces the use of one or more compounds described herein in therapy. In another embodiment, the invention embraces the use of one or more compounds described herein in the therapy of mitochondrial disease. In another embodiment, the invention embraces the use of one or more compounds described herein in the manufacture of a medicament for use in therapy of mitochondrial disease.

For all of the compounds and methods described above, the quinone form can also be used in its reduced (hydroquinone) form when desired. Likewise, the hydroquinone form can also be used in its oxidized (quinone) form when desired.

For all of the compounds and methods described above, $R_1$, $R_2$, and $R_3$, when present, can be selected from the group consisting of H and $C_1$-$C_5$ alkyl, or from $C_1$-$C_5$ alkyl.

MODES FOR CARRYING OUT THE INVENTION

The invention embraces compounds useful in treating or suppressing mitochondrial disorders, and methods of using such compounds for modulation of energy biomarkers. The redox active therapeutics for treatment or suppression of mitochondrial diseases and associated aspects of the invention are described in more detail herein.

By "subject," "individual," or "patient" is meant an individual organism, preferably a vertebrate, more preferably a mammal, most preferably a human.

"Treating" a disease with the compounds and methods discussed herein is defined as administering one or more of the compounds discussed herein, with or without additional therapeutic agents, in order to reduce or eliminate either the disease or one or more symptoms of the disease, or to retard the progression of the disease or of one or more symptoms of the disease, or to reduce the severity of the disease or of one or more symptoms of the disease. "Suppression" of a disease with the compounds and methods discussed herein is defined as administering one or more of the compounds discussed herein, with or without additional therapeutic agents, in order to suppress the clinical manifestation of the disease, or to suppress the manifestation of adverse symptoms of the disease. The distinction between treatment and suppression is that treatment occurs after adverse symptoms of the disease are manifest in a subject, while suppression occurs before adverse symptoms of the disease are manifest in a subject. Suppression may be partial, substantially total, or total. Because many of the mitochondrial disorders are inherited, genetic screening can be used to identify patients at risk of the disease. The compounds and methods of the invention can then be administered to asymptomatic patients at risk of developing the clinical symptoms of the disease, in order to suppress the appearance of any adverse symptoms. "Therapeutic use" of the compounds discussed herein is defined as using one or more of the compounds discussed herein to treat or suppress a disease, as defined above. An "effective amount" of a compound is an amount of the compound sufficient to modulate, normalize, or enhance one or more energy biomarkers (where modulation, normalization, and enhancement are defined below). A "therapeutically effective amount" of a compound is an amount of the compound, which, when administered to a subject, is sufficient to reduce or eliminate either a disease or one or more symptoms of a disease, or to retard the progression of a disease or of one or more symptoms of a disease, or to reduce the severity of a disease or of one or more symptoms of a disease, or to suppress the clinical manifestation of a disease, or to suppress the manifestation of adverse symptoms of a disease. A therapeutically effective amount can be given in one or more administrations. An "effective amount" of a compound embraces both a therapeutically effective amount, as well as an amount effective to modulate, normalize, or enhance one or more energy biomarkers in a subject.

"Modulation" of, or to "modulate," an energy biomarker means to change the level of the energy biomarker towards a desired value, or to change the level of the energy biomarker in a desired direction (e.g., increase or decrease). Modulation can include, but is not limited to, normalization and enhancement as defined below.

"Normalization" of, or to "normalize," an energy biomarker is defined as changing the level of the energy biomarker from a pathological value towards a normal value, where the normal value of the energy biomarker can be 1) the level of the energy biomarker in a healthy person or subject, or 2) a level of the energy biomarker that alleviates one or more undesirable symptoms in the person or subject. That is, to normalize an energy biomarker which is depressed in a disease state means to increase the level of the energy biomarker towards the normal (healthy) value or towards a value which alleviates an undesirable symptom; to normalize an energy biomarker which is elevated in a disease state means to decrease the level of the energy biomarker towards the normal (healthy) value or towards a value which alleviates an undesirable symptom.

"Enhancement" of, or to "enhance," energy biomarkers means to intentionally change the level of one or more energy biomarkers away from either the normal value, or the value before enhancement, in order to achieve a beneficial or desired effect. For example, in a situation where significant energy demands are placed on a subject, it may be desirable to increase the level of ATP in that subject to a level above the normal level of ATP in that subject. Enhancement can also be of beneficial effect in a subject suffering from a disease or pathology such as a mitochondrial disease, in that normalizing an energy biomarker may not achieve the optimum outcome for the subject; in such cases, enhancement of one or more energy biomarkers can be beneficial, for example, higher-than-normal levels of ATP, or lower-than-normal levels of lactic acid (lactate) can be beneficial to such a subject.

By modulating, normalizing, or enhancing the energy biomarker Coenzyme Q is meant modulating, normalizing, or enhancing the variant or variants of Coenzyme Q which is predominant in the species of interest. For example, the variant of Coenzyme Q which predominates in humans is Coenzyme Q10. If a species or subject has more than one variant of Coenzyme Q present in significant amounts (i.e., present in amounts which, when modulated, normalized, or enhanced, can have a beneficial effect on the species or subject), modulating, normalizing, or enhancing Coenzyme Q can refer to modulating, normalizing or enhancing any or all variants of Coenzyme Q present in the species or subject.

While the compounds described herein can occur and can be used as the neutral (non-salt) compound, the description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts. Salts of acidic compounds with amino acids, such as lysine salts, can also be prepared.

The invention also includes all stereoisomers and geometric isomers of the compounds, including diastereomers, enantiomers, and cis/trans (E/Z) isomers. The invention also includes mixtures of stereoisomers and/or geometric isomers in any ratio, including, but not limited to, racemic mixtures.

The compounds can be administered in prodrug form. Prodrugs are derivatives of the compounds which are themselves relatively inactive, but which convert into the active compound when introduced into the subject in which they are used, by a chemical or biological process in vivo, such as an enzymatic conversion. Suitable prodrug formulations include, but are not limited to, peptide conjugates of the compounds of the invention and esters of compounds of the inventions. Further discussion of suitable prodrugs is provided in H. Bundgaard, Design of Prodrugs, New York: Elsevier, 1985; in R. Silverman, The Organic Chemistry of Drug Design and Drug Action, Boston: Elsevier, 2004; in R. L. Juliano (ed.), Biological Approaches to the Controlled Delivery of Drugs (Annals of the New York Academy of Sciences, v. 507), New York: New York Academy of Sciences, 1987; and in E. B. Roche (ed.), Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.), Washington: The Academy, 1977.

The invention includes derivatives of compounds described herein substituted with one or more phosphate groups and/or sulfate groups. A compound is "phosphate-substituted" when it contains one or more phosphate groups and is "sulfate-substituted" when it contains one or more sulfate groups. A "phosphate/sulfate substituted" compound contains at least one phosphate and at least one sulfate group. For example, one or more hydroxyl groups of a phenyl ring may be substituted to form a compound such as:

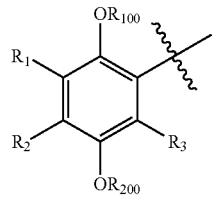

wherein $R_1$, $R_2$, and $R_3$ are as described herein and where $R_{100}$ and $R_{200}$ can be independently selected from —H, —$PO_3^{2-}$, and —$SO_3^-$. In one embodiment, the invention embraces compounds where $R_{100}$ is —H and $R_{200}$ is —$PO_3^{2-}$. In another embodiment, the invention embraces compounds where $R_{100}$ is —H and $R_{200}$ is —$SO_3^-$. In another embodiment, the invention embraces compounds where $R_{100}$ is —$SO_3^-$ and $R_{200}$ is —$PO_3^{2-}$. In another embodiment, the invention embraces compounds where $R_{100}$ is —$PO_3^{2-}$ and $R_{200}$ is —$SO_3^-$. In another embodiment, the invention embraces compounds where $R_{100}$ is —$PO_3^{2-}$ and $R_{200}$ is —H. In another embodiment, the invention embraces compounds where $R_{100}$ is —$SO_3^-$ and $R_{200}$ is —H. In another embodiment, the invention embraces compounds where $R_{100}$ and $R_{200}$ are —$PO_3^{2-}$. In another embodiment, the invention embraces compounds where $R_{100}$ and $R_{200}$ are —$SO_3^-$. Additionally included in this invention are all protonated or partially protonated forms and salts thereof of compounds substituted with phosphates and/or sulfates.

The various compounds of the invention can be administered either as therapeutic agents in and of themselves, or as prodrugs which will convert to other therapeutically effective or effective substances in the body.

Metabolites of the compounds are also embraced by the invention. However, metabolites of substances which occur naturally in subjects are excluded from the claimed compounds of the invention.

The term "alkyl" refers to saturated aliphatic groups including straight-chain, branched-chain, cyclic groups, and combinations thereof, having the number of carbon atoms specified, or if no number is specified, having up to 12 carbon atoms. "Straight-chain alkyl" or "linear alkyl" groups refers to alkyl groups that are neither cyclic nor branched, commonly designated as "n-alkyl" groups. Examples of alkyl groups include, but are not limited to, groups such as methyl, ethyl, n-propyl, isopropyl, butyl, n-butyl, isobutyl, sec-butyl, t-butyl, pentyl, n-pentyl, hexyl, heptyl, octyl, nonyl, decyl, undecyl, dodecyl, neopentyl, cyclopropyl, cyclobutyl, cyclopentyl, cyclohexyl, and adamantyl. Cycloalkyl groups can consist of one ring, including, but not limited to, groups such as cycloheptyl, or multiple fused rings, including, but not limited to, groups such as adamantyl or norbornyl. One preferred subset of alkyl groups is $C_1$-$C_5$ alkyl, which is intended to embrace methyl (Me), ethyl (Et), propyl (Pr), n-propyl (nPr), isopropyl (iPr), butyl (Bu), n-butyl (nBu), isobutyl (iBu), sec-butyl (sBu), t-butyl (tBu), cyclopropyl (cyclPr), cyclobutyl (cyclBu), cyclopropyl-methyl (cyclPr-Me), methyl-cyclopropane (Me-cyclPr), pentyl, n-pentyl, isopentyl, neopentyl, sec-pentyl, t-pentyl, 1,2-dimethylpropyl, cyclopentyl, and any other alkyl group containing between one and five carbon atoms, where the $C_1$-$C_5$ alkyl groups can be attached via any valence on the $C_1$-$C_5$ alkyl groups.

Note that "$C_0$ alkyl," when it appears, is intended to mean either a non-existent group, or a hydrogen, which will be understood by the context in which it appears. When a $C_0$ alkyl group appears as the terminal group on a chain, as for example in —(C=O)—$C_0$ alkyl, it is intended as a hydrogen atom; thus, —(C=O)—$C_0$ alkyl is intended to represent —(C=O)—H (an aldehyde). When a $C_0$ alkyl group appears between two other groups, as, for example, in —(C=O)—$C_0$ alkyl-$C_6$-$C_{10}$ aryl, it is intended to be a nonentity, thus —(C=O)—$C_0$ alkyl-$C_6$-$C_{10}$ aryl represents —(C=O)—$C_6$-$C_{10}$ aryl.

"Substituted alkyl" refers to alkyl groups substituted with one or more substituents including, but not limited to, groups such as halogen (fluoro, chloro, bromo, and iodo), alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of substituted alkyl groups include, but are not limited to, groups such as —$CH_2$—OH; —$CH_2CH_2CH(NH_2)CH_3$, etc. The substituent(s) on the substituted alkyl group may be at any available location on the group. Substituted alkyl embraces the preferred subset of $C_1$-$C_5$ haloalkyl, which is intended to embrace any $C_1$-$C_5$ alkyl substituent having at least one halogen substituent; the halogen can be attached via any available valence on the $C_1$-$C_5$ alkyl group. One further subset of $C_1$-$C_5$ haloalkyl is —$CF_3$, —$CCl_3$, —$CBr_3$, and —$CI_3$. Another further subset of $C_1$-$C_5$ haloalkyl is the subset with exactly one halogen substituent. Another further subset of $C_1$-$C_5$ haloalkyl is the subset with exactly one chloro substituent. Another further subset of $C_1$-$C_5$ haloalkyl is the subset with exactly one fluoro substituent. Another further subset of $C_1$-$C_5$ haloalkyl is the subset of $C_1$-$C_5$ perhaloalkyl; that is, $C_1$-$C_5$ alkyl with all available valences replaced by halogens. Another further subset of $C_1$-$C_5$ haloalkyl is the subset of $C_1$-$C_5$ perfluoroalkyl; that is, $C_1$-$C_5$ alkyl with all available valences replaced by fluorines, such as —$CF_3$ and —$CF_2$—$CF_3$. Another further subset of $C_1$-$C_5$ haloalkyl is the subset of $C_1$-$C_5$ perchloroalkyl; that is, $C_1$-$C_5$ alkyl with all available valences replaced by chlorines.

The term "alkenyl" refers to unsaturated aliphatic groups including straight-chain (linear), branched-chain, cyclic groups, and combinations thereof, having the number of carbon atoms specified, or if no number is specified, having up to 12 carbon atoms, which contain at least one double bond (—C=C—). All double bonds may be independently either (E) or (Z) geometry, as well as arbitrary mixtures thereof. Examples of alkenyl groups include, but are not limited to, —$CH_2$—CH=CH—$CH_3$; and —$CH_2$—$CH_2$-cyclohexenyl, where the ethyl group can be attached to the cyclohexenyl moiety at any available carbon valence.

"Haloalkenyl" embraces any $C_1$-$C_5$ alkenyl substituent having at least one halogen substituent; the halogen can be attached via any available valence on the $C_1$-$C_5$ alkenyl group. One further subset of $C_1$-$C_5$ haloalkenyl is the subset with exactly one halogen substituent. Another further subset of $C_1$-$C_5$ haloalkenyl is the subset with exactly one chloro substituent. Another further subset of $C_1$-$C_5$ haloalkenyl is the subset with exactly one fluoro substituent. Another further subset of $C_1$-$C_5$ haloalkenyl is the subset of $C_1$-$C_5$ perhaloalkenyl; that is, $C_1$-$C_5$ alkenyl with all available valences replaced by halogens. Another further subset of $C_1$-$C_5$ haloalkenyl is the subset of $C_1$-$C_5$ perfluoroalkenyl;

that is, $C_1$-$C_5$ alkenyl with all available valences replaced by fluorines. Another further subset of $C_1$-$C_5$ haloalkenyl is the subset of $C_1$-$C_5$ perchloroalkenyl; that is, $C_1$-$C_5$ alkenyl with all available valences replaced by chlorines.

The term "alkynyl" refers to unsaturated aliphatic groups including straight-chain (linear), branched-chain, cyclic groups, and combinations thereof, having the number of carbon atoms specified, or if no number is specified, having up to 12 carbon atoms, which contain at least one triple bond (—C≡C—). "Hydrocarbon chain" or "hydrocarbyl" refers to any combination of straight-chain, branched-chain, or cyclic alkyl, alkenyl, or alkynyl groups, and any combination thereof. "Substituted alkenyl," "substituted alkynyl," and "substituted hydrocarbon chain" or "substituted hydrocarbyl" refer to the respective group substituted with one or more substituents, including, but not limited to, groups such as halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

"Haloalkynyl" embraces any $C_1$-$C_5$ alkynyl substituent having at least one halogen substituent; the halogen can be attached via any available valence on the $C_1$-$C_5$ alkynyl group. One further subset of $C_1$-$C_5$ haloalkynyl is the subset with exactly one halogen substituent. Another further subset of $C_1$-$C_5$ haloalkynyl is the subset with exactly one chloro substituent. Another further subset of $C_1$-$C_5$ haloalkynyl is the subset with exactly one fluoro substituent. Another further subset of $C_1$-$C_5$ haloalkynyl is the subset of $C_1$-$C_5$ perhaloalkynyl; that is, $C_1$-$C_5$ alkynyl with all available valences replaced by halogens. Another further subset of $C_1$-$C_5$ haloalkynyl is the subset of $C_1$-$C_5$ perfluoroalkynyl; that is, $C_1$-$C_5$ alkynyl with all available valences replaced by fluorines. Another further subset of $C_1$-$C_5$ haloalkynyl is the subset of $C_1$-$C_5$ perchloroalkynyl; that is, $C_1$-$C_5$ alkynyl with all available valences replaced by chlorines.

"Aryl" or "Ar" refers to an aromatic group having a single ring (including, but not limited to, groups such as phenyl) or two or more condensed rings (including, but not limited to, groups such as naphthyl or anthryl), and includes both unsubstituted and substituted aryl groups. Aryls, unless otherwise specified, contain from 6 to 12 carbon atoms in the ring portion. A preferred range for aryls is from 6 to 10 carbon atoms in the ring portion. "Substituted aryls" refers to aryls substituted with one or more substituents, including, but not limited to, groups such as alkyl, alkenyl, alkynyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. "Aralkyl" designates an alkyl-substituted aryl group, where any aryl can attached to the alkyl; the alkyl portion is a straight or branched chain of 1 to 6 carbon atoms, preferably the alkyl chain contains 1 to 3 carbon atoms. When an aralkyl group is indicated as a substituent, the aralkyl group can be connected to the remainder of the molecule at any available valence on either its alkyl moiety or aryl moiety; e.g., the tolyl aralkyl group can be connected to the remainder of the molecule by replacing any of the five hydrogens on the aromatic ring moiety with the remainder of the molecule, or by replacing one of the alpha-hydrogens on the methyl moiety with the remainder of the molecule. Preferably, the aralkyl group is connected to the remainder of the molecule via the alkyl moiety.

A preferred aryl group is phenyl, which can be substituted or unsubstituted. Examples of substituents for substituted phenyl groups include, but are not limited to, alkyl, halogen (chlorine (—Cl), bromine (—Br), iodine (—I), or fluorine (—F)), hydroxy (—OH), or alkoxy (such as methoxy, ethoxy, n-propoxy or i-propoxy, n-butoxy, i-butoxy, sec-butoxy, or tert-butoxy). Substituted phenyl groups preferably have one or two substituents; more preferably, one substituent.

"Heteroalkyl," "heteroalkenyl," and "heteroalkynyl" refer to alkyl, alkenyl, and alkynyl groups, respectively, that contain the number of carbon atoms specified (or if no number is specified, having up to 12 carbon atoms) which contain one or more heteroatoms as part of the main, branched, or cyclic chains in the group. Heteroatoms include, but are not limited to, N, S, O, and P; N and O are preferred. Heteroalkyl, heteroalkenyl, and heteroalkynyl groups may be attached to the remainder of the molecule either at a heteroatom (if a valence is available) or at a carbon atom. Examples of heteroalkyl groups include, but are not limited to, groups such as —O—CH$_3$, —CH$_2$—O—CH$_3$, —CH$_2$—CH$_2$—O—CH$_3$, —S—CH$_2$—CH$_2$—CH$_3$, —CH$_2$—CH(CH$_3$)—S—CH$_3$, —CH$_2$—CH$_2$—NH—CH$_2$—CH$_2$—, 1-ethyl-6-propylpiperidino, and morpholino. Examples of heteroalkenyl groups include, but are not limited to, groups such as —CH═CH—NH—CH(CH$_3$)—CH$_2$—. "Heteroaryl" or "HetAr" refers to an aromatic group having a single ring (including, but not limited to, examples such as pyridyl, imidazolyl, thiophene, or furyl) or two or more condensed rings (including, but not limited to, examples such as indolizinyl or benzothienyl) and having at least one hetero atom, including, but not limited to, heteroatoms such as N, O, P, or S, within the ring. Unless otherwise specified, heteroalkyl, heteroalkenyl, heteroalkynyl, and heteroaryl groups have between one and five heteroatoms and between one and twelve carbon atoms. "Substituted heteroalkyl," "substituted heteroalkenyl," "substituted heteroalkynyl," and "substituted heteroaryl" groups refer to heteroalkyl, heteroalkenyl, heteroalkynyl, and heteroaryl groups substituted with one or more substituents, including, but not limited to, groups such as alkyl, alkenyl, alkynyl, benzyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of such substituted heteroalkyl groups include, but are not limited to, piperazine, substituted at a nitrogen or carbon by a phenyl or benzyl group, and attached to the remainder of the molecule by any available valence on a carbon or nitrogen, —NH—SO$_2$-phenyl, —NH—(C═O)O-alkyl, —NH—(C═O)O-alkyl-aryl, and —NH—(C═O)-alkyl. If chemically possible, the heteroatom(s) and/or the carbon atoms of the group can be substituted. The heteroatom(s) can also be in oxidized form, if chemically possible.

The term "alkoxy" as used herein refers to an alkyl, alkenyl, alkynyl, or hydrocarbon chain linked to an oxygen atom and having the number of carbon atoms specified, or if no number is specified, having up to 12 carbon atoms. Examples of alkoxy groups include, but are not limited to, groups such as methoxy, ethoxy, propyloxy (propoxy) (either n-propoxy or i-propoxy), and butoxy (either n-butoxy, i-butoxy, sec-butoxy, or tert-butoxy). The groups listed in the preceding sentence are preferred alkoxy groups; a particularly preferred alkoxy substituent is methoxy.

The terms "halo" and "halogen" as used herein refer to the Group VIIa elements (Group 17 elements in the 1990 IUPAC Periodic Table, IUPAC Nomenclature of Inorganic Chemistry, Recommendations 1990) and include Cl, Br, F and I substituents. Preferred halogen substituents are Cl and F.

When fragments, such as alkyl fragments, heteroaryl fragments, etc., are indicated as substituents, the substituent fragment can be attached to the remainder of the molecule at any point on the fragment where chemically possible (i.e., by using any available valence at a given point of the fragment, such as a valence made available by removing one or more hydrogen atoms from the fragment) unless otherwise specified. For example, in the fragment —(C═O)—$C_0$-$C_8$ alkyl-$C_6$-$C_{10}$ aryl-$C_0$-$C_8$ alkyl, if the leftmost $C_0$-$C_8$ alkyl group is a $C_3$ alkyl group, it can be attached to the sp² carbon of the carbonyl group at any of the three carbon atoms in the chain, unless otherwise specified. Likewise, the $C_6$-$C_{10}$ aryl group can be attached to the alkyl groups at any carbons in the aryl group, unless otherwise specified.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis,* 3rd Ed. (John Wiley & Sons, Inc., New York). Amino protecting groups include, but are not limited to, mesitylenesulfonyl (Mts), benzyloxycarbonyl (CBz or Z), t-butyloxycarbonyl (Boc), t-butyldimethylsilyl (TBS or TBDMS), 9-fluorenylmethyloxycarbonyl (Fmoc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, α-,α-dimethyl-dimethoxybenzyloxycarbonyl (DDZ), 5-bromo-7-nitroindolinyl, and the like. Hydroxyl protecting groups include, but are not limited to, Fmoc, TBS, photolabile protecting groups (such as nitroveratryl oxymethyl ether (Nvom)), Mom (methoxy methyl ether), and Mem (methoxy ethoxy methyl ether), NPEOC (4-nitrophenethyloxycarbonyl) and NPEOM (4-nitrophenethyloxymethyloxycarbonyl).

Synthesis of Compounds

The compounds of the invention can be readily synthesized by a variety of methods. Suitable protecting groups for reactions described herein are detailed in the text by Theodora W. Greene and Peter G. M. Wuts, Protective Groups in Organic Synthesis, 3rd edition, Hoboken, N.J.: Wiley-Interscience, 1999. The syntheses below are illustrated with $R_1$, $R_2$, and $R_3$ as methyl; however, the methods are generally applicable when $R_1$, $R_2$, and $R_3$ are selected from other substituents, with suitable protection if necessary.

A method of synthesizing compounds of formula I is by adapting the following synthesis for the compound 1:

which is as follows:

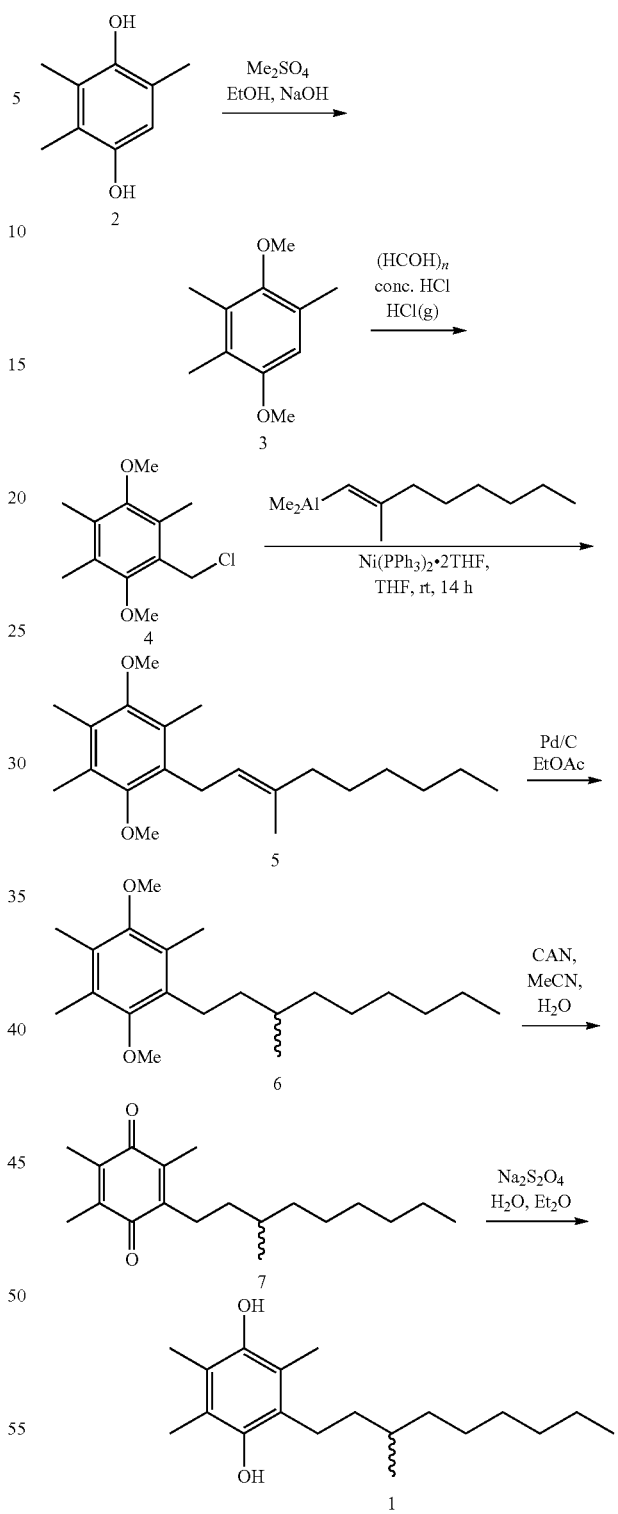

where hydroquinone 2 is dissolved in ethanol and treated with a basic solution of $Me_2SO_4$. Acidic workup and column chromatography yield the dimethyoxy protected hydroquinone 3. The chloromethyl group is introduced by dissolving 3 into a solution of concentrated HCl and paraformaldehyde while adding HCl gas. Neutralization and isolation provide the product 4. Cross-coupling according to the method outlined in Lipshutz, B. H. et. al. *J. Am. Chem. Soc.* 1996, 118, 5512-5513 yields the E-allylated aromatic species 5.

Compound 5 is reduced by Pd/C catalyzed hydrogenation in an appropriate solvent such as EtOH, MeOH, or EtOAc to give a racemic mixture of reduced products 6. The protected hydroquinone is then oxidized to the quinone by treatment with CAN in acetonitrile/water mixtures to give 1,4-benzoquinone 7 directly and subsequently reduced to hydroquinone 1 by treatment of a biphasic mixture of an etherial solvent with a basic aqueous solution of $Na_2S_2O_4$ (Vogel, A. I. et. al. Vogel's Textbook of Practical Organic Chemistry, 5th Edition, Prentice Hall: New York, 1996). Standard workup in the absence of oxygen yields the desired hydroquinone. Single enantiomers are available by substituting the appropriate chiral hydrogenation catalyst (Bell, S. et. al. Science 2006, 311, 642-644) in place of Pd/C.

Another method of making compounds of formula I is by adapting the following synthesis of compound 8 of the form:

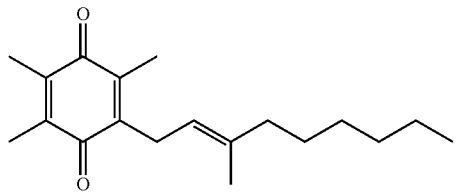

(8)

where precursor 5, prepared as for compound 1, is oxidized to the quinone 8 by treated with CAN in acetonitrile/water. Alternatively, quinone 8 can be prepared directly by coupling with 2-chloromethyl-3,5,6-trimethy-[1,4]-benzoquinone as described in Lipshutz, B. H. et al. Tetrahedron 1998, 54, 1241-1253.

Another method of making compounds of formula I is by adapting the following synthesis of compound 9 of the form:

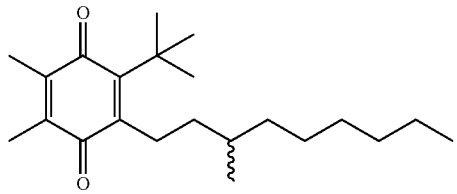

(9)

which is as follows:

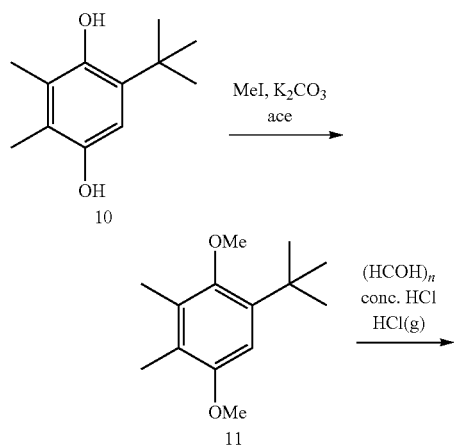

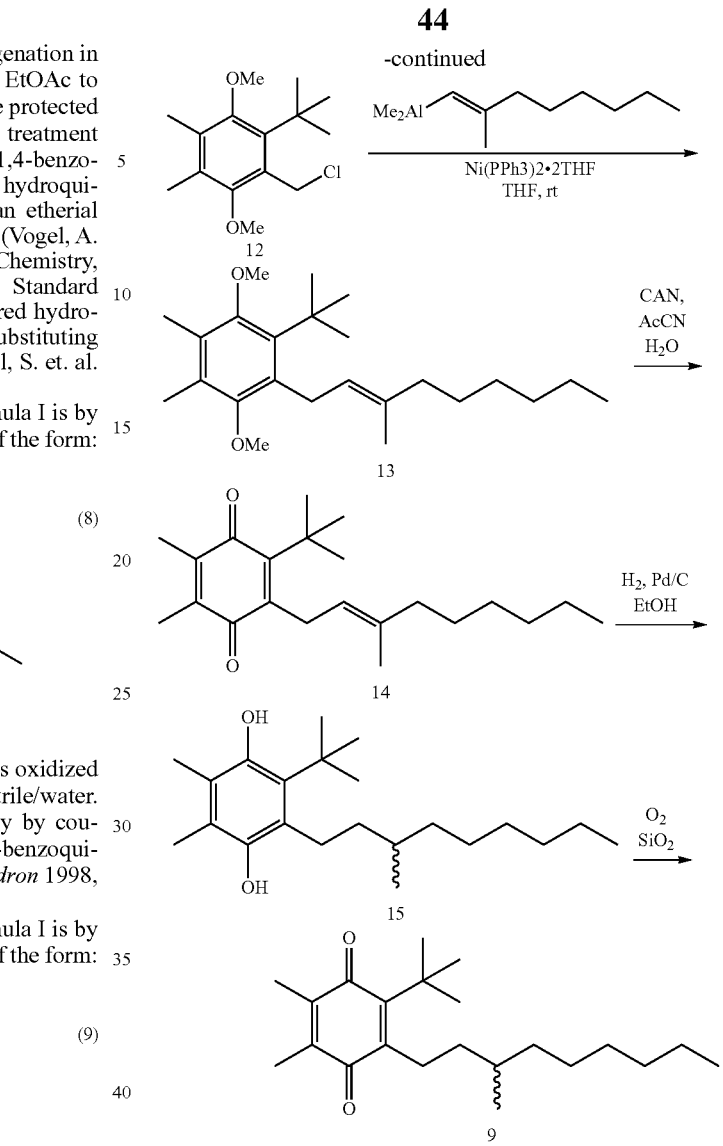

where hydroquinone 10 is methylated using methyliodide to give 11, which is subsequently chloromethylated to provide benzylic chloride 12. This is cross-coupled with the appropriate vinyl alane to give 13. Compound 13 is oxidized using CAN in acetonitrile/water to provide quinone 14, which is then exhaustively reduced by treatment with hydrogen and catalytic palladium on carbon to give hydroquinone. 15. Compound 15 is then oxidized to quinone 9 by exposure to atmospheric oxygen in the presence of silica gel. Alternatively, quinone 14 can be prepared directly by coupling with 2-chloromethyl-3-tertbutyl-5,6-dimethy-[1,4]-benzoquinone as described in Lipshutz, B. H. et al. Tetrahedron 1998, 54, 1241-1253.

Another method of making compounds of formula I is by adapting the following synthesis of compound 16 of the form:

(16)

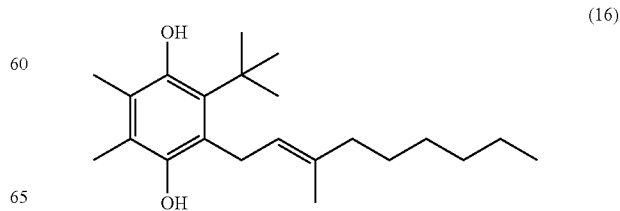

where precursor 14, prepared as with compound 9, is converted to the corresponding hydroquinone 16 by reduction with tin tetrachloride.

A method of synthesizing compounds of formula II is by adapting the following synthesis for the compound 17:

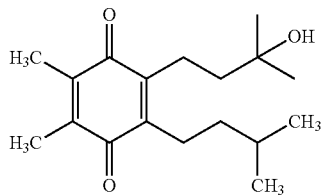
(17)

which is as follows:

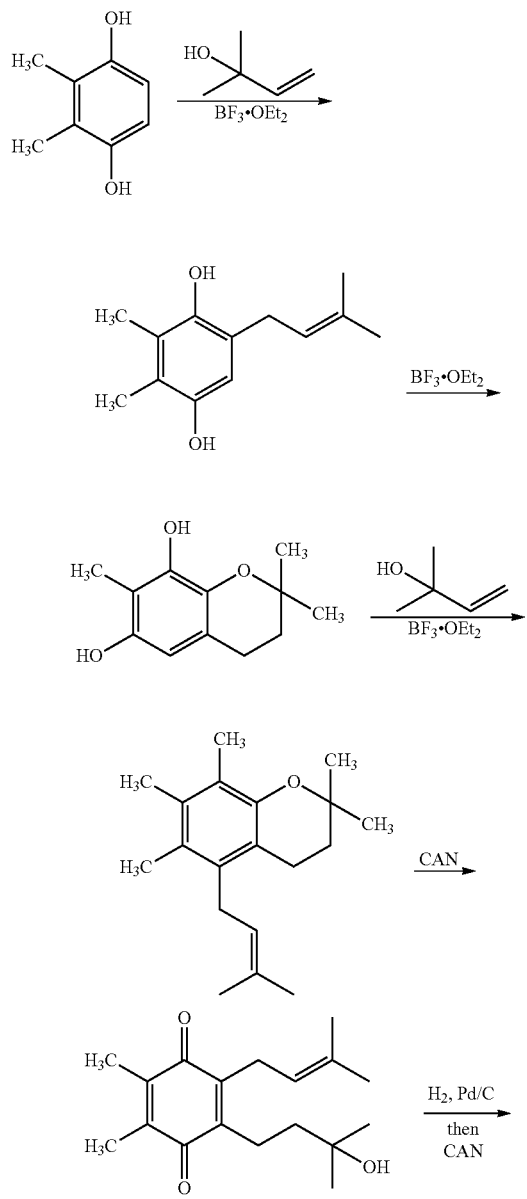

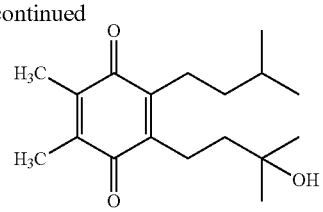
17 where 2,2,7,8-tetramethyl-5-(3-methyl-but-2-enyl)-chroman-6-ol is prepared as described by Walkinshaw, et al., US 2005/0065099 A1, Mar. 24, 2005. Oxidation by treatment with CAN yields the corresponding quinone, which can be exhaustively reduced, followed by reoxidation, to give compound 17.

Another method of making compounds of formula II is by adapting the following synthesis of compound 23 of the form:

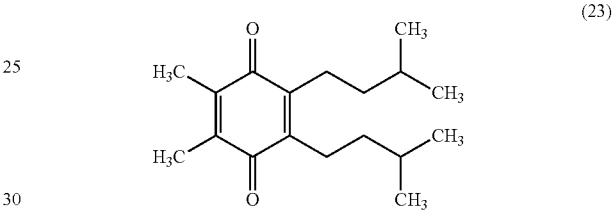
(23)

which is as follows:

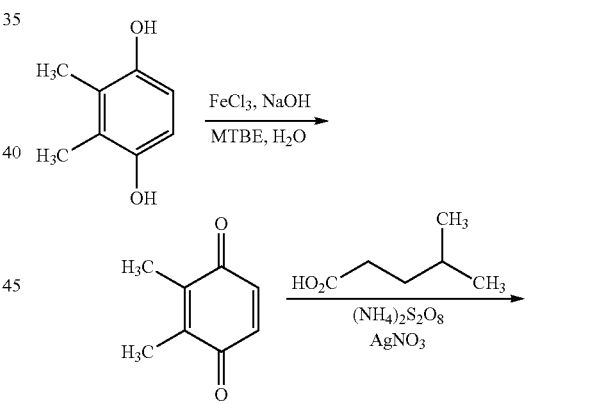

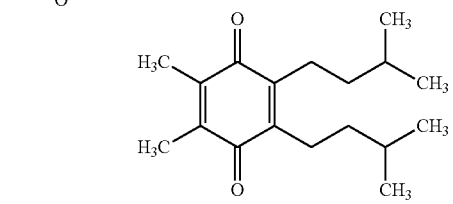
23 where 2,3-dimethy-[1,4]-benzoquinone, prepared by ferric chloride oxidation of 2,3-dimethyl-benzene-1,4-diol, is coupled with 4-methyl pentanoic acid via oxidative decarboxylation mediated by persulfate and silver nitrate to give compound 23 directly.

Another method of making compounds of formula II is by adapting the following synthesis of compound 27 of the form:

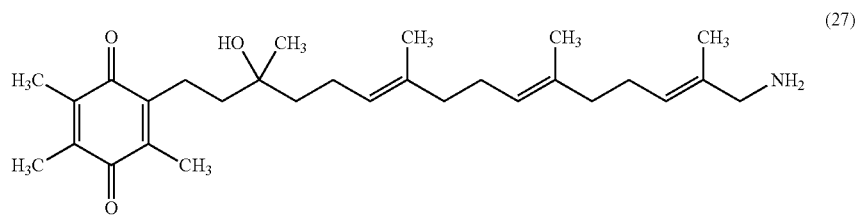 [SMILES: CC1=C(C)C(=O)C(CCC(C)(O)CC/C=C(\C)CC/C=C(\C)CC/C=C(\C)CN)=C(C)C1=O]
(27)
which is as follows:
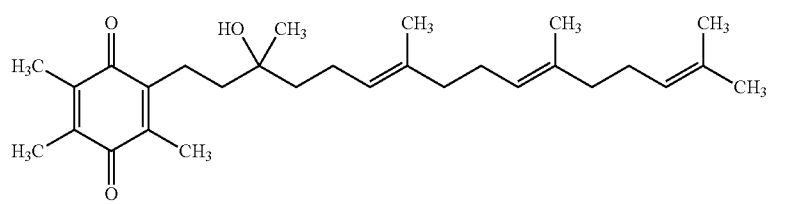
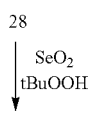
28 | SeO₂
tBuOOH
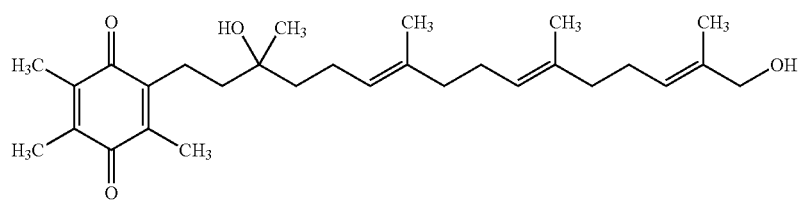
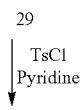
29 | TsCl
Pyridine
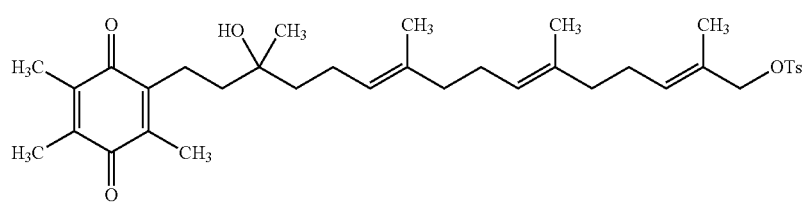
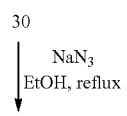
30 | NaN₃
EtOH, reflux
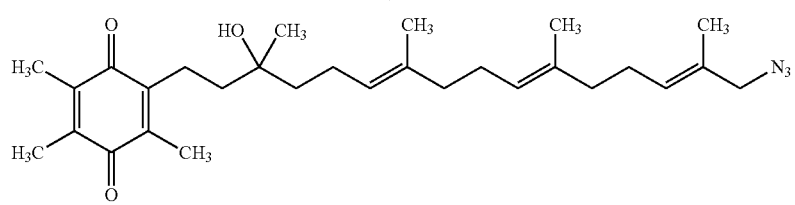
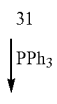
31 | PPh₃

-continued

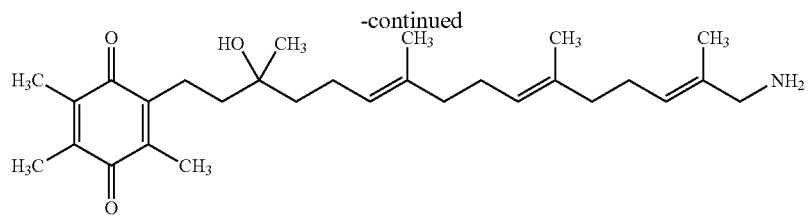

27 where alpha tocotrienol quinone 28 is selectively oxidized with tert-butylhydrogenperoxide and catalytic selenium dioxide according to *Tet. Lett.* 1989, 30(29), 3749-3752 to give allylic alcohol 29. Alcohol 29 is converted to its tosylate using tosyl chloride and pyridine to give 30. Tosylate 30 is displaced using sodium azide in refluxing ethanol to give 31. Azide 31 is reduced selectively using triphenylphosphine to give amine 27.

Another method of making compounds of formula II is by adapting the following synthesis of compound 32 of the form:

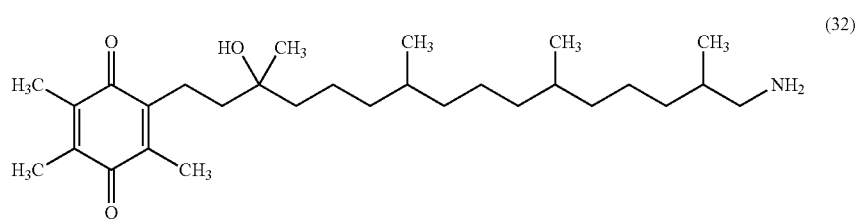 [SMILES: CC1=C(C)C(=O)C(CCC(C)(O)CCCC(C)CCCC(C)CCCC(C)CN)=C(C)C1=O]

(32)

where precursor azide 31, prepared as with compound 27, is treated with hydrogen and catalytic palladium on carbon followed by reoxidation by exposure to atmospheric oxygen in the presence of catalytic $SiO_2$ to give the desired amine.

Another method of making compounds of formula II is by adapting the following synthesis of compound 33 of the form:

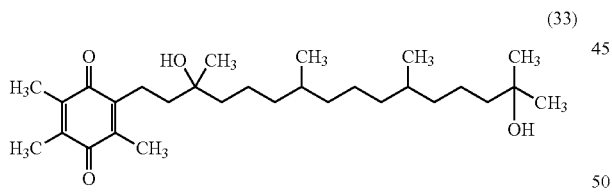

(33)

which is as follows:

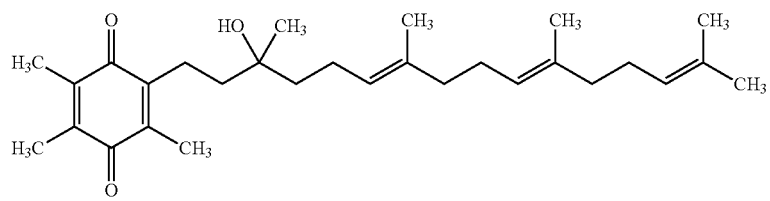

28

1) NBS, DME/$H_2O$
2) $K_2CO_3$

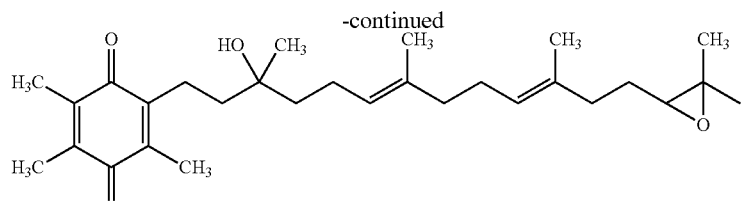

34

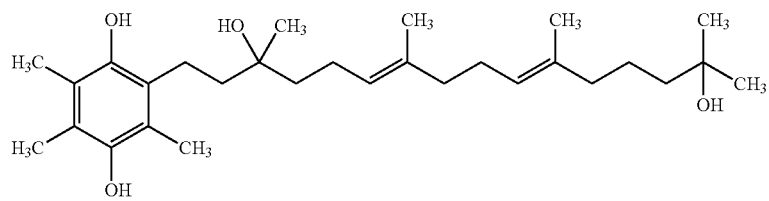

35

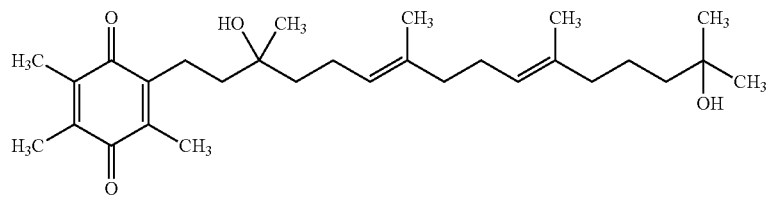

36

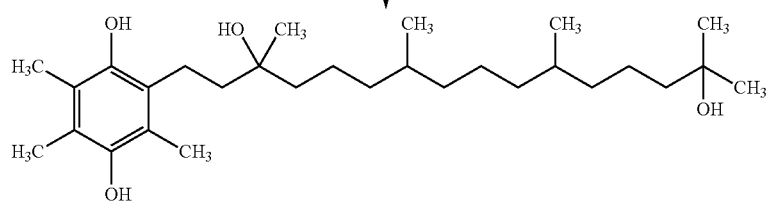

37

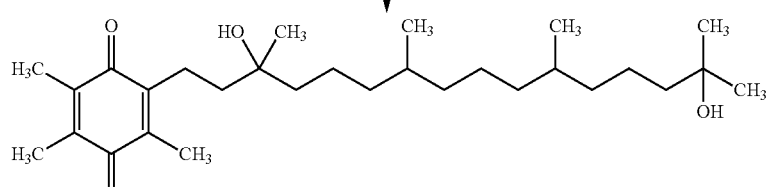

33 where alpha tocotrienol quinone 28 is selectively hydrobrominated at the terminal olefin according to the procedure described in *J. Am. Chem. Soc.* 2005, 127(42), 14911-14921. This intermediate is then cyclized to form epoxide 34 by treatment with potassium carbonate. Epoxide 34 is selectively opened using $CdCl_2$/Mg to give tertiary alcohol 35 according to the procedure in *Tet. Lett.* 1993, 34(10), 1681-1684, which is re-oxidized by exposure to atmospheric oxygen in the presence of catalytic $SiO_2$ to give quinone 36. The remaining olefins are reduced using hydrogen and catalytic palladium on carbon to give 37, which is re-oxidized to quinone 33 by exposure to atmospheric oxygen in the presence of catalytic $SiO_2$.

Another method of making compounds of formula II is by adapting the following synthesis of compound 38 of the form:

(38)

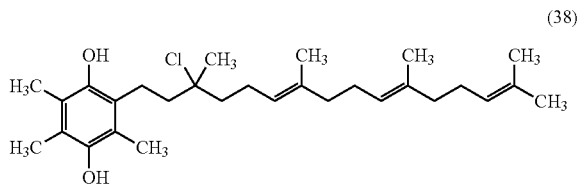 [SMILES: CC(C)=CCC/C(C)=C/CC/C(C)=C/CCC(C)(Cl)CCc1c(C)c(O)c(C)c(C)c1O]

which is as follows:

where alpha tocotrienol quinone 28 is protected as its dimethylhydroquinone 39 followed by conversion to tertiary chloride 40 by treatment with dimethylchlorosliane, benzil and catalytic indium chloride as described in *Org. Syn.* 2006, 83, 38-44. The methyl groups are then removed by treatment with boron tribromide to give dihydroquinone 38, which can be oxidized to its corresponding quinone 41 by treatment with CAN.

This method for synthesis of a compound of formula II can be adapted to the following synthesis of compound 42 of the form:

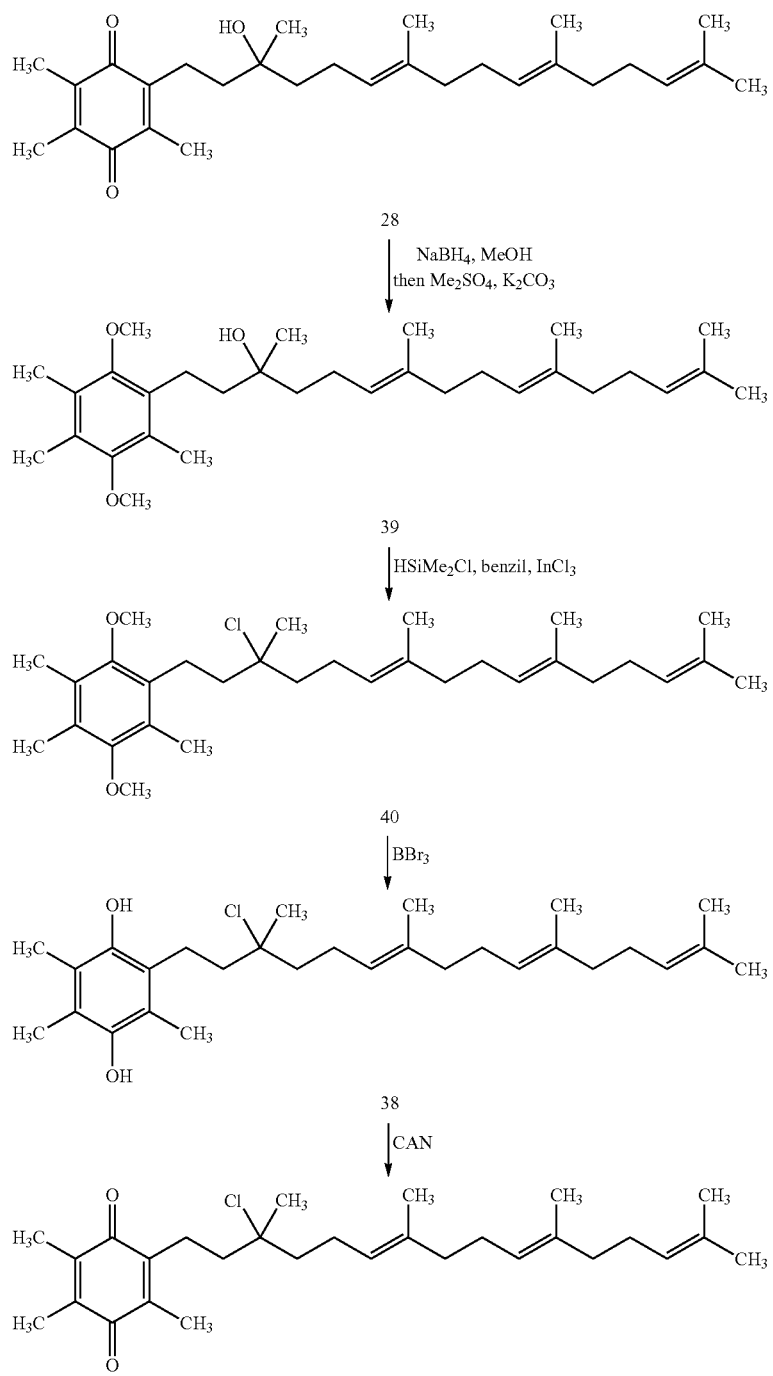

which is as follows:

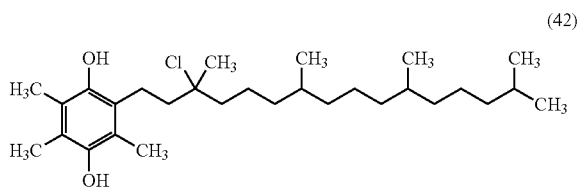 [SMILES: Cc1c(C)c(O)c(CCC(C)(Cl)CCCC(C)CCCC(C)CCCC(C)C)c(C)c1O]

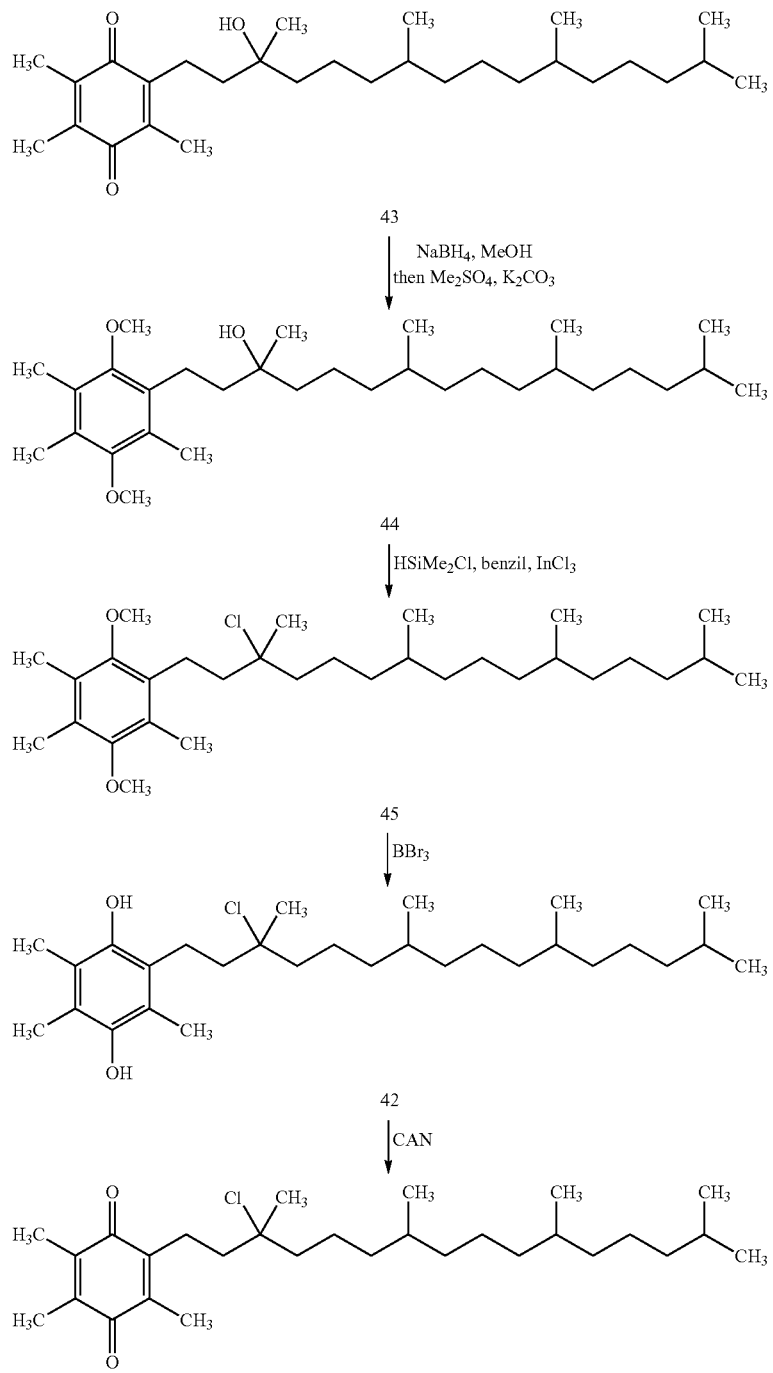

where alpha tocopherol quinone 43 is protected as its dimethylhydroquinone 44 followed by conversion to tertiary chloride 45 by treatment with dimethylchlorosliane, benzil and catalytic indium chloride as described in *Org. Syn.* 2006, 83, 38-44. The methyl groups are then removed by treatment with boron tribromide to give dihydroquinone 42, which can be oxidized to its corresponding quinone 46 by treatment with CAN.

Interconvertibility of Quinone, Dihydroquinone Forms

The quinone and dihydroquinone forms of the compounds disclosed herein are readily interconverted with appropriate reagents. For example, the quinone form of a compound can be reduced to the dihydroquinone form with reducing agents such as sodium dithionite. The hydroquinone form can be oxidized to the quinone form with oxidizing agents such as ceric ammonium nitrate (CAN) or ferric chloride. The quinone and hydroquinone forms are also readily converted electrochemically, as is well known in the art. See, e.g., Section 33.4 of Streitweiser & Heathcock, Introduction to Organic Chemistry, New York: Macmillan, 1976.

When the compounds of the invention are drawn as the quinone or hydroquinone form, that specific form is intended. However, when the quinone form is drawn and followed by the phrase "reduced counterpart thereof" or "reduced form" or the like, the structure and the subsequent phrase are intended to embrace both the quinone and hydroquinone. Similarly, when the hydroquinone form is drawn and followed by the phrase "oxidized counterpart thereof" or "oxidized form thereof" or the like, the structure and the subsequent phrase are intended to embrace both the hydroquinone and quinone.

Diseases Amenable to Treatment or Suppression with Compounds and Methods of the Invention A variety of diseases are believed to be caused or aggravated by mitochondrial disorders and impaired energy processing, and can be treated or suppressed using the compounds and methods of the invention. Such diseases include, but are not limited to, inherited mitochondrial diseases, such as Myoclonic Epilepsy with Ragged Red Fibers (MERRF), Mitochondrial Myopathy, Encephalopathy, Lactacidosis, Stroke (MELAS), Leber's Hereditary Optic Neuropathy (LHON, also referred to as Leber's Disease, Leber's Optic Atrophy (LOA), or Leber's Optic Neuropathy (LON)), Leigh Disease or Leigh Syndrome, Kearns-Sayre Syndrome (KSS), Friedreich's Ataxia (FA), other myopathies (including cardiomyopathy and encephalomyopathy), and renal tubular acidosis; neurodegenerative diseases, such as Parkinson's disease, Alzheimer's disease, amyotrophic lateral sclerosis (ALS, also known as Lou Gehrig's disease), motor neuron diseases; other neurological diseases such as epilepsy; genetic diseases such as Huntington's Disease (which is also a neurological disease); mood disorders such as schizophrenia and bipolar disorder; and certain age-associated diseases, particularly diseases for which CoQ10 has been proposed for treatment, such as macular degeneration, diabetes, and cancer.

In Vitro Assessment of Efficacy of Compounds

The compounds of the invention can be tested in vitro for efficacy. One such assay is ability of a compound to rescue FRDA fibroblasts stressed by addition of L-buthionine-(S, R)-sulfoximine (BSO), as described in Jauslin et al., Hum. Mol. Genet. 11(24):3055 (2002), Jauslin et al., FASEB J. 17:1972-4 (2003), and International Patent Application WO 2004/003565. Human dermal fibroblasts from Friedreich's Ataxia patients have been shown to be hypersensitive to inhibition of the de novo synthesis of glutathione (GSH) with L-buthionine-(S,R)-sulfoximine (BSO), a specific inhibitor of GSH synthetase (Jauslin et al., Hum. Mol. Genet. 11(24):3055 (2002)). This specific BSO-mediated cell death can be prevented by administration of antioxidants or molecules involved in the antioxidant pathway, such as a-tocopherol, short chain quinones, selenium, or small molecule glutathione peroxidase mimetics. However, antioxidants differ in their potency, i.e. the concentration at which they are able to rescue BSO-stressed FRDA fibroblasts. With this assay, $EC_{50}$ concentrations of the compounds of the invention can be determined and compared to known reference antioxidants.

Clinical Assessment of Mitochondrial Dysfunction and Efficacy of Therapy

Several readily measurable clinical markers are used to assess the metabolic state of patients with mitochondrial disorders. These markers can also be used as indicators of the efficacy of a given therapy, as the level of a marker is moved from the pathological value to the healthy value. These clinical markers include, but are not limited to, one or more of the previously discussed energy biomarkers, such as lactic acid (lactate) levels, either in whole blood, plasma, cerebrospinal fluid, or cerebral ventricular fluid; pyruvic acid (pyruvate) levels, either in whole blood, plasma, cerebrospinal fluid, or cerebral ventricular fluid; lactate/pyruvate ratios, either in whole blood, plasma, cerebrospinal fluid, or cerebral ventricular fluid; phosphocreatine levels, NADH ($NADH+H^+$) or NADPH ($NADPH+H^+$) levels; NAD or NADP levels; ATP levels; anaerobic threshold; reduced coenzyme Q ($CoQ^{red}$) levels; oxidized coenzyme Q ($CoQ^{ox}$) levels; total coenzyme Q ($CoQ^{tot}$) levels; oxidized cytochrome C levels; reduced cytochrome C levels; oxidized cytochrome C/reduced cytochrome C ratio; acetoacetate levels, β-hydroxy butyrate levels, acetoacetate/β-hydroxy butyrate ratio, 8-hydroxy-2'-deoxyguanosine (8-OHdG) levels; levels of reactive oxygen species; and levels of oxygen consumption (VO2), levels of carbon dioxide output (VCO2), and respiratory quotient (VCO2/VO2). Several of these clinical markers are measured routinely in exercise physiology laboratories, and provide convenient assessments of the metabolic state of a subject. In one embodiment of the invention, the level of one or more energy biomarkers in a patient suffering from a mitochondrial disease, such as Friedreich's ataxia, Leber's hereditary optic neuropathy, MELAS, or KSS, is improved to within two standard deviations of the average level in a healthy subject. In another embodiment of the invention, the level of one or more of these energy biomarkers in a patient suffering from a mitochondrial disease, such as Friedreich's ataxia, Leber's hereditary optic neuropathy, MELAS, or KSS is improved to within one standard deviation of the average level in a healthy subject. Exercise intolerance can also be used as an indicator of the efficacy of a given therapy, where an improvement in exercise tolerance (i.e., a decrease in exercise intolerance) indicates efficacy of a given therapy.

Several metabolic biomarkers have already been used to evaluate efficacy of CoQ10, and these metabolic biomarkers can be monitored as energy biomarkers for use in the methods of the current invention. Pyruvate, a product of the anaerobic metabolism of glucose, is removed by reduction to lactic acid in an anaerobic setting or by oxidative metabolism, which is dependent on a functional mitochondrial respiratory chain. Dysfunction of the respiratory chain may lead to inadequate removal of lactate and pyruvate from the circulation and elevated lactate/pyruvate ratios are observed in mitochondrial cytopathies (see Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)). Blood lactate/pyruvate ratio (Chariot et al., Arch. Pathol. Lab. Med. 118(7):695-7 (1994)) is, therefore, widely used as a noninvasive test for detection of mitochondrial cytopathies (see again Scriver C R, The metabolic and molecular bases of inherited disease, 7th ed., New York: McGraw-Hill, Health Professions Division, 1995; and Munnich et al., J. Inherit. Metab. Dis. 15(4):448-55 (1992)) and toxic mitochondrial myopathies (Chariot et al., Arthritis Rheum. 37(4): 583-6 (1994)). Changes in the redox state of liver mitochondria can be investigated by measuring the arterial ketone body ratio (acetoacetate/3-hydroxybutyrate:AKBR) (Ueda et al., J. Cardiol. 29(2):95-102 (1997)). Urinary excretion of 8-hydroxy-2'-deoxyguanosine (8-OHdG) often has been used as a biomarker to assess the extent of repair of ROS-induced DNA damage in both clinical and occupational settings (Erhola et al., FEBS Lett. 409(2):287-91 (1997); Honda et al., Leuk. Res. 24(6):461-8 (2000); Pilger et al., Free Radic. Res. 35(3):273-80 (2001); Kim et al. Environ Health Perspect 112(6):666-71 (2004)).

Magnetic resonance spectroscopy (MRS) has been useful in the diagnoses of mitochondrial cytopathy by demonstrating elevations in cerebrospinal fluid (CSF) and cortical white matter lactate using proton MRS (1H-MRS) (Kaufmann et al., Neurology 62(8):1297-302 (2004)). Phosphorous MRS (31P-MRS) has been used to demonstrate low levels of cortical phosphocreatine (PCr) (Matthews et al., Ann. Neurol. 29(4):435-8 (1991)), and a delay in PCr recovery kinetics following exercise in skeletal muscle (Matthews et al., Ann. Neurol. 29(4):435-8 (1991); Barbiroli et al., J. Neurol. 242(7):472-7 (1995); Fabrizi et al., J. Neurol. Sci. 137(1):20-7 (1996)). A low skeletal muscle PCr has also been confirmed in patients with mitochondrial cytopathy by direct biochemical measurements.

Exercise testing is particularly helpful as an evaluation and screening tool in mitochondrial myopathies. One of the hallmark characteristics of mitochondrial myopathies is a reduction in maximal whole body oxygen consumption (VO2max) (Taivassalo et al., Brain 126(Pt 2):413-23 (2003)). Given that VO2max is determined by cardiac output (Qc) and peripheral oxygen extraction (arterial-venous total oxygen content) difference, some mitochondrial cytopathies affect cardiac function where delivery can be altered; however, most mitochondrial myopathies show a characteristic deficit in peripheral oxygen extraction (A-V O2 difference) and an enhanced oxygen delivery (hyperkinetic circulation) (Taivassalo et al., Brain 126(Pt 2):413-23 (2003)). This can be demonstrated by a lack of exercise induced deoxygenation of venous blood with direct AV balance measurements (Taivassalo et al., Ann. Neurol. 51(1):38-44 (2002)) and non-invasively by near infrared spectroscopy (Lynch et al., Muscle Nerve 25(5):664-73 (2002); van Beekvelt et al., Ann. Neurol. 46(4):667-70 (1999)).

Several of these energy biomarkers are discussed in more detail as follows. It should be emphasized that, while certain energy biomarkers are discussed and enumerated herein, the invention is not limited to modulation, normalization or enhancement of only these enumerated energy biomarkers.

Lactic Acid (Lactate) Levels:

Mitochondrial dysfunction typically results in abnormal levels of lactic acid, as pyruvate levels increase and pyruvate is converted to lactate to maintain capacity for glycolysis. Mitochondrial dysfunction can also result in abnormal levels of $NADH+H^+$, $NADPH+H^+$, NAD, or NADP, as the reduced nicotinamide adenine dinucleotides are not efficiently processed by the respiratory chain. Lactate levels can be measured by taking samples of appropriate bodily fluids such as whole blood, plasma, or cerebrospinal fluid. Using magnetic resonance, lactate levels can be measured in virtually any volume of the body desired, such as the brain.

Measurement of cerebral lactic acidosis using magnetic resonance in MELAS patients is described in Kaufmann et al., Neurology 62(8):1297 (2004). Values of the levels of lactic acid in the lateral ventricles of the brain are presented for two mutations resulting in MELAS, A3243G and A8344G. Whole blood, plasma, and cerebrospinal fluid lactate levels can be measured by commercially available equipment such as the YSI 2300 STAT Plus Glucose & Lactate Analyzer (YSI Life Sciences, Ohio).

NAD, NADP, NADH and NADPH Levels:

Measurement of NAD, NADP, NADH ($NADH+H^+$) or NADPH ($NADPH+H^+$) can be measured by a variety of fluorescent, enzymatic, or electrochemical techniques, e.g., the electrochemical assay described in US 2005/0067303.

Oxygen Consumption ($vO_2$ or VO2), Carbon Dioxide Output ($vCO_2$ or VCO2), and Respiratory Quotient (VCO2/VO2):

$vO_2$ is usually measured either while resting (resting $vO_2$) or at maximal exercise intensity ($vO_2$ max). Optimally, both values will be measured. However, for severely disabled patients, measurement of $vO_2$ max may be impractical. Measurement of both forms of $vO_2$ is readily accomplished using standard equipment from a variety of vendors, e.g. Korr Medical Technologies, Inc. (Salt Lake City, Utah). VCO2 can also be readily measured, and the ratio of VCO2 to VO2 under the same conditions (VCO2/VO2, either resting or at maximal exercise intensity) provides the respiratory quotient (RQ).

Oxidized Cytochrome C, Reduced Cytochrome C, and Ratio of Oxidized Cytochrome C to Reduced Cytochrome C:

Cytochrome C parameters, such as oxidized cytochrome C levels (Cyt $C_{ox}$), reduced cytochrome C levels (Cyt $C_{red}$), and the ratio of oxidized cytochrome C/reduced cytochrome C ratio (Cyt $C_{ox}$)/(Cyt $C_{red}$), can be measured by in vivo near infrared spectroscopy. See, e.g., Rolfe, P., "In vivo near-infrared spectroscopy," Annu. Rev. Biomed. Eng. 2:715-54 (2000) and Strongman et al., "Non-invasive neuroimaging using near-infrared light" Biol. Psychiatry 52:679-93 (2002).

Exercise Tolerance/Exercise Intolerance:

Exercise intolerance is defined as "the reduced ability to perform activities that involve dynamic movement of large skeletal muscles because of symptoms of dyspnea or fatigue" (Piña et al., Circulation 107:1210 (2003)). Exercise intolerance is often accompanied by myoglobinuria, due to breakdown of muscle tissue and subsequent excretion of muscle myoglobin in the urine. Various measures of exercise intolerance can be used, such as time spent walking or running on a treadmill before exhaustion, time spent on an exercise bicycle (stationary bicycle) before exhaustion, and the like. Treatment with the compounds or methods of the invention can result in about a 10% or greater improvement in exercise tolerance (for example, about a 10% or greater increase in time to exhaustion, e.g. from 10 minutes to 11 minutes), about a 20% or greater improvement in exercise tolerance, about a 30% or greater improvement in exercise tolerance, about a 40% or greater improvement in exercise tolerance, about a 50% or greater improvement in exercise tolerance, about a 75% or greater improvement in exercise tolerance, or about a 100% or greater improvement in exercise tolerance. While exercise tolerance is not, strictly speaking, an energy biomarker, for the purposes of the invention, modulation, normalization, or enhancement of energy biomarkers includes modulation, normalization, or enhancement of exercise tolerance.

Similarly, tests for normal and abnormal values of pyruvic acid (pyruvate) levels, lactate/pyruvate ratio, ATP levels, anaerobic threshold, reduced coenzyme Q ($CoQ^{red}$) levels, oxidized coenzyme Q ($CoQ^{ox}$) levels, total coenzyme Q ($CoQ^{tot}$) levels, oxidized cytochrome C levels, reduced cytochrome C levels, oxidized cytochrome C/reduced cytochrome C ratio, acetoacetate levels, β-hydroxy butyrate levels, acetoacetate/β-hydroxy butyrate ratio, 8-hydroxy-2'- deoxyguanosine (8-OHdG) levels, and levels of reactive oxygen species are known in the art and can be used to evaluate efficacy of the compounds and methods of the invention. (For the purposes of the invention, modulation, normalization, or enhancement of energy biomarkers includes modulation, normalization, or enhancement of anaerobic threshold.)

Table 1, following, illustrates the effect that various dysfunctions can have on biochemistry and energy biomarkers. It also indicates the physical effect (such as a disease symptom or other effect of the dysfunction) typically associated with a given dysfunction. It should be noted that any of the energy biomarkers listed in the table, in addition to energy biomarkers enumerated elsewhere, can also be modulated, enhanced, or normalized by the compounds and methods of the invention. RQ=respiratory quotient; BMR=basal metabolic rate; HR (CO)=heart rate (cardiac output); T=body temperature (preferably measured as core temperature); AT=anaerobic threshold; pH=blood pH (venous and/or arterial).

suppressive therapy. Additionally, other energy biomarkers are known to those skilled in the art and can be monitored to evaluate the efficacy of treatment or suppressive therapy.

Use of Compounds for Modulation of Energy Biomarkers

In addition to monitoring energy biomarkers to assess the status of treatment or suppression of mitochondrial diseases, the compounds of the invention can be used in subjects or patients to modulate one or more energy biomarkers. Modulation of energy biomarkers can be done to normalize energy biomarkers in a subject, or to enhance energy biomarkers in a subject.

Normalization of one or more energy biomarkers is defined as either restoring the level of one or more such energy biomarkers to normal or near-normal levels in a subject whose levels of one or more energy biomarkers show pathological differences from normal levels (i.e., levels in a healthy subject), or to change the levels of one or more energy biomarkers to alleviate pathological symptoms in a subject. Depending on the nature of the energy biomarker, such levels may show measured values either above or

TABLE 1

| Site of Dysfunction | Biochemical Event | Measurable Energy Biomarker | Physical Effect |
| --- | --- | --- | --- |
| Respiratory Chain | ↑ NADH | Δ lactate, Δ lactate: pyruvate ratio; and Δ acetoacetate: β-hydroxy butyrate ratio | Metabolic dyscrasia & fatigue |
| Respiratory Chain | ↓ $H^+$ gradient | Δ ATP | Organ dependent dysfunction |
| Respiratory Chain | ↓ Electron flux | Δ $VO_2$, RQ, BMR, ΔT, AT, pH | Metabolic dyscrasia & fatigue |
| Mitochondria & cytosol | ↓ ATP, ↓ $VO_2$ | Δ Work, ΔHR (CO) | Exercise intolerance |
| Mitochondria & cytosol | ↓ ATP | Δ PCr | Exercise intolerance |
| Respiratory Chain | ↓ Cyt $C_{Ox/Red}$ | Δ λ ~700-900 nM (Near Infrared Spectroscopy) | Exercise intolerance |
| Intermediary metabolism | ↓ Catabolism | Δ $C^{14}$-Labeled substrates | Metabolic dyscrasia & fatigue |
| Respiratory Chain | ↓ Electron flux | Δ Mixed Venous $VO_2$ | Metabolic dyscrasia & fatigue |
| Mitochondria & cytosol | ↑ Oxidative stress | Δ Tocopherol & Tocotrienols, CoQ10, docosahexanoic acid | Uncertain |
| Mitochondria & cytosol | ↑ Oxidative stress | Δ $Glutathione_{red}$ | Uncertain |
| Mitochondria & cytosol | Nucleic acid oxidation | Δ8-hydroxy 2-deoxy guanosine | Uncertain |
| Mitochondria & cytosol | Lipid oxidation | ΔIsoprostane(s), eicasanoids | Uncertain |
| Cell membranes | Lipid oxidation | ΔEthane (breath) | Uncertain |
| Cell membranes | Lipid oxidation | ΔMalondialdehyde | Uncertain |

Treatment of a subject afflicted by a mitochondrial disease in accordance with the methods of the invention may result in the inducement of a reduction or alleviation of symptoms in the subject, e.g., to halt the further progression of the disorder.

Partial or complete suppression of the mitochondrial disease can result in a lessening of the severity of one or more of the symptoms that the subject would otherwise experience. For example, partial suppression of MELAS could result in reduction in the number of stroke-like or seizure episodes suffered.

Any one, or any combination of, the energy biomarkers described herein provide conveniently measurable benchmarks by which to gauge the effectiveness of treatment or below a normal value. For example, a pathological lactate level is typically higher than the lactate level in a normal (i.e., healthy) person, and a decrease in the level may be desirable. A pathological ATP level is typically lower than the ATP level in a normal (i.e., healthy) person, and an increase in the level of ATP may be desirable. Accordingly, normalization of energy biomarkers can involve restoring the level of energy biomarkers to within about at least two standard deviations of normal in a subject, more preferably to within about at least one standard deviation of normal in a subject, to within about at least one-half standard deviation of normal, or to within about at least one-quarter standard deviation of normal.

When an increase in an energy biomarker level is desired to normalize the one or more such energy biomarker, the level of the energy biomarker can be increased to within about at least two standard deviations of normal in a subject, more preferably increased to within about at least one standard deviation of normal in a subject, increased to within about at least one-half standard deviation of normal, or increased to within about at least one-quarter standard deviation of normal, by administration of one or more compounds according to the invention. Alternatively, the level of one or more of the energy biomarkers can be increased by about at least 10% above the subject's level of the respective one or more energy biomarkers before administration; by about at least 20% above the subject's level of the respective one or more energy biomarkers before administration, by about at least 30% above the subject's level of the respective one or more energy biomarkers before administration, by about at least 40% above the subject's level of the respective one or more energy biomarkers before administration, by about at least 50% above the subject's level of the respective one or more energy biomarkers before administration, by about at least 75% above the subject's level of the respective one or more energy biomarkers before administration, or by about at least 100% above the subject's level of the respective one or more energy biomarkers before administration.

When a decrease in a level of one or more energy biomarkers is desired to normalize the one or more energy biomarkers, the level of the one or more energy biomarkers can be decreased to a level within about at least two standard deviations of normal in a subject, more preferably decreased to within about at least one standard deviation of normal in a subject, decreased to within about at least one-half standard deviation of normal, or decreased to within about at least one-quarter standard deviation of normal, by administration of one or more compounds according to the invention. Alternatively, the level of the one or more energy biomarkers can be decreased by about at least 10% below the subject's level of the respective one or more energy biomarkers before administration, by about at least 20% below the subject's level of the respective one or more energy biomarkers before administration, by about at least 30% below the subject's level of the respective one or more energy biomarkers before administration, by about at least 40% below the subject's level of the respective one or more energy biomarkers before administration, by about at least 50% below the subject's level of the respective one or more energy biomarkers before administration, by about at least 75% below the subject's level of the respective one or more energy biomarkers before administration, or by about at least 90% below the subject's level of the respective one or more energy biomarkers before administration.

Enhancement of the level of one or more energy biomarkers is defined as changing the extant levels of one or more energy biomarkers in a subject to a level which provides beneficial or desired effects for the subject. For example, a person undergoing strenuous effort or prolonged vigorous physical activity, such as mountain climbing, could benefit from increased ATP levels or decreased lactate levels. As described above, normalization of energy biomarkers may not achieve the optimum state for a subject with a mitochondrial disease, and such subjects can also benefit from enhancement of energy biomarkers. Examples of subjects who could benefit from enhanced levels of one or more energy biomarkers include, but are not limited to, subjects undergoing strenuous or prolonged physical activity, subjects with chronic energy problems, or subjects with chronic respiratory problems. Such subjects include, but are not limited to, pregnant females, particularly pregnant females in labor; neonates, particularly premature neonates; subjects exposed to extreme environments, such as hot environments (temperatures routinely exceeding about 85-86 degrees Fahrenheit or about 30 degrees Celsius for about 4 hours daily or more), cold environments (temperatures routinely below about 32 degrees Fahrenheit or about 0 degrees Celsius for about 4 hours daily or more), or environments with lower-than-average oxygen content, higher-than-average carbon dioxide content, or higher-than-average levels of air pollution (airline travelers, flight attendants, subjects at elevated altitudes, subjects living in cities with lower-than-average air quality, subjects working in enclosed environments where air quality is degraded); subjects with lung diseases or lower-than-average lung capacity, such as tubercular patients, lung cancer patients, emphysema patients, and cystic fibrosis patients; subjects recovering from surgery or illness; elderly subjects, including elderly subjects experiencing decreased energy; subjects suffering from chronic fatigue, including chronic fatigue syndrome; subjects undergoing acute trauma; subjects in shock; subjects requiring acute oxygen administration; subjects requiring chronic oxygen administration; or other subjects with acute, chronic, or ongoing energy demands who can benefit from enhancement of energy biomarkers.

Accordingly, when an increase in a level of one or more energy biomarkers is beneficial to a subject, enhancement of the one or more energy biomarkers can involve increasing the level of the respective energy biomarker or energy biomarkers to about at least one-quarter standard deviation above normal, about at least one-half standard deviation above normal, about at least one standard deviation above normal, or about at least two standard deviations above normal. Alternatively, the level of the one or more energy biomarkers can be increased by about at least 10% above the subject's level of the respective one or more energy biomarkers before enhancement, by about at least 20% above the subject's level of the respective one or more energy biomarkers before enhancement, by about at least 30% above the subject's level of the respective one or more energy biomarkers before enhancement, by about at least 40% above the subject's level of the respective one or more energy biomarkers before enhancement, by about at least 50% above the subject's level of the respective one or more energy biomarkers before enhancement, by about at least 75% above the subject's level of the respective one or more energy biomarkers before enhancement, or by about at least 100% above the subject's level of the respective one or more energy biomarkers before enhancement.

When a decrease in a level of one or more energy biomarkers is desired to enhance one or more energy biomarkers, the level of the one or more energy biomarkers can be decreased by an amount of about at least one-quarter standard deviation of normal in a subject, decreased by about at least one-half standard deviation of normal in a subject, decreased by about at least one standard deviation of normal in a subject, or decreased by about at least two standard deviations of normal in a subject. Alternatively, the level of the one or more energy biomarkers can be decreased by about at least 10% below the subject's level of the respective one or more energy biomarkers before enhancement, by about at least 20% below the subject's level of the respective one or more energy biomarkers before enhancement, by about at least 30% below the subject's level of the respective one or more energy biomarkers before enhancement, by about at least 40% below the subject's level of the respective one or more energy biomarkers before enhancement, by about at least 50% below the subject's level of the respective one or more energy biomarkers before enhancement, by about at least 75% below the subject's level of the respective one or more energy biomarkers before enhancement, or by about at least 90% below the subject's level of the respective one or more energy biomarkers before enhancement.

Use of Compounds in Research Applications, Experimental Systems, and Assays

The compounds of the invention can also be used in research applications, such as in in vitro, in vivo, or ex vivo experiments in order to modulate one or more energy biomarkers in an experimental system. Such experimental systems can be cell samples, tissue samples, cell components or mixtures of cell components, partial organs, whole organs, or organisms. Such research applications can include, but are not limited to, use as assay reagents, elucidation of biochemical pathways, or evaluation of the effects of other agents on the metabolic state of the experimental system in the presence/absence of one or more compounds of the invention.

Additionally, the compounds of the invention can be used in biochemical tests or assays. Such tests can include incubation of one or more compounds of the invention with a tissue or cell sample from a subject to evaluate a subject's potential response (or the response of a specific subset of subjects) to administration of said one or more compounds, or to determine which compound of the invention produces the optimum effect in a specific subject or subset of subjects. One such test or assay would involve 1) obtaining a cell sample or tissue sample from a subject or set of subjects in which modulation of one or more energy biomarkers can be assayed; 2) administering one or more compounds of the invention to the cell sample(s) or tissue sample(s); and 3) determining the amount of modulation of the one or more energy biomarkers after administration of the one or more compounds, compared to the status of the energy biomarker prior to administration of the one or more compounds. Another such test or assay would involve 1) obtaining a cell sample or tissue sample from a subject or set of subjects in which modulation of one or more energy biomarkers can be assayed; 2) administering at least two compounds of the invention to the cell sample(s) or tissue sample(s); 3) determining the amount of modulation of the one or more energy biomarkers after administration of the at least two compounds, compared to the status of the energy biomarker prior to administration of the at least two compounds, and 4) selecting a compound for use in treatment, suppression, or modulation based on the amount of modulation determined in step 3).

Pharmaceutical Formulations

The compounds described herein can be formulated as pharmaceutical compositions by formulation with additives such as pharmaceutically acceptable excipients, pharmaceutically acceptable carriers, and pharmaceutically acceptable vehicles. Suitable pharmaceutically acceptable excipients, carriers and vehicles include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

A pharmaceutical composition can comprise a unit dose formulation, where the unit dose is a dose sufficient to have a therapeutic or suppressive effect or an amount effective to modulate, normalize, or enhance an energy biomarker. The unit dose may be sufficient as a single dose to have a therapeutic or suppressive effect or an amount effective to modulate, normalize, or enhance an energy biomarker. Alternatively, the unit dose may be a dose administered periodically in a course of treatment or suppression of a disorder, or to modulate, normalize, or enhance an energy biomarker.

Pharmaceutical compositions containing the compounds of the invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Time-release or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation (e.g. as mists or sprays), rectally, or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The compounds are mixed with pharmaceutically acceptable carriers, adjuvants, and vehicles appropriate for the desired route of administration. Oral administration is a preferred route of administration, and formulations suitable for oral administration are preferred formulations. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The compounds can also be administered as prodrugs, where the prodrug undergoes transformation in the treated subject to a form which is therapeutically effective. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at room temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq (1976).

The invention also provides articles of manufacture and kits containing materials useful for treating or suppressing mitochondrial diseases. The article of manufacture comprises a container with a label. Suitable containers include, for example, bottles, vials, and test tubes. The containers may be formed from a variety of materials such as glass or plastic. The container holds a composition having an active agent which is effective for treating or suppressing mitochondrial diseases. The active agent in the composition is one or more of the compounds of the invention. The label on the container indicates that the composition is used for treating or suppressing mitochondrial diseases, and may also indicate directions for either in vivo or in vitro use, such as those described above.

The invention also provides kits comprising any one or more of the compounds of the invention. In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein.

In other aspects, the kits may be used for any of the methods described herein, including, for example, to treat an individual with a mitochondrial disorder, or to suppress a mitochondrial disorder in an individual.

The amount of active ingredient that may be combined with the carrier materials to produce a single dosage form will vary depending upon the host to which the active ingredient is administered and the particular mode of administration. It will be understood, however, that the specific dose level for any particular patient will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount or effective amount for a given situation can be readily determined by routine experimentation and is within the skill and judgment of the ordinary clinician.

Examples of dosages which can be used are an effective amount within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight. Compounds of the present invention may be administered in a single daily dose, or the total daily dosage may be administered in divided dosage of two, three or four times daily.

While the compounds of the invention can be administered as the sole active pharmaceutical agent, they can also be used in combination with one or more other agents used in the treatment or suppression of disorders. Representative agents useful in combination with the compounds of the invention for the treatment or suppression of mitochondrial diseases include, but are not limited to, Coenzyme Q, vitamin E, idebenone, MitoQ, vitamins, and antioxidant compounds.

When additional active agents are used in combination with the compounds of the present invention, the additional active agents may generally be employed in therapeutic amounts as indicated in the Physicians' Desk Reference (PDR) 53rd Edition (1999), which is incorporated herein by reference, or such therapeutically useful amounts as would be known to one of ordinary skill in the art.

The compounds of the invention and the other therapeutically active agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. When administered in combination with other therapeutic agents, the therapeutic agents can be formulated as separate compositions that are given at the same time or different times, or the therapeutic agents can be given as a single composition.

The invention will be further understood by the following nonlimiting examples.

EXAMPLES

Example 1

Synthesis of Compounds 2,3-Dimethyl-5,6-bis-(3-methyl-butyl)-[1,4]benzoquinone

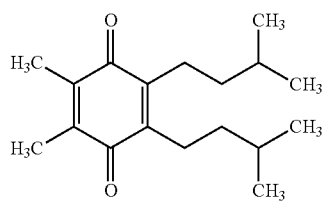 [SMILES: CC1=C(C)C(=O)C(CCC(C)C)=C(CCC(C)C)C1=O]

A solution of FeCl$_3$.6H$_2$O (81.0 g, 300 mmol) in water (100 mL) was added to a solution of 2,3-dimethyl-benzene-1,4-diol (13.8 g, 100 mmol) in MTBE (150 ml) at ambient temperature. Aqueous sodium hydroxide solution (2.5M, 60 mL, 150 mmol) was added to the vigorously stirring mixture and the reaction heated to 50° C. for 5 hrs. MTBE (150 mL) and water (150 mL) were added and the aqueous layer further extracted with MTBE (2×100 mL). The combined organics were washed with brine (100 mL), dried (Na$_2$SO$_4$), and concentrated to give the intermediate 2,3-dimethyl-[1,4]benzoquinone as an orange-yellow solid (12.0 g, 88%), which was used in the next step without further purification.

A solution of silver(I) nitrate (3.40 g, 20 mmol) in water (50 mL) was added to a mixture of 2,3-dimethyl-[1,4]benzoquinone (1.36 g, 10 mmol) and 4-methylpentanoic acid (1.26 mL, 1.16 g, 20 mmol) in acetonitrile (50 mL) at ambient temperature. The mixture was stirred vigorously, heated to 75-80° C., and a solution of ammonium persulfate (4.56 g, 20 mmol) in water (30 mL) added dropwise via syringe-pump over 4 hrs. After a total 20 hrs the majority of the acetonitrile was removed using a rotoevaporator, the residue partitioned between MTBE (100 mL) and water (100 mL), and the aqueous layer further extracted with MTBE (50 mL). The combined organics were washed with 1:1 saturated brine-water (50 mL) and then concentrated. The orange-red residue was purified by column chomratography on silica-gel using a gradient elution of 1 to 2.5% EtOAc-hexanes to give the 2,3-Dimethyl-5,6-bis-(3-methyl-butyl)-[1,4]benzoquinone as a yellow oil (200 mg, 7%). $^1$H-NMR (CDCl$_3$, 400 MHz, δ ppm): 2.42-2.38 (4H, m), 1.99 (6H, s), 1.62 (2H, nonet, J=7 Hz), 1.28-1.22 (4H, m), 0.93 (12H, d, J=7 Hz). $^{13}$C-NMR (CDCl$_3$, 100 MHz, δ ppm): 187.60, 144.35, 140.39, 38.66, 28.71, 24.55, 22.35, 12.28.

2-(3-Hydroxy-3-methyl-butyl)-5,6-dimethyl-3-(3-methyl-but-2-enyl)-[1,4]benzoquinone

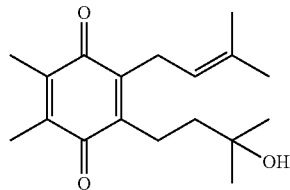 [SMILES: CC(C)=CCC1=C(CCC(C)(C)O)C(=O)C(C)=C(C)C1=O]

To a stirring solution of 113 mg 2,2,7,8-tetramethyl-5-(3-methyl-but-2-enyl)-chroman-6-ol (prepared in the method of Walkinshaw, et al., US 2005/0065099 A1, Mar. 24, 2005) in 3.75 mL acetonitrile-water (5:1) at 5° C. was added a yellow solution of cerium(IV) ammonium nitrate (475 mg) in acetonitrile-water (1:4, 2.75 mL) over a period of 5 minutes. The reaction mixture was allowed to stir for an additional 5 minutes, after which it was poured into a separatory funnel containing dichloromethane (30 mL) and water (30 mL). The aqueous layer was removed and the remaining organics were washed once with 1.0 M sodium chloride solution (30 mL). The organics were subsequently dried over anhydrous sodium sulfate, filtered, and concentrated in vacuo. Silica gel chromatography (15% ethyl acetate-85% hexanes) provided 58 mg of 2-(3-hydroxy-3-methyl-butyl)-5,6-dimethyl-3-(3-methyl-but-2-enyl)-[1,4]-benzoquinone. $^1$H NMR (CDCl$_3$, 400 MHz) 4.92 (t, 1H), 3.18 (d, 2H), 2.54 (t, 2H), 1.99 (s, 6H), 1.74 (s, 3H), 1.66 (s, 3H), 1.52 (m, 2H), 1.26 (s, 6H).

2-(3-Hydroxy-3-methyl-butyl)-5,6-dimethyl-3-(3-methyl-butyl)-[1,4]benzoquinone

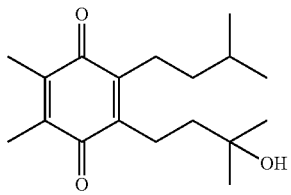 [SMILES: CC1=C(C)C(=O)C(CCC(C)(C)O)=C(CCC(C)C)C1=O]

To a solution of 2,2,7,8-tetramethyl-5-(3-methyl-but-2-enyl)-chroman-6-ol (68 mg) in ethyl acetate (2.4 mL) was added Pd/C (26 mg, 5% w/w). The resulting suspension was flushed with hydrogen gas, the container sealed, and the contents stirred under 1 atm of hydrogen gas for 30 min. The mixture was then filtered and concentrated in vacuo. The resulting residue was dissolved in acetonitrile-water (5:1, 2.6 mL) and the solution cooled to 5° C. in an ice-water bath. Into the reaction mixture was added a solution of cerium(IV) ammonium nitrate (287 mg) in acetonitrile-water (1:4, 1.6 mL) over a period of 5 minutes. The reaction mixture was allowed to stir for an additional 5 minutes, after which it was poured into a separatory funnel containing dichloromethane (30 mL) and water (30 mL). The aqueous layer was removed and the remaining organics were washed once with 1.0 M sodium chloride solution (30 mL). The organics were subsequently dried over anhydrous sodium sulfate, filtered, and concentrated in vacuo. Silica gel chromatography (18% ethyl acetate-82% hexanes) provided 29 mg of 2-(3-hydroxy-3-methyl-butyl)-5,6-dimethyl-3-(3-methyl-butyl)-[1,4]benzoquinone. $^1$H NMR (CDCl$_3$, 400 MHz) 2.53 (m, 2H), 2.43 (m, 2H), 1.99 (s, 3H), 1.62 (m, 1H), 1.53 (m, 2H), 1.24 (m, 8H), 0.94 (s, 3H), 0.92 (s, 3H).

(E)-1-(7-chloro-3-methylhept-2-enyl)-2,5-dimethoxy-3,4,6-trimethylbenzene

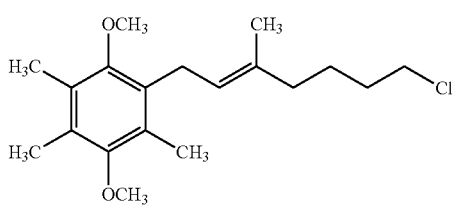 [SMILES: COc1c(C)c(C)c(OC)c(C/C=C(\C)CCCCCl)c1C]

Zirconocene dichloride (1.66 g, 5.6 mmol) was treated with dichloroethane (22 mL) and trimethylaluminum solution (23 mmol, 2.0 M in heptane) was added. The clear yellow solution was stirred for 0.75 h and cooled to 0° C. 5-chloro-1-pentyne was added neat over 1 h at 0° C. and stirred 10 h at room temperature. The clear brown solution was concentrated in vacuo and triturated with anhydrous hexanes (3×5 mL), the solvent being removed after each iteration via vacuum. Hexanes (10 mL) was then added and the solution cannulated away from the solids. The solids were rinsed with hexanes (5 mL) and the combined hexane solutions diluted with THF (80 mL). A prepared solution of 1-(chloromethyl)-2,5-dimethoxy-3,4,6-trimethylbenzene (4.009 g, 17.5 mmol) in THF (10 mL) was added to the vinyl alane via cannula and the combined solution cooled to 10° C. The catalyst was prepared by treating bis-(triphenylphosphine)nickel dichloride (579 mg, 0.87 mmol) in THF (5 mL) with n-BuLi (1.6 M in hexanes, 1.75 mmol). The blood-red clear catalyst solution was then added via cannula to the 10° C. vinyl alane solution and let warm to room temperature over 7 h. The reaction was cooled to 0° C. and quenched by slow addition of 2.5 M HCl (100 mL) over 0.5 h followed by hexanes (100 mL) and separation. The aqueous layer was extracted 2×100 mL hexanes, 1×50 mL 50% EtOAc/hexanes and the combined organics washed once with brine (100 mL) and dried over anhydrous Na$_2$SO$_4$ and concentrated to a brown oil. Multiple flash chromatography yielded 5.2 g of (E)-1-(7-chloro-3-methylhept-2-enyl)-2,5-dimethoxy-3,4,6-trimethylbenzene as a clear oil (94.6%). $^1$H NMR (400 MHz, CDCl$_3$) d 5.05 (t, J=6.4 Hz, 1H), 3.63 (S, 6H), 3.49 (t, J=6.4 Hz, 2H), 3.35 (d, J=8.4 Hz, 1H), 2.16 (s, 9H), 1.98 (t, J=7.6 Hz, 2H), 1.76 (s, 3H), 1.70 (m, 2H), 1.52 (m, 2H). $^{13}$C NMR (100 MHz, CDCl$_3$) d 153.0, 152.7, 134.4, 131.4, 128.3, 127.9, 127.6, 123.8, 60.9, 60.1, 45.0, 38.8, 32.2, 26.1, 25.1, 16.1, 12.8, 12.7, 12.2.

(E)-2-(7-chloro-3-methylhept-2-enyl)-3,5,6-trimethylcyclohexa-2,5-diene-1,4-dione

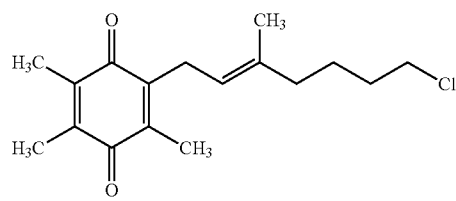 [SMILES: CC1=C(C)C(=O)C(C/C=C(\C)CCCCCl)=C(C)C1=O]

CAN (709 mg, 1.29 mmol) was dissolved into AcCN (7 mL) and water (3 mL) then cooled to 0° C. In a separate flask, (E)-1-(7-Chloro-3-methylhept-2-enyl)-2,5-dimethoxy-3,4,6-trimethylbenzene (175 mg, 0.53 mmol) was dissolved into AcCN (2 mL) and 1 drop of H$_2$O and transferred to the stirring CAN solution. Stirring was maintained for 1 h, after which time an additional charge of CAN (350 mg) was added and let stir for 1 h. Water (10 mL) and EtOAc (10 mL) were added, the layers separated and the combined organics washed H$_2$O (2×5 mL). The combined aqueous phases were back extracted using EtOAc (2×5 mL) and the combined organics washed with brine (2×5 mL), dried over anhydrous Na$_2$SO$_4$ and concentrated to a yellow oil. Flash chromatography (SiO$_2$) yielded 29.7 mg of (E)-2-(7-chloro-3-methylhept-2-enyl)-3,5,6-trimethylcyclohexa-2,5-diene-1,4-dione as a yellow oil (18.7%). $^1$H NMR (400 MHz, CDCl$_3$) δ4.95 (t, J=6.8 Hz, 1H), 3.50 (t, J=6.8 Hz, 2H), 3.19 (d, J=6.8 Hz, 2H), 2.00 (m, 11H), 1.71 (m, 5H), 1.51 (m, J=7.2 Hz, 2H).

$^{13}$C NMR (100 MHz, δ) 187.9, 187.0, 143.0, 140.4, 140.3, 136.5, 120.0, 44.9, 38.8, 32.1, 25.6, 24.9, 16.1, 12.3, 12.2.

(E)-1-(6-chloro-3-methylhex-2-enyl)-2,5-dimethoxy-3,4,6-trimethylbenzene

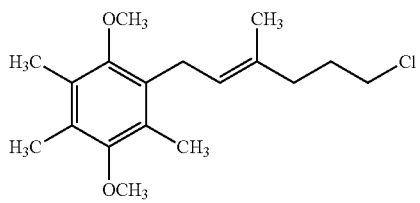

Zirconocene dichloride (982 mg, 3.36 mmol) was treated with trimethylaluminum (13.1 mL, 2.0 M in heptane) and dichloroethane (13 mL). The bright yellow solution was cooled to 0° C. and 5-chloro-1-pentyne added over 5 minutes. The reaction was held at 0° C. for 0.25 h and warmed to room temperature. After 5.5 h the dark yellow solution was reduced in vacuo to ca. 70% of its original volume and triturated with hexanes (2×10 mL). A final portion of hexanes (10 mL) was added and cannulated away from the precipitated salts with additional hexane wash (2×2 mL) to ensure complete transfer. The vinyl alane which was subsequently diluted with THF (40 mL) and treated with 1-(chloromethyl)-2,5-dimethoxy-3,4,6-trimethylbenzene (1.35 g) in THF (15 mL) via cannula. A separate flask containing bis-(triphenylphosphine)nickel dichloride (967 mg, 1.47 mmol) in THF (5 mL) was treated with n-buLi (260 mL, 1.6 M in heptane, 0.416 mmol) to give a dark red, clear solution which was added to the vinyl alane solution. The reaction was placed in a 15° C. water bath to control an exotherm and let stir overnight at room temperature. The reaction was quenched by treatment with citric acid (11 g) in $H_2O$ (50 mL) via slow addition, followed by addition of hexanes (50 mL) and $H_2O$ (50 mL) with stirring for an additional 20 minutes. The layers were separated and the aqueous phase extracted using hexanes (3×50 mL) then MTBE (2×50 mL). The combined organics were washed with brine (2×20 mL), dried over anhydrous $Na_2SO_4$ and concentrated to a brown oil. Flash chromatography yielded 2.011 g (74.0%) of (E)-1-(6-chloro-3-methylhex-2-enyl)-2,5-dimethoxy-3,4,6-trimethylbenzene as a clear oil. $^1H$ NMR (400 MHz, $CDCl_3$) d 5.11 (t, J=7.2 Hz, 1H), 3.65 (s, 6H), 3.48 (t, J=6.8 Hz, 2H), 3.76 (d, J=6.4 Hz, 2H), 2.18 (s, 9H), 2.10 (t, J=7.2 Hz, 2H) 1.84 (quintet, J=7.2 Hz, 2H), 1.78 (s, 3H). $^{13}C$ NMR (100 MHz, $CDCl_3$) d 153.0, 152.6, 133.4, 131.3, 128.4, 127.9, 127.6, 124.5, 60.9, 60.1, 44.6, 36.6, 30.8, 26.1, 16.2, 12.8, 12.7, 12.2.

1-((E)-6-iodo-3-methylhex-2-enyl)-2,5-dimethoxy-3,4,6-trimethylbenzene

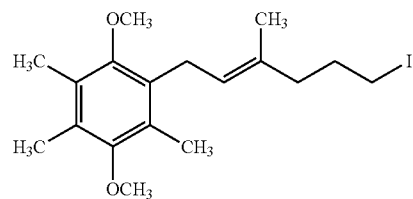 [SMILES: COc1c(C)c(C)c(OC)c(C/C=C(\C)CCCI)c1C]

(E)-1-(6-chloro-3-methylhex-2-enyl)-2,5-dimethoxy-3,4,6-trimethylbenzene (725.8 mg, 2.334 mmol) and NaI (3.09 g, 20.61 mmol) were dissolved into acetone (10 mL) and heated to reflux for 18 h. The reaction mixture was cooled to room temperature and the cloudy solution added to $H_2O$ (50 mL) and of a 50% EtOAc/hexanes solution (50 mL), the layers separated and the aqueous phase extracted with hexanes (3×25 mL), then MTBE (2×25 mL). The organics were combined and washed with saturated NaCl solution (2×25 mL) and dried over anhydrous $Na_2SO_4$. Concentration yielded 930.0 mg (99.0%) of 1-((E)-6-iodo-3-methyl-hex-2-enyl)-2,5-dimethoxy-3,4,6-trimethylbenzene as a pale yellow oil. $^1H$ NMR (400 MHz, $CDCl_3$) d 5.12 (t, J=6.4 Hz, 1H), 3.65 (s, 6H), 3.36 (d, J=6.0 Hz, 2H), 3.12 (t, J=7.2 Hz, 2H), 2.18 (S 9H), 2.07 (t, J=7.2 Hz, 2H), 1.91 (t, J=7.2 HZ, 2H), 1.77 (s, 3H). $^{13}C$ NMR (100 MHz, $CDCl_3$) d 153.1, 152.6, 133.0, 131.3, 128.4, 127.9, 127.6, 124.7, 60.9, 60.1, 40.1, 31.7, 26.1, 16.1, 12.8, 12.7, 12.2.

(E)-2,3,5-trimethyl-6-(3-methylnon-2-enyl)-1,4-benzoquinone

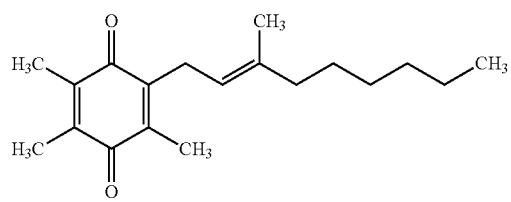 [SMILES: CCCCCC/C(C)=C/CC1=C(C)C(=O)C(C)=C(C)C1=O]

Zirconocene dichloride (220 mg, 0.755 mmol) was treated with trimethylaluminum in heptane (3 mL 2.0 M) and the solvent removed in vacuo. Dichloroethane (3 mL) was added and the yellow solution cooled to 0° C. prior to slow addition of 450 µL 1-octyne (336 mg, 3.05 mmol). The ice bath was removed after 20 minutes and the reaction warmed to rt over 2.5 h at which time it was concentrated in vacuo to a yellow slurry and triturated with hexanes (4 mL) and the solvent removed in vacuo. Hexanes (3 mL) was added and the liquid cannulated away from the white solids. The solids were washed with 2 mL hexanes and the washings combined, concentrated to a yellow oil, dissolved into THF (5 mL) and cooled to −78° C. 2-(chloromethyl)-3,5,6-trimethyl-1,4-benzoquinone (400 mg, 2.01 mmol) was dissolved into THF (3 mL) and transferred to the vinyl alane via cannula with THF (2×1 mL) to assist the transfer. bis-(Triphenylphosphine)nickel dichloride (66.2 mg, 0.101 mmol) was suspended in THF (2 mL) and treated with n-BuLi in hexanes (1.6 M, 0.20 mmol) to give a clear, blood red solution which was added via cannula to the chilled vinyl alane, chloromethyl quinone solution. The reaction was warmed to room temperature overnight and chilled to −20 C prior to addition of a 1 M citric acid solution (20 mL). The solution was stirred for 0.75 h, EtOAc (10 mL) added and the layers separated. The aqueous phase was extracted EtOAc (2×10 mL), the combined organics washed with brine (2×10 mL), dried over anhydrous $Na_2SO_4$ and concentrated to a yellow oil. Multiple flash chromatography yielded 138.7 mg (23.9%) of (E)-2,3,5-trimethyl-6-(3-methylnon-2-enyl)-1,4-benzoquinone as a yellow oil. $^1H$ NMR (400 MHz, $CDCl_3$) δ4.91 (t, J=6.8 Hz, 1H), 3.18 (d, J=6.8 Hz, 2H), 2.00 (s, 9H), 1.92 (t, J=8.0 Hz, 2H), 1.70 (s, 3H), 1.34-1.21 (m, 8H), 0.84 (t, J=6.8 Hz, 3H). $^{13}C$ NMR (100 MHz, $CDCl_3$) δ 187.8, 187.0, 143.2, 140.2, 137.4, 119.1, 39.6, 31.6, 28.8, 27.7, 25.5, 22.6, 16.1, 14.0, 12.3, 12.1

(E)-7-(2,5-dimethoxy-3,4,6-trimethylphenyl)-5-methylhept-5-enenitrile

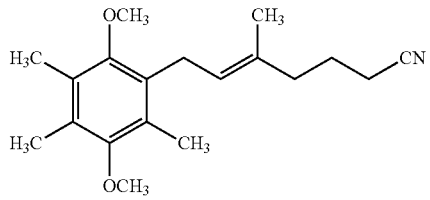

1-((E)-6-iodo-3-methylhex-2-enyl)-2,5-dimethoxy-3,4,6-trimethylbenzene (412 mg, 1.024 mmol) was combined with NaCN (247.7 mg) and dissolved in DMF (2 mL). The reaction was stirred for 25 h at 45° C. then cooled to room temperature. To the mixture was added H$_2$O (10 mL) followed by MTBE (6 mL) and the layers separated. The aqueous phase was extracted into MTBE (4×6 mL) and the combined organics washed with H$_2$O (2×5 mL) followed by saturated NaCl solution (2×5 mL) and dried over Na$_2$SO$_4$. The organics were concentrated to give (E)-7-(2,5-dimethoxy-3,4,6-trimethylphenyl)-5-methylhept-5-enenitrile as a pale yellow oil, 306.4 mg (99.0%). $^1$H NMR (400 MHz, CDCl$_3$) d 5.14 (t, J=6.4 Hz, 1H), 3.65 (s, 6H), 3.37 (d, J=6.8 Hz, 2H), 2.26 (t, J=7.2 Hz, 2H), 2.18 (s, 9H), 2.12 (t, J=7.2 Hz, 2H), 1.76 (m, 4H). $^{13}$C NMR (100 MHz, CDCl$_3$) d 153.1, 152.6, 132.5, 131.0, 128.5, 128.0, 125.4, 119.7, 60.8, 60.1, 38.2, 38.2, 26.1, 23.5, 16.4, 15.9, 12.8, 12.7, 12.2.

N-((E)-7-(2,5-dimethoxy-3,4,6-trimethylphenyl)-5-methylhept-5-enyl)acetamide

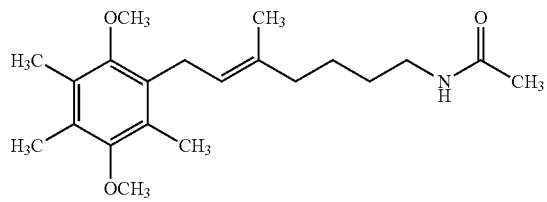 [SMILES: COc1c(C)c(C)c(OC)c(C/C=C(\C)CCCCNC(C)=O)c1C]

LAH (102 mg, 2.69 mmol) in THF (5 mL) was treated with (E)-7-(2,5-dimethoxy-3,4,6-trimethylphenyl)-5-methylhept-5-enenitrile (150.9 mg, 0.5006 mmol) in THF (5 mL) by dropping funnel over 10 minutes. After 4.25 h, the cloudy gray solution was placed in a room temperature water bath and treated carefully with Na$_2$SO$_4$·10H$_2$O (996 mg). The bath was removed and the reaction stirred vigorously for 1 h followed by an additional Na$_2$SO$_4$·10H$_2$O (959 mg) and stirring overnight. The white precipitate was separated from the organics, rinsed with EtOAc (5×5 mL) and concentrated to a clear, colorless oil of (E)-7-(2,5-dimethoxy-3,4,6-trimethylphenyl)-5-methylhept-5-en-1-amine. The crude amine was dissolved into Et$_3$N (2 mL) and treated with neat Ac$_2$O (0.75 mL) over 5 minutes. The reaction exothermed slightly and was allowed to stir overnight at room temperature before being quenched by addition of H$_2$O (10 mL) and EtOAc (10 mL). The layers were separated and the aqueous phase extracted using EtOAc (3×10 mL). The combined organics were washed with H$_2$O (2×10 mL) and saturated NaCl solution (2×15 mL) before being dried over anhydrous Na$_2$SO$_4$ and concentration to a brown oil. Flash chromatography on silica gave N-((E)-7-(2,5-dimethoxy-3,4,6-trimethylphenyl)-5-methylhept-5-enyl)acetamide as an off-white crystalline solid, 130 mg (74.7%)

Data for (E)-7-(2,5-dimethoxy-3,4,6-trimethylphenyl)-5-methylhept-5-en-1-amine: $^1$H NMR (400 MHz, CDCl$_3$) d 5.05 (t, J=6.0 Hz, 1H), 3.63 (s, 6H), 3.35 (d, J=6.0 Hz, 2H), 2.64 (t, J=6.8 Hz, 2H), 2.16 (s, 9H), 1.97 (m, 2H), 1.75 (s, 3H), 1.63 (m, 2H), 1.38 (m, 3H). $^{13}$C NMR (100 MHz, CDCl$_3$) d 152.9, 152.6, 134.9, 131.5, 128.1, 127.8, 127.6, 123.2, 62.1, 60.7, 60.0, 42.0, 39.3, 33.4, 26.0, 16.1, 12.7, 12.6, 12.0.

Data for N-((E)-7-(2,5-dimethoxy-3,4,6-trimethylphenyl)-5-methylhept-5-enyl)acetamide: $^1$H NMR (400 MHz, CDCl$_3$) d 5.66 (br s, 1H), 5.04 (t, J=6.0 Hz, 1H), 3.63 (s, 6H), 3.34 (d, J=6.4 Hz, 2H), 3.18 (q, J=5.6 Hz, 2H), 2.17 (s, 9H), 1.94 (m, 5H), 1.74 (S, 3H), 1.41 (m, 4H). $^{13}$C NMR (100 MHz, CDCl$_3$) d 169.9, 153.0, 152.6, 134.6, 131.4, 128.2, 127.8, 127.6, 123.5, 60.8, 60.0, 39.5, 39.1, 29.1, 26.1, 25.1, 23.2, 16.1, 12.7, 12.6, 12.1.

N-((5E)-5-methyl-7-(2,4,5-trimethyl-3,6-dioxocyclohexa-1,4-dienyl)hept-5-enyl)acetamide

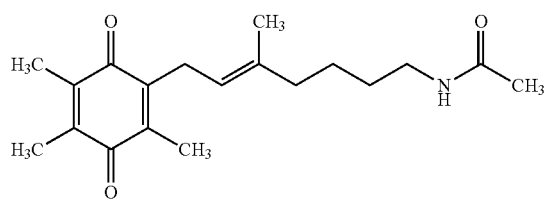 [SMILES: CC(=O)NCCCC/C(C)=C/CC1=C(C)C(=O)C(C)=C(C)C1=O]

Ceric ammonium nitrate (90.1 mg, 0.164 mmol) was dissolved into H$_2$O (0.5 mL) and AcCN (0.5 mL) and cooled to 0° C. A solution containing 25.2 mg N-((E)-7-(2,5-dimethoxy-3,4,6-trimethylphenyl)-5-methylhept-5-enyl)acetamide (0.0725 mmol) in AcCN (1 mL) and CH$_2$Cl$_2$ (0.25 mL) was added over 0.5 min. The reaction was stirred for 0.75 h at 0° C. then diluted with H$_2$O (2 mL). The layers were separated and the organic phase diluted with EtOAc (5 mL) and washed with H$_2$O (3×2 mL). The combined aqueous phase was back extracted using EtOAc (3×4 mL) and discarded. The combined organics were washed with brine (2×3 mL), dried over Na$_2$SO$_4$, concentrated in vacuo and subjected to flash chromatography (SiO$_2$) gave N-((5E)-5-methyl-7-(2,4,5-trimethyl-3,6-dioxocyclohexa-1,4-dienyl)hept-5-enyl)acetamide as a bright yellow liquid. $^1$H NMR (400 MHz, CDCl$_3$) d 5.61 (br s, 1H), 3.20 (m, 4H), 2.01 (m, 14H), 1.72 (s, 3H), 1.41 (m, 2H). $^1$C NMR (100 MHz, CDCl$_3$) d 187.9, 187.1, 170.0, 143.1, 140.43 140.37, 136.7, 119.9, 60.1, 39.5, 39.2, 29.1, 25.6, 25.0, 23.3, 16.1, 12.4, 12.2.

(E)-7-(2,5-dimethoxy-3,4,6-trimethylphenyl)-5-methylhept-5-enal

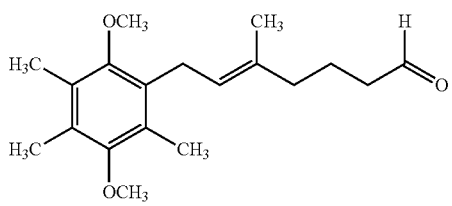 [SMILES: COc1c(C)c(C)c(OC)c(C/C=C(\C)CCCC=O)c1C]

(E)-7-(2,5-dimethoxy-3,4,6-trimethylphenyl)-5-methyl-hept-5-enenitrile (178 mg, 0.59 mmol) was dried azeotropically with toluene in vacuo (3×2 mL), redissolved into toluene (3 mL) and cooled to 0° C. DIBALH (1.0 M in heptane, 0.9 mmol) was added over 3 minutes dropwise. After 1 h, H$_2$O (2 ml) and aqueous H$_2$SO$_4$ (6 mL 2.5 M) were added and the mixture let warm to room temperature for 2.5 h. MTBE (5 mL) was added, the layers separated and the aqueous phase extracted 3×5 mL MTBE. The combined organics were washed with brine (10 mL), dried over anhydrous Na$_2$SO$_4$ and concentrated to give (E)-7-(2,5-dimethoxy-3,4,6-trimethylphenyl)-5-methylhept-5-enal as a colorless oil.

(E)-7-(2,5-dimethoxy-3,4,6-trimethylphenyl)-5-methylhept-5-en-1-ol

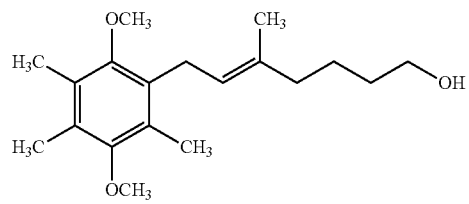 [SMILES: COc1c(C)c(C)c(OC)c(C/C=C(\C)CCCCO)c1C]

Crude (E)-7-(2,5-dimethoxy-3,4,6-trimethylphenyl)-5-methylhept-5-enenitrile in MeOH (3 mL) was cooled to 0° C. and treated with NaBH$_4$ (64.3 mg, 1.74 mmol), which gave immediate effervescence. After 12 h, H$_2$O (10 mL) was added (caution: copious gas evolution), MTBE (10 mL) was added, separated and the aqueous phase extracted with MTBE (3×10 mL). The combined organics were washed with H$_2$O (10 mL), brine (10 mL), dried over Na$_2$SO$_4$ and concentrated to give (E)-7-(2,5-dimethoxy-3,4,6-trimethylphenyl)-5-methylhept-5-en-1-ol as a pale yellow oil.

(E)-7-(2,5-dimethoxy-3,4,6-trimethylphenyl)-5-methylhept-5-enyl acetate

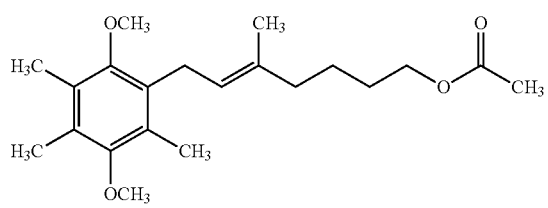 [SMILES: COc1c(C)c(C)c(OC)c(C/C=C(\C)CCCCOC(C)=O)c1C]

(E)-7-(2,5-dimethoxy-3,4,6-trimethylphenyl)-5-methyl-hept-5-en-1-ol in pyridine (2 mL) was treated with Ac$_2$O (2 mL) at 0° C. and let stir overnight. The reaction was quenched with H$_2$O (10 mL) followed by addition of EtOAc (10 mL) and separated. The aqueous phase was extracted with EtOAc (3×10 mL) and the combined organics washed with brine (15 mL), dried over anhydrous Na$_2$SO$_4$ and concentrated to a yellow oil. Flash chromatography on silica yielded 77.9 mg (62.3%) of (E)-7-(2,5-dimethoxy-3,4,6-trimethylphenyl)-5-methylhept-5-enyl acetate as a clear oil.

(E)-5-methyl-7-(2,4,5-trimethyl-3,6-dioxocyclohexa-1,4-dienyl)hept-5-enyl acetate

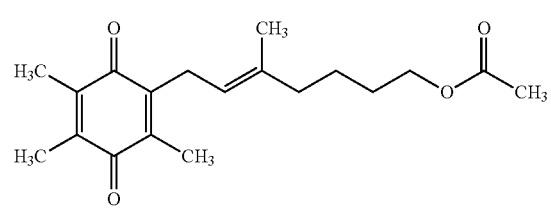 [SMILES: CC(=O)OCCCC/C(C)=C/CC1=C(C)C(=O)C(C)=C(C)C1=O]

Ceric ammonium nitrate (270 mg, 0.498 mmol) was dissolved into H$_2$O (0.75 mL) and AcCN (1.5 mL) and the solution chilled to 0° C. 77.9 mg of (E)-7-(2,5-dimethoxy-3,4,6-trimethylphenyl)-5-methylhept-5-enyl acetate (0.223 mmol) in AcCN (1.5 mL) was added over 2 minutes and the dark orange solution stirred for 0.5 h. H$_2$O (3 mL) and EtOAc (3 mL) were then added, the layers separated and the organics washed 2×2 mL H$_2$O. The combined aqueous phase was back extracted 3×5 mL EtOAc and the combined organics washed 2×5 mL saturated NaCl solution and dried over anhydrous Na$_2$SO$_4$. The resulting yellow liquid was concentrated to a yellow oil and subjected to flash chromatography, which yielded 25.8 mg of (E)-5-methyl-7-(2,4,5-trimethyl-3,6-dioxocyclohexa-1,4-dienyl)hept-5-enyl acetate as a bright yellow oil (36.2%). $^1$H NMR (400 MHz, CDCl$_3$) d 4.95 (t, J=6.4 Hz, 1H), 4.02 (t, J=6.8 Hz, 2H), 3.19 (d, J=6.8 Hz, 2H), 2.01 (m, 11H), 1.73 (s, 3H), 1.55 (m, 2H) 1.42 (m, 2H). $^{13}$C NMR (100 MHz, CDCl$_3$) d 187.9, 187.0, 171.1, 143.0, 140.4, 140.3, 136.7, 119.9, 64.4, 39.1, 28.1, 25.6, 24.1, 20.9, 16.1, 12.3, 12.1.

(E)-2-(7-hydroxy-3-methylhept-2-enyl)-3,5,6-trimethylcyclohexa-2,5-diene-1,4-dione

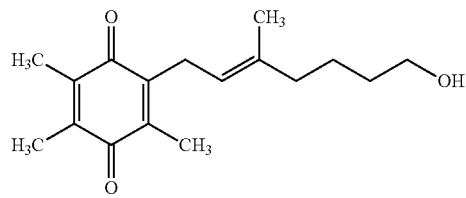 [SMILES: CC1=C(C)C(=O)C(C/C=C(\C)CCCCO)=C(C)C1=O]

(E)-7-(2,5-dimethoxy-3,4,6-trimethylphenyl)-5-methyl-hept-5-en-1-ol (29.7 mg, 0.097 mmol) in AcCN (0.5 mL) with 2 drops of H$_2$O was cooled to 0° C. CAN (114.7 mg, 0.209 mmol) was dissolved into AcCN (0.2 mL) and H$_2$O (0.5 mL) and added to a stirred solution of alcohol at 0° C. The reaction was stirred at 0° C. for 1 h and H$_2$O (2 mL) and EtOAc (2 mL) was added, the layers separated and the aqueous phase extracted 3×2 mL EtOAc. The combined organics were washed 2×2 mL saturated brine, dried over anhydrous Na$_2$SO$_4$ and concentrated to a yellow oil. Flash chromatography yielded (E)-2-(7-hydroxy-3-methylhept-2-enyl)-3,5,6-trimethylcyclohexa-2,5-diene-1,4-dione (2.2 mg) as a yellow oil (8.2%). $^{13}$C NMR (100 MHz, CDCl$_3$) δ 187.9, 187.0, 143.1, 140.4, 104.3, 134.0, 119.7, 77.2, 62.9, 39.3, 32.3, 25.6, 24.0, 16.2, 12.4, 12.3, 12.2

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of the formula:

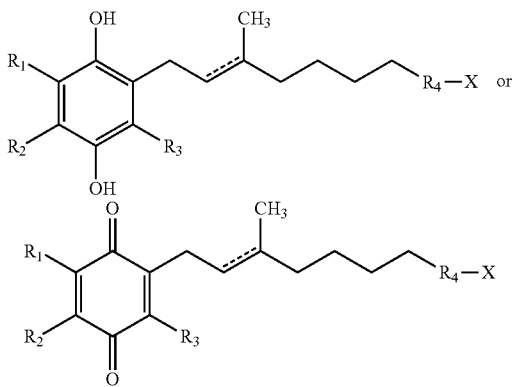

wherein the bond indicated with a dashed line is a single or double bond;

where $R_1$, $R_2$, and $R_3$ are independently selected from the group consisting of —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, —$C_2$-$C_5$ haloalkynyl, —S—$R_5$, —CN, —F, —Cl, —Br, —I, —$N_3$, and —$NR_5R_6$, where at least one of $R_1$, $R_2$, and $R_3$ is independently selected from —$C_2$-$C_5$ alkyl;

where $R_5$ and $R_6$ are independently selected from the group consisting of —H, —$C_1$-$C_5$ alkyl, —$C_3$-$C_6$ cycloalkyl, —$C_1$-$C_5$ haloalkyl, aryl, heteroaryl, —(C=O)—$C_1$-$C_8$ alkyl, —(C=O)—$C_0$-$C_8$ alkyl-$C_6$-$C_{10}$ aryl-$C_0$-$C_8$ alkyl, or where $R_5$ and $R_6$ selected from these groups are combined to form a ring;

where $R_4$ represents a linear or branched group containing 1 to 32 carbon atoms and any number of single, double, or triple bonds in any chemically possible combination;

where X is selected from the group consisting of —F, —Cl, —Br, —I, —CN, —$N_3$, —$NR_7R_8$, and —$OR_9$;

where $R_7$ and $R_8$ are independently selected from the group consisting of —H, —$C_1$-$C_8$ alkyl —$C_1$-$C_8$ haloalkyl, and —(C=O)—$C_1$-$C_8$ alkyl or where either one of $R_7$ and $R_8$ is independently selected from the group consisting of —(C=O)—$C_1$-$C_8$ haloalkyl; —(C=O)—$NH_2$; —(C=O)—$NHC_1$-$C_8$ alkyl; —(C=O)—$NHC_1$-$C_8$ haloalkyl; —(C=O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from the group consisting of —NH—, —N($C_1$-$C_4$ alkyl)-, —O—, and —S— is optionally incorporated in the ring formed by $R_{20}$ and $R_{21}$ and the nitrogen atom to which they are attached; —(C=O)—$OC_1$-$C_8$ alkyl; —(C=O)—$OC_1$-$C_8$ haloalkyl; —$S(O)_2C_1$-$C_8$ alkyl; —$S(O)_2$ aryl; and —$S(O)_2$ aralkyl, and where the other of $R_7$ and $R_8$ is —H, —$C_1$-$C_8$ alkyl or —$C_1$-$C_8$ haloalkyl or where $R_7$ and $R_8$ selected from these groups are combined to form a ring, or where $R_7$ is —$(CH_2)_p$—, $R_8$ is —$(CH_2)_q$—, p and q are independently integers between 0 and 7 inclusive, p+q is between 2 and 7 inclusive, $R_7$ and $R_8$ together with the nitrogen atom to which they are attached combine to form a 3- to 8-membered ring, and where another group selected from the group consisting of —NH—, —N($C_1$-$C_4$ alkyl)-, —O—, and —S— is optionally incorporated in the ring formed by $R_7$ and $R_8$ and the nitrogen atom to which they are attached;

where $R_9$ is independently selected from the group consisting of —H; —$C_1$-$C_8$ alkyl; —$C_1$-$C_8$ haloalkyl; —(C=O)—$C_1$-$C_8$ alkyl; —(C=O)—$C_1$-$C_8$ haloalkyl; —(C=O)—$NH_2$; —(C=O)—$NHC_1$-$C_8$ alkyl; —(C=O)—$NHC_1$-$C_8$ haloalkyl; —(C=O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from the group consisting of —NH—, —N($C_1$-$C_4$ alkyl)-, —O—, and —S— is optionally incorporated in the ring formed by $R_{20}$ and $R_{21}$ and the nitrogen atom to which they are attached; —(C=O)—$OC_1$-$C_8$ alkyl; —(C=O)—$OC_1$-$C_8$ haloalkyl; —$S(O)_2C_1$-$C_8$ alkyl; and —$S(O)_2$ aryl;

or any stereoisomer, mixture of stereoisomers, or salt, thereof.

2. The compound of claim 1, wherein $R_1$, $R_2$, and $R_3$ are independently selected from the group consisting of —H, —$C_1$-$C_5$ alkyl, —$C_1$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl, and where at least one of $R_1$, $R_2$, and $R_3$ is independently selected from the group consisting of —$C_2$-$C_5$ alkyl, —$C_2$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl.

3. The compound of claim 1, wherein at least two of $R_1$, $R_2$, and $R_3$ are independently selected from the group consisting of —$C_2$-$C_5$ alkyl, —$C_2$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl.

4. The compound of claim 3, wherein $R_1$, $R_2$, and $R_3$ are independently selected from the group consisting of —$C_2$-$C_5$ alkyl, —$C_2$-$C_5$ haloalkyl, —$C_2$-$C_5$ alkenyl, —$C_2$-$C_5$ haloalkenyl, —$C_2$-$C_5$ alkynyl, and —$C_2$-$C_5$ haloalkynyl.

5. A compound of the formula:

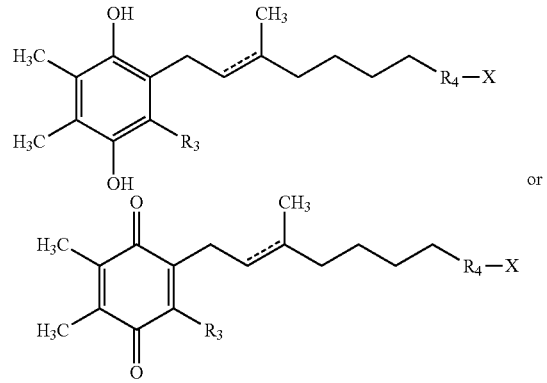

wherein the bond indicated with a dashed line is a single or double bond;

where $R_1$, $R_2$, and $R_3$ are independently selected from the group consisting of —H, —$C_1$-$C_5$ alkyl, —$C_1$-$C_5$ haloalkyl, —C$_2$-C$_5$ alkenyl, —C$_2$-C$_5$ haloalkenyl, —C$_2$-C$_5$ alkynyl, —C$_2$-C$_5$ haloalkynyl, —S—R$_5$, —CN, —F, —Cl, —Br, —I, —N$_3$, and —NR$_5$R$_6$; where R$_5$ and R$_6$ are independently selected from the group consisting of —H, —C$_1$-C$_5$ alkyl, —C$_3$-C$_6$ cycloalkyl, —C$_1$-C$_5$ haloalkyl, aryl, heteroaryl, (C=O)—C$_1$-C$_8$ alkyl, and —(C=O)—C$_0$-C$_8$ alkyl-C$_6$-C$_{10}$ aryl-C$_0$-C$_8$ alkyl, or where R$_5$ and R$_6$ selected from these groups are combined to form a ring;

where R$_4$ is —(CH$_2$)$_n$C(CH$_3$)$_2$—, where n is an integer from 0 to 15 inclusive;

where X is selected from the group consisting of —F, —Cl, —Br, —I, —CN, —N$_3$, —NR$_7$R$_8$, and —OR$_9$;

where R$_7$ and R$_8$ are independently selected from the group consisting of —H, —C$_1$-C$_8$ alkyl, —C$_1$-C$_8$ haloalkyl, and —(C=O)—C$_1$-C$_8$ alkyl, or where either one of R$_7$ and R$_8$ are independently selected from the group consisting of —(C=O)—C$_1$-C$_8$ haloalkyl; —(C=O)—NH$_2$; —(C=O)—NHC$_1$-C$_8$ alkyl; —(C=O)—NHC$_1$-C$_8$ haloalkyl; —(C=O)—NR$_{20}$R$_{21}$ where R$_{20}$ is —(CH$_2$)$_p$—, R$_{21}$ is —(CH$_2$)$_q$—, p and q are independently integers between 0 and 7 inclusive, p+q is between 2 and 7 inclusive, R$_{20}$ and R$_{21}$ together with the nitrogen atom to which they are attached combine to form a 3- to 8-membered ring, and where another group selected from the group consisting of —NH—, —N(C$_1$-C$_4$ alkyl)-, —O—, and —S— is optionally incorporated in the ring formed by R$_{20}$ and R$_{21}$ and the nitrogen atom to which they are attached; —(C=O)—OC$_1$-C$_8$ alkyl; —(C=O)—OC$_1$-C$_8$ haloalkyl; —S(O)$_2$C$_1$-C$_8$ alkyl; —S(O)$_2$ aryl; and —S(O)$_2$ aralkyl, and where the other of R$_7$ and R$_8$ is —H, —C$_1$-C$_8$ alkyl or —C$_1$-C$_8$ haloalkyl or where R$_7$ and R$_8$ selected from these groups are combined to form a ring, or where R$_7$ is —(CH$_2$)$_p$—, R$_8$ is —(CH$_2$)$_q$—, p and q are independently integers between 0 and 7 inclusive, p+q is between 2 and 7 inclusive, R$_7$ and R$_8$ together with the nitrogen atom to which they are attached combine to form a 3- to 8-membered ring, and where another group selected from the group consisting of —NH—, —N(C$_1$-C$_4$ alkyl)-, —O—, and —S— is optionally incorporated in the ring formed by R$_7$ and R$_8$ and the nitrogen atom to which they are attached;

where R$_9$ is independently selected from the group consisting of —H; —C$_1$-C$_8$ alkyl; —C$_1$-C$_8$ haloalkyl; —(C=O)—C$_1$-C$_8$ alkyl; —(C=O)—C$_1$-C$_8$ haloalkyl; —(C=O)—NH$_2$; —(C=O)—NHC$_1$-C$_8$ alkyl; —(C=O)—NHC$_1$-C$_8$ haloalkyl; —(C=O)—NR$_{20}$R$_{21}$ where R$_{20}$ is —(CH$_2$)$_p$—, R$_{21}$ is —(CH$_2$)$_q$—, p and q are independently integers between 0 and 7 inclusive, p+q is between 2 and 7 inclusive, R$_{20}$ and R$_{21}$ together with the nitrogen atom to which they are attached combine to form a 3- to 8-membered ring, and where another group selected from the group consisting of —NH—, —N(C$_1$-C$_4$ alkyl)-, —O—, and —S— is optionally incorporated in the ring formed by R$_{20}$ and R$_{21}$ and the nitrogen atom to which they are attached; —(C=O)—OC$_1$-C$_8$ alkyl; —(C=O)—OC$_1$-C$_8$ haloalkyl; —S(O)$_2$C$_1$-C$_8$ alkyl; and —S(O)$_2$ aryl;

or any stereoisomer, mixture of stereoisomers, or salt, thereof.

6. The compound of claim 5 wherein X is —OH.

7. A compound of the formula:

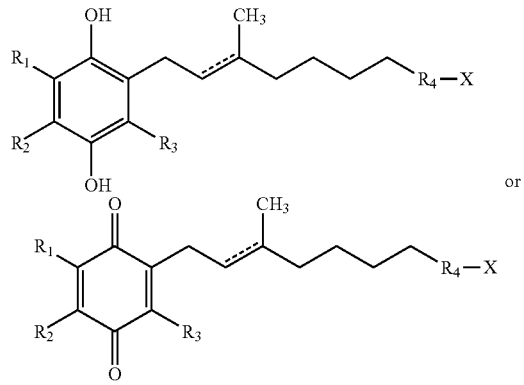

wherein the bond indicated with a dashed line is a single or double bond;

where R$_1$, R$_2$, and R$_3$ are independently selected from the group consisting of —H, —C$_1$-C$_5$ alkyl, —C$_1$-C$_5$ haloalkyl, —C$_2$-C$_5$ alkenyl, —C$_2$-C$_5$ haloalkenyl, —C$_2$-C$_5$ alkynyl, —C$_2$-C$_5$ haloalkynyl, —O—R$_5$, —S—R$_5$, —CN, —F, —Cl, —Br, —I, —N$_3$, and —NR$_5$R$_6$;

where R$_5$ is independently selected from the group consisting of —H, —C$_2$-C$_5$ alkyl, —C$_3$-C$_6$ cycloalkyl, —C$_1$-C$_5$ haloalkyl, aryl, and heteroaryl, and R$_6$ is independently selected from the group consisting of —H, —C$_1$-C$_5$ alkyl, —C$_3$-C$_6$ cycloalkyl, —C$_1$-C$_5$ haloalkyl, aryl, heteroaryl, (C=O)—C$_1$-C$_8$ alkyl, and —(C=O)—C$_0$-C$_8$ alkyl-C$_6$-C$_{10}$ aryl-C$_0$-C$_8$ alkyl, or where R$_5$ and R$_6$ selected from these groups are combined to form a ring;

where R$_4$ is —(CH$_2$)$_n$C(CH$_3$)$_2$— where n is an integer from 0 to 15 inclusive;

where X is selected from the group consisting of —F, —Cl, —Br, —I, —CN, —N$_3$, —NR$_7$R$_8$, and —OR$_9$;

where R$_7$ and R$_8$ are independently selected from the group consisting of —H, —C$_1$-C$_8$ alkyl —C$_1$-C$_8$ haloalkyl, and —(C=O)—C$_1$-C$_8$ alkyl, or where either one of R$_7$ and R$_8$ is independently selected from the group consisting of —(C=O)—C$_1$-C$_8$ haloalkyl; —(C=O)—NH$_2$; —(C=O)—NHC$_1$-C$_8$ alkyl; —(C=O)—NHC$_1$-C$_8$ haloalkyl; —(C=O)—NR$_{20}$R$_{21}$ where R$_{20}$ is —(CH$_2$)$_p$—, R$_{21}$ is —(CH$_2$)$_q$—, p and q are independently integers between 0 and 7 inclusive, p+q is between 2 and 7 inclusive, R$_{20}$ and R$_{21}$ together with the nitrogen atom to which they are attached combine to form a 3- to 8-membered ring, and where another group selected from the group consisting of —NH—, —N(C$_1$-C$_4$ alkyl)-, —O—, and —S— is optionally incorporated in the ring formed by R$_{20}$ and R$_{21}$ and the nitrogen atom to which they are attached; —(C=O)—OC$_1$-C$_8$ alkyl; —(C=O)—OC$_1$-C$_8$ haloalkyl; —S(O)$_2$C$_1$-C$_8$ alkyl; —S(O)$_2$ aryl; and —S(O)$_2$ aralkyl, and where the other of R$_7$ and R$_8$ is —H, —C$_1$-C$_8$ alkyl or —C$_1$-C$_8$ haloalkyl or where R$_7$ and R$_8$ selected from these groups are combined to form a ring, or where R$_7$ is —(CH$_2$)$_p$—, R$_8$ is —(CH$_2$)$_q$—, p and q are independently integers between 0 and 7 inclusive, p+q is between 2 and 7 inclusive, R$_7$ and R$_8$ together with the nitrogen atom to which they are attached combine to form a 3- to 8-membered ring, and where another group selected from the group consisting of —NH—, —N($C_1$-$C_4$ alkyl)-, —O—, and —S— is optionally incorporated in the ring formed by $R_7$ and $R_8$ and the nitrogen atom to which they are attached;

where $R_9$ is independently selected from the group consisting of —H; —$C_1$-$C_8$ alkyl; —$C_1$-$C_8$ haloalkyl; —(C=O)—$C_1$-$C_8$ alkyl; —(C=O)—$C_1$-$C_8$ haloalkyl; —(C=O)—$NH_2$; —(C=O)—$NHC_1$-$C_8$alkyl; —(C=O)—$NHC_1$-$C_8$ haloalkyl; —(C=O)—$NR_{20}R_{21}$ where $R_{20}$ is —$(CH_2)_p$—, $R_{21}$ is —$(CH_2)_q$—, p and q are independently integers between 0 and 7 inclusive, p+q is between 2 and 7 inclusive, $R_{20}$ and $R_{21}$ together with the nitrogen atom to which they are attached combine to form a 3- to 8-membered ring, and where another group selected from the group consisting of —NH—, —N($C_1$-$C_4$ alkyl)-, —O—, and —S— is optionally incorporated in the ring formed by $R_{20}$ and $R_{21}$ and the nitrogen atom to which they are attached; —(C=O)—$OC_1$-$C_8$ alkyl; —(C=O)—$OC_1$-$C_8$ haloalkyl; —$S(O)_2C_1$-$C_8$ alkyl; and —$S(O)_2$ aryl;

or any stereoisomer, mixture of stereoisomers, or salt thereof.

8. The compound of claim 7 wherein X is —OH.

\* \* \* \* \*

UNITED STATES PATENT AND TRADEMARK OFFICE
CERTIFICATE OF CORRECTION

PATENT NO. : 9,932,286 B2
APPLICATION NO. : 14/983330
DATED : April 3, 2018
INVENTOR(S) : Miller et al.

Page 1 of 2

It is certified that error appears in the above-identified patent and that said Letters Patent is hereby corrected as shown below:

In the Claims

In Column 79, Lines 47-49, Claim 1 delete:
"where $R_7$ and $R_8$ are independently selected from the group consisting of —H, —$C_1$-$C_8$ alkyl —$C_1$-$C_8$ haloalkyl, and —(C=O)—$C_1$-$C_8$ alkyl"

And insert:
-- where $R_7$ and $R_8$ are independently selected from the group consisting of —H, —$C_1$-$C_8$ alkyl, —$C_1$-$C_8$ haloalkyl, and —(C=O)—$C_1$-$C_8$ alkyl; --

In Column 80, regarding Claim 5, delete:

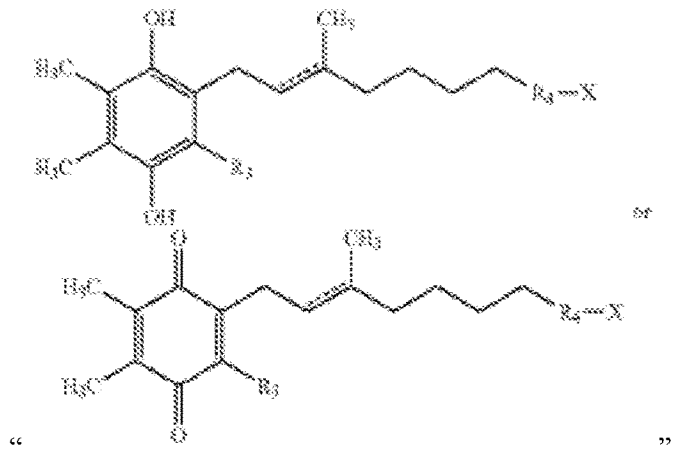

Signed and Sealed this
Twenty-eighth Day of August, 2018

Andrei Iancu
*Director of the United States Patent and Trademark Office*

And insert:
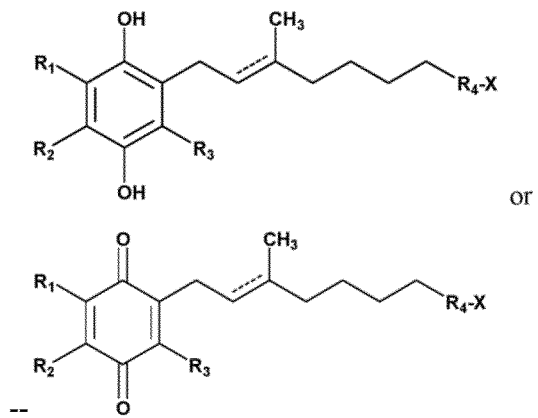 or
--   --
In Column 81, Line 7, Claim 5 delete:
"(C=O)—$C_1$-$C_8$ alkyl"
And insert:
-- —(C=O)—$C_1$-$C_8$ alkyl --
In Column 82, Line 33, Claim 7 delete:
"(C=O)—$C_1$-$C_8$ alkyl"
And insert:
-- —(C=O)—$C_1$-$C_8$ alkyl --
In Column 83, Line 8, Claim 7 delete:
"—(C=O)—NH$C_1$-$C_8$alkyl"
And insert:
-- —(C=O)—NH$C_1$-$C_8$ alkyl --